(12) United States Patent
Beaudry

(10) Patent No.: US 7,456,332 B2
(45) Date of Patent: Nov. 25, 2008

(54) DRESSING AND AN EPIDERMAL POSITIONING MECHANISM AND METHOD FOR USING SAME

(76) Inventor: Wallace J Beaudry, N9330 County Hwy. H, Elkhart Lake, WI (US) 53020

( * ) Notice: Subject to any disclaimer, the term of this patent is extended or adjusted under 35 U.S.C. 154(b) by 273 days.

(21) Appl. No.: 11/024,988

(22) Filed: Dec. 29, 2004

(65) Prior Publication Data

US 2005/0131329 A1    Jun. 16, 2005

Related U.S. Application Data

(60) Division of application No. 10/133,230, filed on Apr. 26, 2002, now Pat. No. 7,022,891, which is a continuation-in-part of application No. 09/616,426, filed on Jul. 14, 2000, which is a division of application No. 09/180,572, filed as application No. PCT/US97/00868 on Jan. 17, 1997.

(60) Provisional application No. 60/017,258, filed on May 10, 1996.

(51) Int. Cl.
*A61F 13/00* (2006.01)
*A61M 15/00* (2006.01)

(52) U.S. Cl. .............................. 602/54; 602/41; 602/48; 128/200.24; 128/207.24; 606/216

(58) Field of Classification Search ............. 602/41–59; 128/888, 889; 606/213–216
See application file for complete search history.

(56) References Cited

U.S. PATENT DOCUMENTS

| | | | |
|---|---|---|---|
| 1,230,445 A | 6/1917 | Teed et al. |
| 1,435,853 A | 11/1922 | Johnson |
| 2,018,517 A | 10/1935 | Fetter |
| 3,085,024 A | 4/1963 | Blackford |
| 3,426,751 A | 2/1969 | Radewan |
| 3,811,438 A | 5/1974 | Economou |
| 4,120,304 A | 10/1978 | Moor |
| 4,213,452 A | 7/1980 | Shippert |
| 4,221,215 A | 9/1980 | Mandelbaum |
| 4,222,383 A | 9/1980 | Schossow |
| 4,366,814 A | 1/1983 | Riedel |
| 4,605,005 A | 8/1986 | Sheehan |
| 4,702,736 A | 10/1987 | Kalt et al. |
| 4,738,662 A | 4/1988 | Kalt et al. |
| 4,742,826 A | 5/1988 | McLorg |

(Continued)

FOREIGN PATENT DOCUMENTS

CH    161433    4/1933

(Continued)

*Primary Examiner*—Kim M Lewis
(74) *Attorney, Agent, or Firm*—Ryan Kromholz & Manion S.C.

(57) ABSTRACT

An epidermal positioning mechanism for use with an application to a predetermined epidermal surface. The epidermal positioning mechanism comprises a strip of material having a first end portion of a predetermined shape, a second end portion of a predetermined shape, and middle portion coupling the first end portion to the second end portion. The first end portion and the second end portion each may include a side including an adhesive layer. An overlaying, non-adhesive barrier layer may be located between a portion of the adhesive layer and an end portion.

7 Claims, 48 Drawing Sheets

U.S. PATENT DOCUMENTS

| | | | |
|---|---|---|---|
| 4,793,337 A | 12/1988 | Freeman et al. |
| 4,823,789 A | 4/1989 | Beisang, II |
| 4,825,866 A | 5/1989 | Pierce |
| 4,838,878 A | 6/1989 | Kalt et al. |
| 4,919,654 A | 4/1990 | Kalt |
| 4,932,943 A | 6/1990 | Nowak |
| 4,966,590 A | 10/1990 | Kalt |
| 4,979,946 A | 12/1990 | Gilman |
| 4,986,815 A | 1/1991 | Schneider |
| 5,022,389 A | 6/1991 | Brennan |
| 5,052,381 A | 10/1991 | Gilbert et al. |
| 5,116,675 A | 5/1992 | Nash-Morgan |
| 5,156,641 A | 10/1992 | White |
| 5,158,555 A | 10/1992 | Porzilli |
| 5,172,688 A | 12/1992 | Dillon |
| 5,234,462 A | 8/1993 | Pavletic |
| 5,244,523 A | 9/1993 | Tollini |
| 5,336,219 A | 8/1994 | Krantz |
| 5,449,340 A | 9/1995 | Tollini |
| 5,456,660 A | 10/1995 | Reich et al. |
| 5,476,091 A | 12/1995 | Johnson |
| 5,505,958 A | 4/1996 | Bello et al. |
| 5,534,010 A | 7/1996 | Peterson |
| 5,538,500 A | 7/1996 | Peterson |
| 5,546,929 A | 8/1996 | Muchin |
| 5,549,103 A | 8/1996 | Johnson |
| 5,553,605 A | 9/1996 | Muchin |
| 5,611,333 A | 3/1997 | Johnson |
| 5,628,724 A | 5/1997 | DeBusk et al. |
| 5,681,579 A | 10/1997 | Freeman |
| 5,696,169 A | 12/1997 | Otsu et al. |
| 5,788,660 A * | 8/1998 | Resnik | 602/79 |
| 5,820,578 A | 10/1998 | Johansen |
| 5,843,025 A | 12/1998 | Shaari |
| 6,329,564 B1 * | 12/2001 | Lebner | 602/41 |
| 6,768,039 B1 | 7/2004 | Beaudry |

FOREIGN PATENT DOCUMENTS

| | | |
|---|---|---|
| CH | 438583 | 6/1967 |
| DE | 4425554 | 6/1996 |
| EP | 0 331 954 A1 | 8/1989 |
| FR | 928389 | 12/1947 |
| FR | 1203376 | 1/1960 |
| GB | 615861 | 1/1949 |
| GB | 619165 | 3/1949 |
| GB | 1142148 | 2/1969 |
| GB | 1149790 | 9/1976 |
| NO | 308767 | 10/1910 |
| WO | WO 88/03788 | 6/1988 |
| WO | WO 92/22340 | 12/1992 |
| WO | WO 94/23675 | 10/1994 |
| WO | WO 96/01093 | 1/1996 |
| WO | WO 97/22314 | 6/1997 |

* cited by examiner

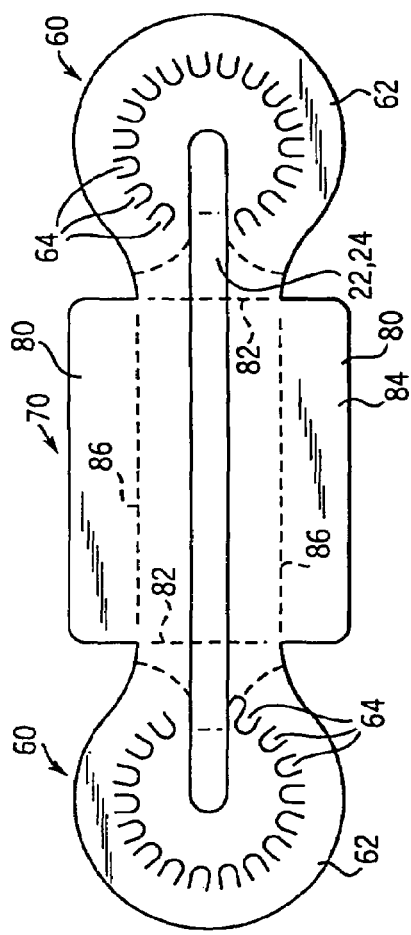
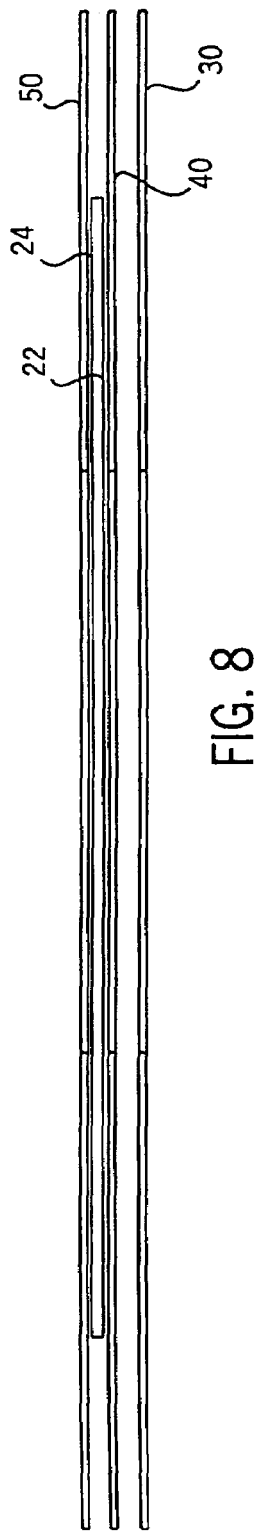
FIG. 7
FIG. 8

FIG. 15  FIG. 16  FIG. 17
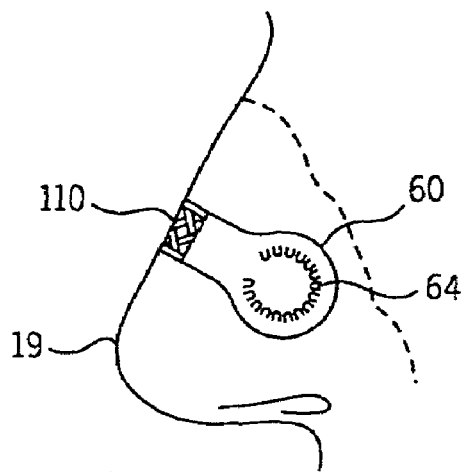
FIG. 26
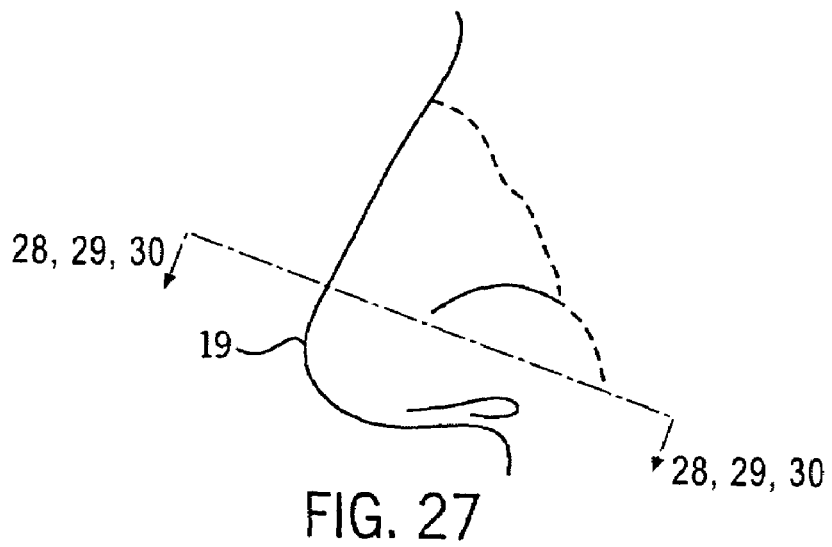
FIG. 27

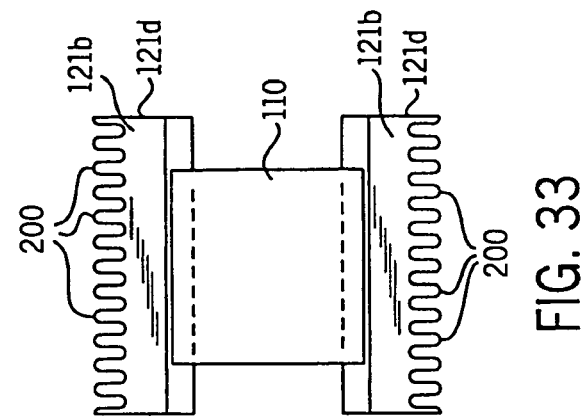
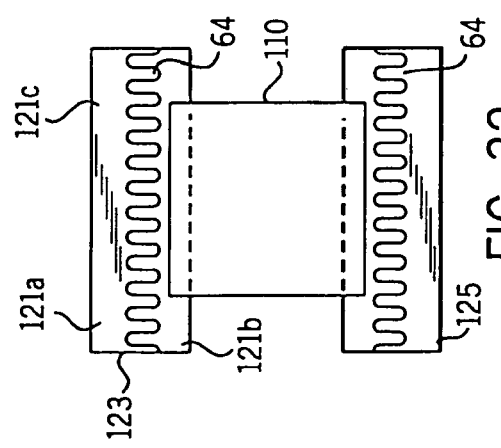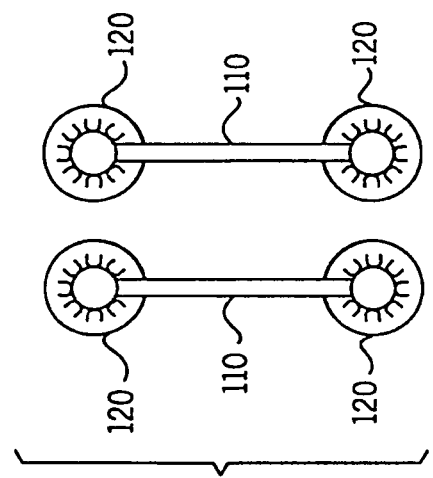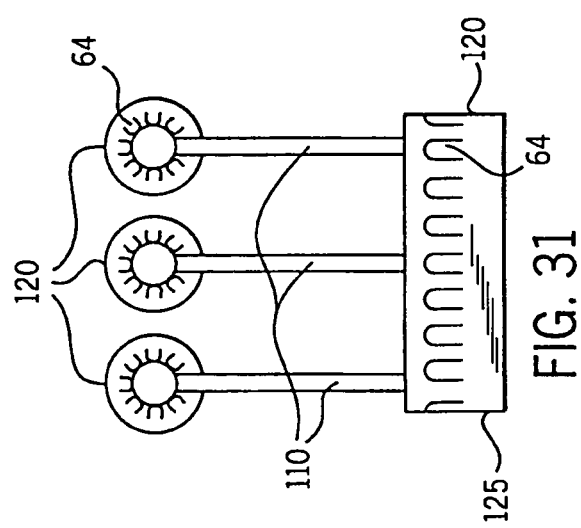

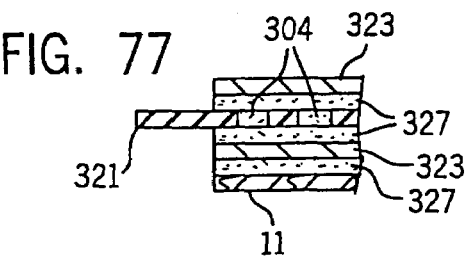
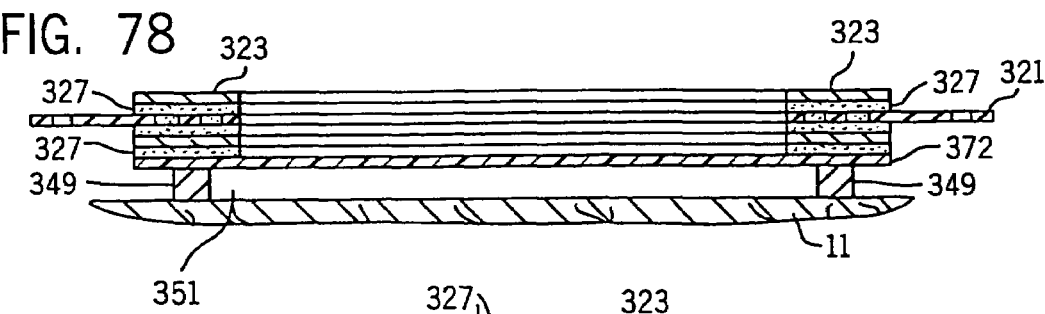
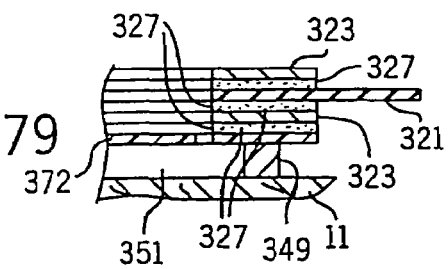
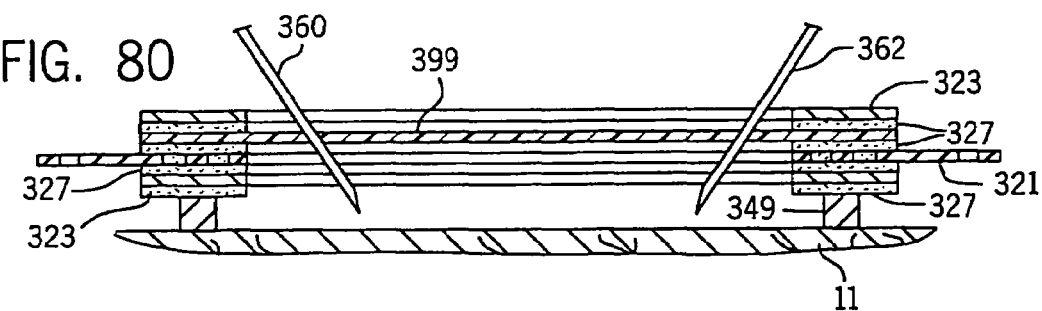
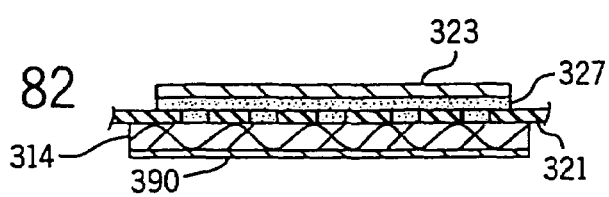
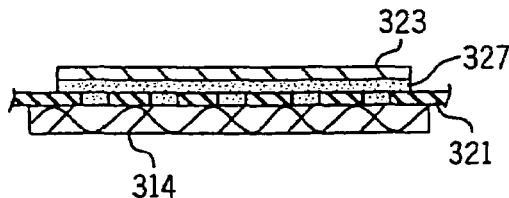

DRESSING AND AN EPIDERMAL POSITIONING MECHANISM AND METHOD FOR USING SAME

RELATED APPLICATIONS

This application is a divisional application of U.S. application Ser. No. 10/133,230 filed 26 Apr. 2002, now U.S. Pat. No. 7,022,891,which is a continuation-in-part application of prior U.S. application Ser. No. 09/616,426 filed 14 Jul. 2000, which is a divisional application of U.S. application Ser. No. 09/180,572 filed 11 Jan. 2000, which is a national stage application of PCT application Ser. No. PCT/US97/00868 filed 17 Jan. 1997, which claims the benefit of Provisional Application Ser. No. 60/017,258 filed 10 May 1996.

BACKGROUND OF THE INVENTION

The present invention relates generally to devices that may be used in the healing arts and arts generally related thereto. More specifically, the present invention relates to devices which may be used for a variety of purposes including but not limited to dressings for wounds, bandages, drug delivery systems, epidermal lifting mechanisms, and positioning mechanisms for positioning epidermal layers of skin on humans and/or animals in a predetermined manner. The present invention is thus believed to have application in the medical and veterinary sciences.

Several forms of the present invention relate to epidermal lifting mechanisms and methods for increasing the flow of gases into the human body and more specifically to an epidermal lifting mechanism and method for allowing more oxygen to pass through the nasal cavity thus increasing both the flow of oxygen into the lungs and the flow of air exhaled from the lungs. Consequently, embodiments of the present invention are also related to a group of devices which are sometimes called nasal dilators. The present invention provides a comfortable and effective device for allowing increased gas flow rates through the nasal passages and into the lungs.

Additionally, the present invention is an improvement in the field of bandages and suturing aids in that a person may use the present invention to hold the ends of a wound together or apart for the purposes of suturing or cleaning the wound and/or incision. Further, the device of the present invention may be used to apply medicine or anti-bacterial agents to a wound or incision.

Also, some embodiments of the present invention may be used to isolate a wound or burn in a sterile environment while allowing access to the wound area for purposes such as irrigating the wound. Further, some embodiments of the present invention may be used to stabilize the wound or burn area so that the skin around the wound or burn does not stretch with the movement of an individual and thus prevents further damage to the wound during the healing process and allows for more effective healing of the wound or burn.

SUMMARY OF THE INVENTION

The present invention has many applications. The present invention may be generally described as a structure for aiding in the following activities: as an epidermal lifting mechanism for providing a lifting force to a predetermined area of the epidermis, such as the area located to either side of the bridge of a person's nose to provide an increased flow rate of gas through (inhaled and exhaled) the nasal passage, e.g., a nasal dilator; a structure for aiding in keeping an incision open; a structure for aiding in keeping a wound open for cleansing; a structure for aiding in keeping the ends or edges of an incision or wound in close, neat, even, alignment by the application of an even pressure across the wound, burn, or incision, so that the area requiring treatment may heal, or be sutured and closed, neatly and thus develop minimal scar tissue; or as an epidermal positioning mechanism as a device for applying medicine to a wound or other desired place on the epidermis of a human or animal.

With respect to the invention's applications as a dressing the invention may be generally described as comprising: a first section, a second section, and a third section. Of these three sections, the first section is coupled to the second section and the second section is coupled to the third section. The second section comprising an elastic material with the first section and the third section each having a first side; and a predetermined portion of the first side including an adhesive located thereon. The second section of the invention may include a plurality of openings of a predetermined size and predetermined shape.

It should be noted that the predetermined shape or shapes of the openings may be spatially organized in a predetermined manner respective to each other. This is because in one embodiment of the present invention the second section is located between the first and third sections and is preferably composed of an elastic material. By placing openings in the elastic material at predetermined locations the strength of the elastic material, when the elastic material is stretched, may be varied and the distribution of force across the elastic material may by varied. Also, the openings can be used to provide a visual reference to a user of the amount of stress being placed upon the second section and whether or not that section has been stretched sufficiently or been stretched too much since the shape of the openings will change in response to the degree to which the elastic material is stretched. Such a visual reference would be useful to medical personnel where, e.g., it is desirable for a predetermined amount of pressure to be applied to a wound.

Further, the second section includes a first margin (if the second section is round then there is structurally just one annular margin near at least a portion of the perimeter of the second section) and a second margin. The first section may be integral or coupled to the second section at the first margin; and the third section may be integral or coupled to the second section at the second margin.

Preferably, but not necessarily, the first section and the third section are laminated materials comprising a first layer, a second intermediate layer, and a third layer; with the third layer including the first side coated with adhesive and protected prior to use by a silicone release liner. The second section includes a first margin and a second margin. The first section includes a first channel located between the first layer and the third layer of the first section for receiving the first margin. The second section includes a second channel located between the first layer and the third layer of the second section for receiving the second margin. The second intermediate layer comprising an adhesive material. The first margin and the second margin of the second section respectively including at least one opening and the first margin engaging the second intermediate layer in the first channel and the adhesive material extending through the opening of the first margin; and the second margin engaging the second intermediate layer in the second channel and the adhesive material extending through the opening of the second margin.

The first and third layer of the first section and the first and third layer of the third section preferably being an inelastic material in some embodiments. The inelastic material may be of any suitable material such as a TYVEC brand type of material.

Alternatively, the dressing mechanism may be described as comprising: a first section, a second section, and a third section such that the first section is coupled to the second section and the second section is coupled to the third section. The first section and the third section comprising an elastic material and the first section and the third section each having a first side; and a predetermined portion of the first side including an adhesive located thereon.

Further, the second section includes at least one opening of a predetermined size and the first section and the third section each include at least one opening comprising a predetermined shape. As previously noted the openings of predetermined shape are spatially organized in a predetermined manner respective to each other.

Also, the second section may include at least one margin and the first section and the third section each have a respective margin area. The first section margin is coupled to the second section at a first predetermined portion the margin of the second section. The third section margin being coupled to the second section at a second predetermined portion of the margin of the second section.

Preferably, the second section is a laminated material comprising at least a first layer, a second intermediate layer, and a third layer; the third layer including the first side. The first section and the third section including a first section margin and a third section margin. Both the first section margin and the third section margin being composed of an elastic material. The second section including at least one channel located between the first layer and the third layer of the second section at the second section margin for receiving the margins of the first and third sections. The second intermediate layer comprising an adhesive material. The first section margin and the third section margin respectively including at least one opening and the margins of the first and third sections engaging the second intermediate layer in the channel at the respective first predetermined margin area and second predetermined margin area so that the adhesive material extends through the openings formed in the material which makes up the first and third section margins. The first and third layer of the second section may, in this embodiment, comprises an inelastic material. The inelastic material may be a polyester.

Further, the second section includes at least one opening or at least one generally transparent section to either allow the wound or burn to be exposed to the air to be observed visually. Additionally, the second section could be modified to include a mechanism for irrigating the wound or burn under the bandage so that the wound or burn could be cleaned or treated without having to remove the dressing. Also, at least one side of the second section could be designed so that it is capable of isolating the wound in a clean environment by creating a solid antiseptic barrier around the wound through the use of a colloid type adhesive or be capable of contacting a wound or burn so that medicine could be applied to the wound or burn directly.

With respect the features of the present invention as an epidermal lifting mechanism, the epidermal lifting mechanism may be generally described as comprising at least one strip of material having a first side and a second side, the strip further including a first end portion and a second end portion. Between the first side and the second side are preferably one or more layers of predetermined materials.

These layers of materials include without limitation, a silicone coated release liner, an adhesive system to adhere the epidermal lifting mechanism to the nose, a top layer of material, and a spring mechanism. Obviously, the release liner is removed prior to placing the epidermal lifting mechanism on the bridge of the nose. The adhesive system, just like the adhesive system for the dressing mechanism, can include a pressure sensitive hypo-allergenic acrylic or a hydrocolloid material but any suitable adhesive system may be used. The top layer of material can be either a non-woven material or a material with some stretch characteristics such as a three mil polyurethane film. The spring mechanism may comprise a polyester film (usually 2 mils to 8 mils in thickness but any suitable thickness range may be used, e.g., 1-15 mils would be suitable as an alternative thickness range but any thickness range can be used depending upon the desired use and durability) laminated to a spun bonded polyester material. The spun bonded polyester material may or may not be coated with a pressure sensitive adhesive. The spring mechanism may be a plurality of materials which are laminated together.

Although unitary, the mechanism has the following components: a pair of nose pods and a bridge section. The nose pods include an exposed adhesive surface which is bonded to the skin on the sides of the nose. The bridge section of the device has at least one fulcrum point, located at the bridge of the nose when it is applied to the bridge of a nose, and lies across the bridge of the nose.

However, it should also be noted that the present invention could be applied to simply one side of the nose with the bridge section of the device ending at the top of the bridge of the nose and being adhered thereto. Alternatively, the bridge section could simply be a strip of resilient or elastic material which is connected to the cheek of the wearer at one end by use of an adhesive material and the nose pod being connected to the side of the nasal passage at the other end.

It should be noted that it is preferable for the nose pods to include horseshoe shaped slits or cuts which are made in the top layer of the material through the adhesive layer which, when applied to the nose, allows the spring action to generate a uniform lifting force in a suction cup like manner while at the same time applying a shearing force to the adhesive itself due to the presence of the slit structures, rather than a lifting force thereby creating flexibility from the lift point to the adhesion point. By decreasing the lifting (peel) force on the adhesive, the stability of the bond between the adhesive and the skin is greatly increased and allows more flexibility of the dilator during facial movement. Thus the dilator will stay comfortably in place even during vigorous movement by the wearer; even when used in applications other than a nasal dilator. The lifting (peel) force on the adhesive may be further decreased by use of a coextensive, overlaying barrier layer comprised of a non-adhesive material. The non-adhesive, overlaying barrier layer is preferably located between a portion of the adhesive material and the pod material such that an area of non-adhesiveness is created between the adhesive layer and the pod.

A pair of flaps attached adjacent to the bridge section of the epidermal lifting mechanism create another pair of fulcrum points (fulcrum point 2) between the bridge of the nose (fulcrum point 1) and the adhesive material thereby increasing the dilation force of the outer epidermis of the nasal passages. The additional fulcrum points are accomplished by folding of the flaps adjacent to the bridge section underneath the epidermal lifting mechanism allowing the adhesive area of each flap to adhere to the bottom adhesive area of the bridge section of the epidermal lifting mechanism securing it in place. The flaps include perforations for ease of folding.

As discussed above, the pair of flaps creates an additional fulcrum point. Further, when folded they provide a cushioned area for the bridge of the nose to cover the adhesive on the underside of the epidermal lifting mechanism so when applied for several hours and then removed discomfort to the skin tissue on the bridge of the nose is eliminated.

When the top and bottom spring laminates are laminated together and the epidermal lifting mechanism is applied to the nose, the bending of the multi-level springing increases the opening force to the nasal passages over a single level spring. Adding a layer of spring material on top of another layer of spring material creates a leaf spring action. Because there is a stretching force introduced into the top layer when bent over a fulcrum point, a stronger spring action is created as compared to a single layer spring of equal of thickness. Furthermore, bending over a fulcrum point or at multiple fulcrum points further improves the spring action.

Additionally, various pod configurations may be used to allow for flexibility of the bottom spring and/or to allow the pods to conform to the irregular surfaces of the nose or epidermal layer to which they are applied. Further, a fulcrum point may be provided by use of two, spaced apart pad structures having elastic material there between.

A key advantage of this mechanism is that anytime a person engages in physical activity that increases his or her heart rate, this mechanism allows for the delivery of more oxygen to the lungs. Further, the mechanism allows for more air to be effectively exhaled and thus both inhalation and exhalation are enhanced so overall breathing efficiency is enhanced.

Alternatively, this invention may be described as a method for increasing the flow rate of gas through the nasal passages, the method comprising the steps of applying the epidermal lifting mechanism by bending the spring material over the bridge of the nose so that the adhesive material of the nose pods comes into positive contact with the sides of the nose and releasing the nose pods thus allowing the springs to mechanically lift the epidermal surface of the nose and increase the size of the nasal passage openings.

Alternatively, the present invention may be structure which may be used as a nasal dilator wherein the nasal dilator comprises two separate pieces each capable of acting independently of the other. Each piece having at least one nose pod and an elastic member or strip attached to that nose pod. The elastic member or strip having a first end and a second end with the nose pods being attached to the first end. The elastic member having a second end attached to an anchor mechanism. The anchor mechanism having a first side and an adhesive material included thereon. The nose pod having the previously described structure for a nose pod. The anchor mechanism being applied to a predetermined area on a persons cheek a sufficient distance away from the side of the persons nose so that the nose pod, coupled to the elastic member, may be applied to the outside surface or epidermis surrounding the nasal passage of a persons nose and the elastic member retracting between the anchor mechanism and the nose pod causing lifting of the epidermis on the side of the nose and thereby increasing the opening of the nasal passage way.

Accordingly, the present invention may be considered an epidermal positioning mechanism having an elastic material coupled to a first end piece and a second piece. The first and second end pieces each having at least one side including an adhesive material. Preferably, but not necessarily, depending upon the application of the present invention, at least one of the end pieces would be the anchoring structure or mechanism while the other end piece acts as a lifting end piece.

Additionally the present invention need not solely be used as a nasal dilator but, as previously noted, may also be used as an epidermal positioning system for treatments of wounds and incisions by either keeping the wound or incision open for the purpose of medical treatment such as surgical procedures or cleansing of the wound or incision or by positioning the ends of the wound together in close proximity to aid in suturing of a wound or simply to be used as a suture mechanism in and of itself to hold the ends of a wound together or to hold the ends of an incision together.

Further, when the device of the present invention is used over a wound it may also have application as a bandage. For example, the elastic or resilient material will have at least one side positioned over and adjacent the wound or incision area. This side positioned over or adjacent the wound or incision area may have a medicinal material applied thereto. This medicinal material may be, for example, zinc chromate or an alginate like calcium or sodium alginate; each of those materials respectively having anti-bacterial and clot enhancing capabilities. Other medicinal materials or even non-medicinal materials could also be applied using the device of the present invention depending upon the goals and results desired of the particular user.

If the epidermal positioning mechanism of the present invention is used as a bandage it should be noted that a bandage structure could be combined with the present invention such that the bandage structure would have at least a first end and second end and elastic material would be coupled to the first end and to the second end with an anchoring structure coupled to a portion of the elastic material as well. This would provide at least two anchor points at the ends of the resilient elastic material not coupled to the bandage structure. In this manner one of the anchor structures could be adhered to the skin at a predetermined position and the bandage structure positioned over the wound or incision by stretching the resilient or elastic material and then applying the other anchor structure could be to the skin at another predetermined position. In this manner, the elastic material will contract and this will have the effect of forcing the bandage material into more positive contact with the wound and thereby enhance the effectiveness of the bandaged material. If desired a medicinal compound could be applied to the surface of the bandage material which is adjacent to the surface of the wound or incision. Additionally, the bandage material may be comprised of a hydrophilic material.

The anchoring structure in such a use would of course comprise at least two end pieces coupled to the elastic material at predetermined positions and the end pieces would include an adhesive material attached to a side of the anchoring end pieces adjacent to the epidermis or skin to which they are to be attached. The bandage structure could also have a medicinal material applied to it as previously noted with respect to the elastic material. The adhesive material may extend as an adhesive layer coextensive a side of the anchoring end pieces, or alternatively, may extend over a predetermined portion of a side of an anchoring end piece. As discussed with regard to a previous embodiment, a coextensive, overlaying barrier layer composed of a non-adhesive material may be provided. The non-adhesive overlaying barrier layer is preferably located between a portion of the adhesive material and end piece material.

Additionally, the mechanism of the present invention could be described as epidermal lifting mechanism having anchor/lifting portions, connected via an elastic or stretchable material, and include an adhesive surface. The anchor/lifting portions being such that each portion, depending upon where it is applied, may act as either an anchor portion or a lifting portion. The anchor/lifting portions having a plurality of incisions or cuts of predetermined shape which divide each anchor/lifting portion into a plurality of adhesive areas. This division of the anchor/lifting portion into a plurality of adhesive areas allows the anchor/lifting portion adhesive areas to be divided such that after a first anchor/lifting portion is applied to the desired epidermal location a first predetermined portion of that first anchor/lifting mechanism may be peeled away and leave a second predetermined portion, having a predetermined shape due to the plurality of cuts or incisions, in place on the epidermal location. Subsequently, a second anchor/lifting portion, connected to the first anchor/lifting portion via the elastic material, may be applied to a second predetermined or desired epidermal location so that the elastic material is stretched a desired amount. The second anchor/lifting portion, if it is substantially similar to the first anchor/lifting portion may be applied to the epidermis so that it may be peeled away and leave a second predetermined portion, having a predetermined shape due to the plurality of cuts or incisions, in place on the epidermal location. Accordingly, the first and second anchor/lifting portions may act as a separate anchor point and lifting point or as separate anchor points or as separate lifting points and the elastic material may simply be used to supply tension between the points or it may be used to apply a material such as a medicine to the epidermis located between the two points or it may be used to supply tension and apply a material between the two points, etc.

It is to be understood that it is within the scope of this invention to provide hook and loop type fastening means for the devices described. The hook and loop type fastener means may be used in combination with adhesive or as the sole means of applying a device to a limb, by way of example.

Further, the present invention may be described as a method for using a dressing mechanism where the dressing mechanism comprises a first section, a second section, and a third section; the first section being coupled to the second section and the second section being coupled to the third section; the first section and the third section comprising an elastic material; the first section and the third section each having a first side; and a predetermined portion of the first side including an adhesive located thereon. The method consequently comprising: First, applying the first section to a first predetermined location on an epidermis. Second, pulling the third section toward a second predetermined location on the epidermis. Third, applying the third section to the second predetermined location on the epidermis.

Alternatively, the method could be described as a method for using a dressing comprising a plurality of anchor structures, a treatment section, and an elastic material. The elastic material extending from the anchoring structure to the treatment section. The elastic material being coupled to at least one anchoring structure at a first coupling section and to the treatment section at a second coupling section. The method comprising the steps of positioning the treatment section over a first predetermined area of an epidermis; applying at least one anchor structure to a second predetermined area of the epidermis; and applying at one other anchor structure to a third predetermined area of the epidermis.

DESCRIPTION OF THE DRAWINGS

FIG. 7 is a bottom plan view of the epidermal lifting mechanism.

FIG. 8 is a side elevational view depicting the primary layers of the epidermal lifting mechanism.

FIG. 15 is a side elevational view showing the epidermal lifting mechanism properly positioned on the bridge of the nose.

FIG. 16 is a side elevational view showing the epidermal lifting mechanism improperly positioned too high on the bridge of the nose.

FIG. 17 is a side elevational view showing the epidermal lifting mechanism improperly positioned too low on the bridge of the nose.

FIG. 26 is a side elevational view showing the embodiment of either FIG. 21 or FIG. 19 being used on persons nose as a nasal dilator to enhance breathing. The embodiment of FIG. 19 is believed to be preferable to the embodiment of FIG. 21 for this purpose although either could be used.

FIG. 27 is a perspective view generally showing a human nose.

FIG. 31 is a top plan view of another alternative embodiment of the proposed invention.

FIG. 32 is a top plan view of an additional proposed embodiment of the present invention shown as the embodiment would be manufactured and illustrating the area that is removed to expose the adhesive and then bent backwards and applied as shown in FIG. 33.

FIG. 33 is a top plan view of the embodiment shown in FIG. 32 applied to an epidermal surface and illustrating the shear point, the adhesive, and the elastic or stretchable material.

FIG. 34 is a top plan view of an alternative structure to the embodiment illustrated in FIG. 19.

FIG. 77 is a cross-sectional view from line 77-77 of FIG. 84.

FIG. 78 is a cross-sectional view from line 78-78 of FIG. 86.

FIG. 79 is a cross-sectional view from line 79-79 of FIG. 86.

FIG. 80 is a cross-sectional view of a structure similar to the structure disclosed in FIG. 86 illustrating the use of input and output ports which may be used to irrigate a wound or deliver medicine to a predetermined area.

FIG. 81 is a view taken from line 81-81 of FIG. 39.

FIG. 82 is a view taken from line 82-82 of FIG. 40

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The invention comprises an epidermal lifting mechanism for providing a lifting force to a predetermined epidermal area, such as the bridge of the nose, to provide an increased flow rate of gas through the nasal passage and will be referred to generally as 10 in the following detailed description.

Figure 1:
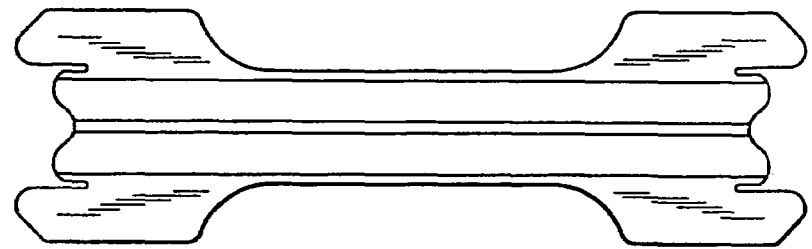
FIG. 1 is a top plan view of a prior art nasal strip.
Figure 1A:
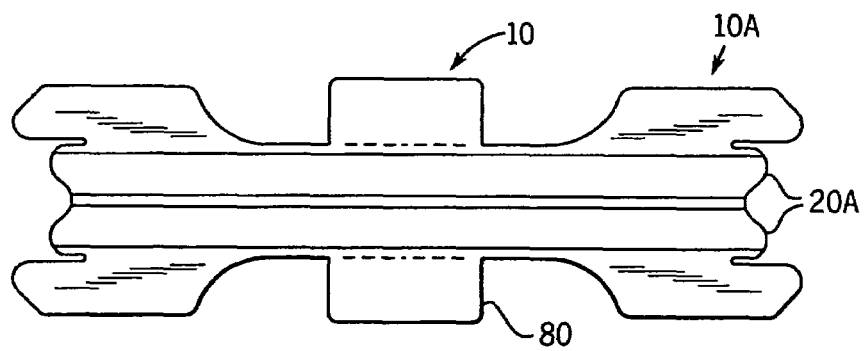
FIG. 1A is a top plan view of the prior art nasal strip of FIG. 1 including the flaps of the present invention.

Referring to FIGS. 1 and 1A, a prior art device is shown. The prior art device shown in FIG. 1 is currently marketed by CNS, Inc. of Chanhassen, Minn. and sold under the trademark BREATHE RIGHT. The same device is shown in FIG. 1A, however the device in FIG. 1A includes the flaps of the present invention whose structure and advantages are discussed in detail below.

Figure 2:
FIG. 2 is a side elevational view of a relaxed multi-level spring.

The present invention, indicated generally by the reference numeral 10, includes a two part multi-level leaf spring 20 as shown in FIG. 2. The two part multi-level leaf spring 20 comprises a pair of spring laminates 22 and 24. Each spring laminate 22 and 24 is manufactured from a 2 mil to 8 mil polyester film laminated to a spun bonded polyester material. The spun bonded polyester material may or may not be coated with a pressure sensitive adhesive. The spring laminates 22 and 24 are laminated together.

Figure 3:
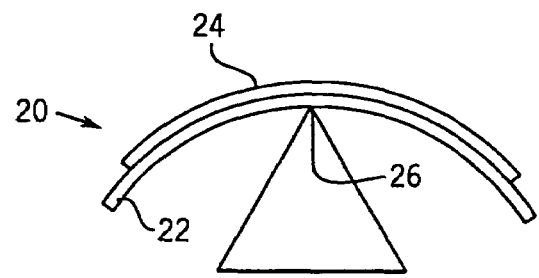
FIG. 3 is a side elevational view of a tensioned multi-leveled spring bent over a fulcrum point.

As illustrated in FIG. 3, when the top 24 and bottom 22 spring laminates are laminated together and the invention 10 is applied to the bridge of the nose, represented by the fulcrum point 26, the bending of the multi-level spring 20 increases the opening force to the nasal passages over a single level spring.

Adding a layer of spring material 24 on top of another layer 22 of spring material creates a leaf spring action. Because there is a stretching force introduced into the top layer 24 when bent over a fulcrum point, a stronger (compound) spring action is created as compared to a single layer spring of equal thickness. Furthermore, bending over a fulcrum point creates a stronger yet spring-action.

Figure 4:
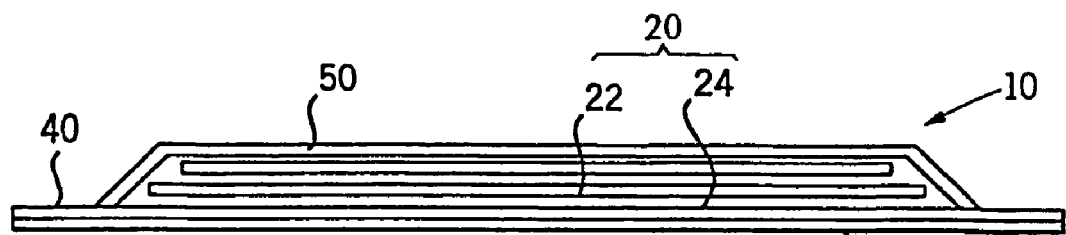
FIG. 4 is a side elevational view of the epidermal lifting mechanism showing its layered components.
Figure 18:
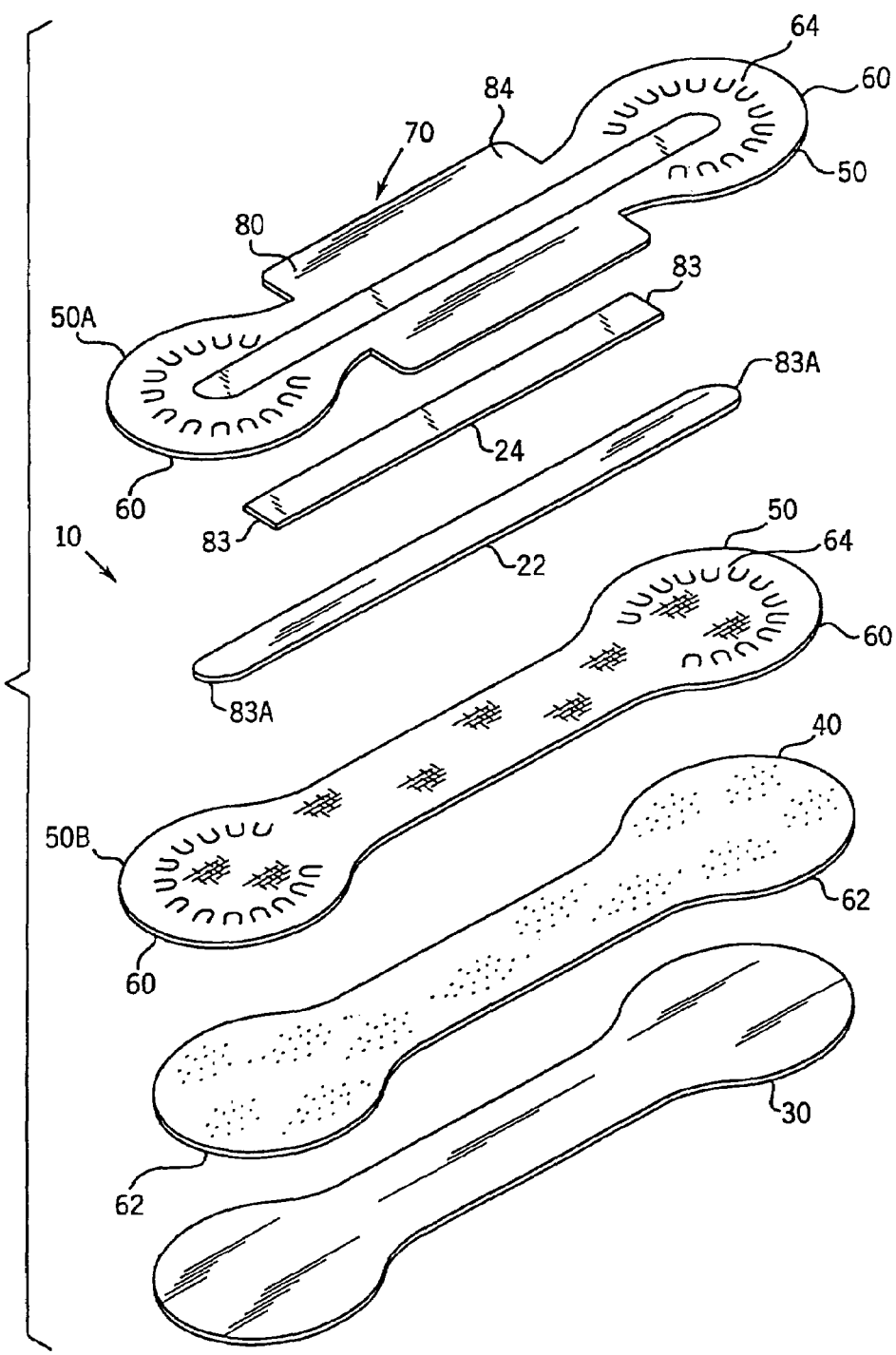
FIG. 18 is an exploded view of the preferred embodiment of the present invention.

Now referring to FIGS. 4 and 18, the material layers of the invention 10 include a silicone coated release liner 30, an adhesive system 40 to adhere the epidermal lifting mechanism 10 to the nose, a top layer of material 50, and the two part spring laminate 20. The top layer 50 is composed of two layers of material 50A and 50B and contains the springs 24 and 22 there between, as shown in FIG. 18. The release liner 30 is removed prior to placing the mechanism 10 on the bridge of the nose. The adhesive system 40 can either be a pressure sensitive hypo-allergenic acrylic or a hydrocolloid system. The top layer of material 50 can be either a non-woven material or a material with some stretch characteristics such as a 3 mil polyurethane film.

The preferred embodiment of the invention 10 is shown in FIG. 7. Although unitary in construction, it has the following components: a pair of pods 60 and a bridge section 70. The pods 60 include an exposed adhesive surface 62 which is bonded to the skin on the sides of the nose. The pod 60 configurations allow for flexibility of the bottom spring 22 to conform to the irregular surfaces of the nose. The bridge section 70 of the device has at least one fulcrum point as shown in FIG. 3 and lies across the bridge of the nose as shown in FIG. 15.

Figure 5:
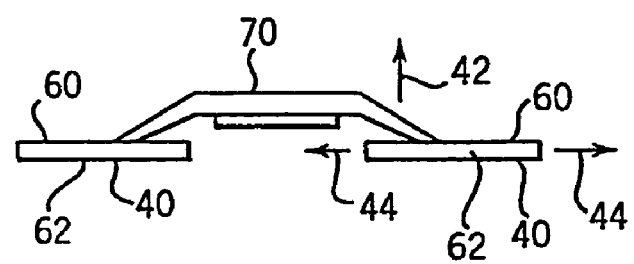
FIG. 5 is a schematic side elevational view of the epidermal lifting mechanism wherein the arrows depict the sheer force and peeling forces.
Figure 6:
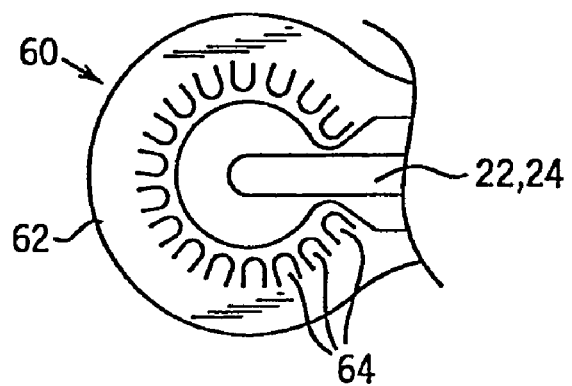
FIG. 6 is a top plan view of an end portion of the epidermal lifting mechanism.

As shown in FIG. 6, the pods 60 include horseshoe shaped cuts or incisions 64 in the top layer of material 50 through the adhesive layer 40 which, when applied to the nose, allows the spring action to generate a uniform lifting force in a suction cuplike manner while at the same time applies a shearing force to the adhesive itself rather than a peeling force thereby creating flexibility from the lift point to the adhesion point. This principle is demonstrated in FIG. 5. By decreasing the peel force 42 on the adhesive 40 the bond between the adhesive 40 and the skin is greatly increased and allows more flexibility of the epidermal lifting mechanism 10 during facial movement. The shearing forces are shown at 44.

Referring back to FIG. 7, the present invention 10 may be further improved by including a pair of flaps 80 which are attached adjacent to the bridge section 70 of the invention 10. The flaps 80, when folded underneath or over the adhesive layer 40 of the bridge section 70, create another pair of fulcrum points along lines 82 between the bridge of the nose (fulcrum point 2) and the pods 60 when the invention 10 is applied to the wearer's nose. Thus, the flaps 80, when folded, function to increase the dilation force to the outer epidermis of the nasal passages.

More specifically, the additional fulcrum points 82 are accomplished by folding the flaps 80 underneath the bridge section 70 thereby allowing the adhesive area of each flap 84 to adhere to the bottom of the bridge section 70 thus securing it in place. The flaps 80 further include perforations 86 for ease of folding.

As discussed above, the pair of flaps 80 adds fulcrum points. Accordingly, when the flaps 80 are folded they form end sections along lines 82 which will be located to either side of the bridge of the nose. Each of the end sections along lines 82 will act as a fulcrum point in addition to the bridge of the nose thereby increasing the number of fulcrum points and the mechanical lifting ability of the present invention. Further, when folded they provide a cushioned area for the bridge of the nose and cover the adhesive 40 on the underside of the bridge section 70 so when applied for several hours and then removed, discomfort to the skin tissue on the bridge of the nose is greatly reduced or eliminated since no adhesive has been in contact with the bridge of the nose due to the barrier created by the flaps.

The material layers of the invention 10 are shown in FIG. 8. Again, the layers include a silicone coated release liner 30, an adhesive system 40 to adhere the epidermal lifting mechanism 10 to the nose, a first spring laminate 22, a second spring laminate 24, and a top layer of material 50.

Figure 9:
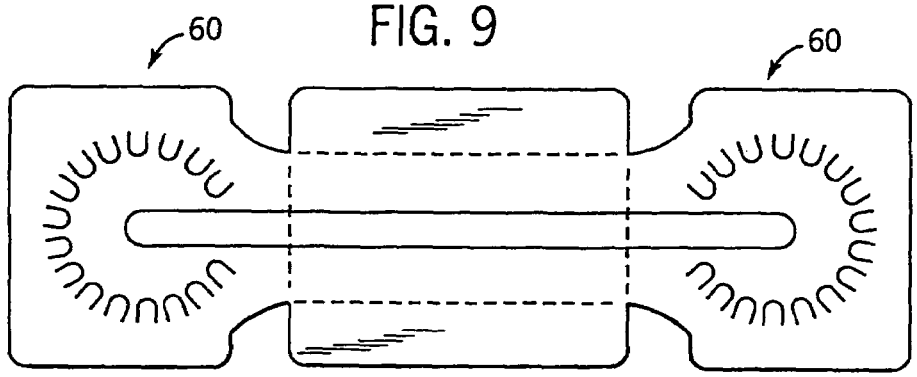
FIG. 9 is a top plan view of an alternative embodiment of the epidermal lifting mechanism.
Figure 10:
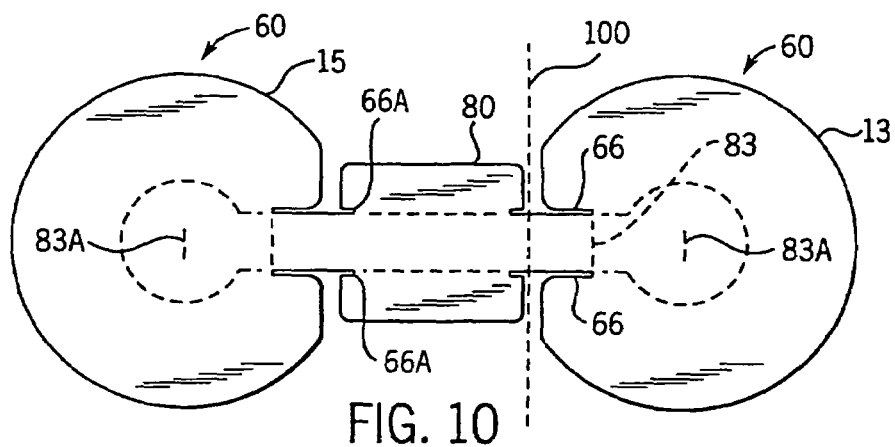
FIG. 10 is a top plan view of an alternative embodiment of the epidermal lifting mechanism.

Alternative embodiments of the invention 10 are shown in FIGS. 9 through 14. In FIG. 9, the shape of the pods 60 is shown to be rectangular instead of round. In FIG. 10, the horseshoe shaped cuts or incisions 64 have been removed and additional slits 66 and 66A have been added. In this embodiment, when the flaps 80 are not folded over, slits 66A mechanically adjust the peeling action to a shear action thereby allowing greater adhesion over the predetermined epidermal area. Additionally, in this embodiment a cut could be made along line 100 to divide the invention 10 into sections 13 and 15 whereby section 13 could be discarded and section 15 could be used as a dilator for only one side of a person's nose.

Figure 11:
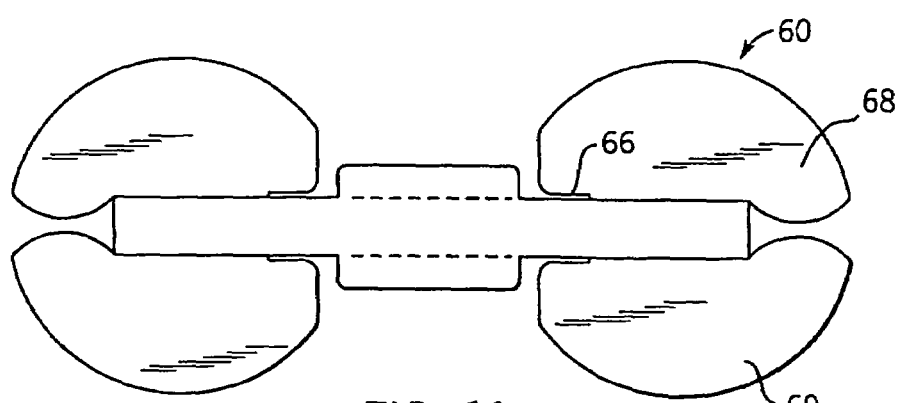
FIG. 11 is a top plan view of an alternative embodiment of the epidermal lifting mechanism.

The embodiment shown in FIG. 11 includes slits 66 and further includes a two-part pod 60. Pod 60 comprises an upper pod half 68 and a lower pod half 69. Pod halves 68 and 69 and slits 66 allow for greater flexibility of the pod 60 on the nose of the wearer.

Figure 12:
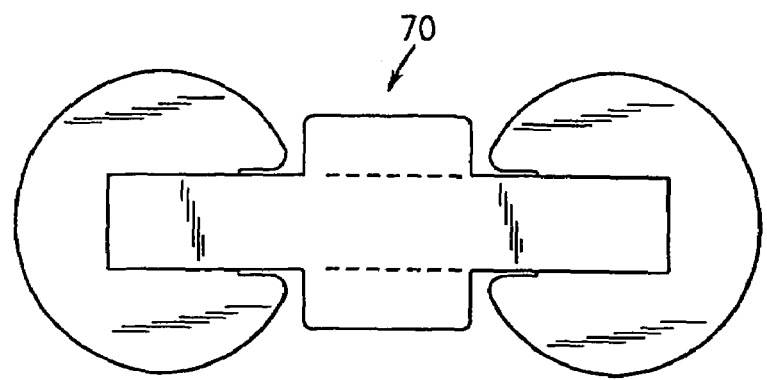
FIG. 12 is a top plan view of an alternative embodiment of the epidermal lifting mechanism.
Figure 13:
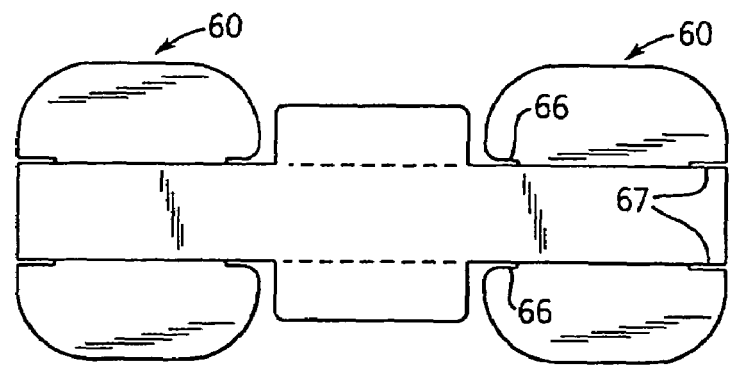
FIG. 13 is a top plan view of an alternative embodiment of the epidermal lifting mechanism.

The embodiment shown in FIG. 12 is similar to that shown in FIG. 10 with the exception that the bridge section 70 has been widened. The embodiment of FIG. 13 includes the wider bridge section 70 in combination with rectangular pods 60. Additional slits 67 have also been added near the outer sides of the pods 60. Slits 67 change the direction of the force applied to the pods 60 so that instead of a peel force (a force which tends to peel away the pods 60 from the epidermis to which they are applied) to a sheer forces (a force which tends to drag the pods 60 across the epidermis to which they are applied).

Figure 14:
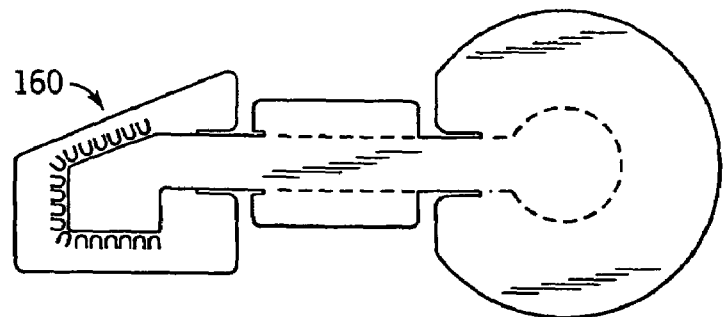
FIG. 14 is a top plan view of an alternative embodiment of the epidermal lifting mechanism.

The embodiment depicted in FIG. 14 demonstrates the principal that different pod 60 configurations can be used on the same epidermal lifting mechanism 10. The pod 60 shown on the left side has a sloping side to allow for better adhesion to the side of the nose.

The application of the invention 10 to the nose of the wearer is shown in FIGS. 15 through 17. Preferred installation of the epidermal lifting mechanism 10 on the bridge of the nose is shown in FIG. 15 while in FIG. 16, the epidermal lifting mechanism 10 is applied too high on the nose and is applied too low in FIG. 17. However, while the positions shown in FIGS. 16 and 17 are not preferred they are functional since the structure of the present invention 10 allows a user the ability to apply the invention 10 over a relatively large epidermal area and thus effectiveness of the present invention is greatly enhanced. The present invention will generally work effectively in all the positions shown in FIGS. 15-17.

Alternatively, this invention 10 may be described as a method for increasing the flow rate of gas through the nasal passages, the method comprising the steps of removing the release liner 30, and positioning the invention 10 as shown in FIG. 15 or as shown in FIGS. 16 and 17, depending upon the comfort of the wearer.

Figure 19:
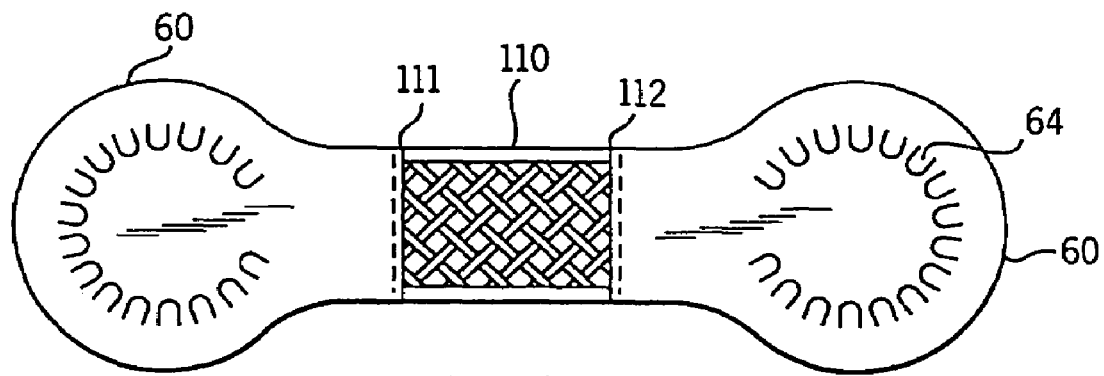
FIG. 19 is a top plan view of an alternative embodiment of the present invention including an elastic strip.

Referring now to FIG. 19, a top plan view of an alternative embodiment of the present invention 10 may be seen to comprise an elastic midsection 110 having ends 111 and 112. Ends 111 and 112 are coupled to pod sections 60. This embodiment does not include any spring mechanism other than the elastic section 110; the elastic section 110 taking the place of the spring mechanism. The resiliency of the elastic section 110 will cause the two nasal pods 60 to be drawn together when the elastic member contracts. If this is done over a fulcrum point such as the bridge of the nose it will cause a lifting of the nasal passages and thus may be used as a nasal dilator as illustrated in FIG. 26.

Figure 24:
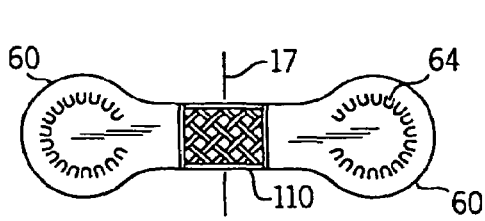
FIG. 24 top plan view which illustrates the embodiment of FIG. 19 in use to keep an incision closed.
Figure 25:
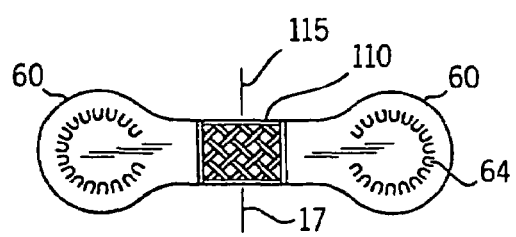
FIG. 25 top plan view which illustrates the embodiment FIG. 19 in use to keep an incision closed with the ends of the incision kept in proper alignment to add in suturing the incision.

Additionally the mechanism of FIG. 19 may be used as shown in FIGS. 24 and 25 to aid in holding a wound or incision 17 closed either for the purposes of healing as illustrated in FIG. 24 or for the purpose of aiding in suturing as illustrated in FIG. 25. The pods 60 adhering to the epidermis to either side of the wound and the elastic member 110 being stretched across the wound so that it will contract and draw the two pods 60 towards each other thereby closing the wound in an effective manner. Additionally, when the wound is closed in this manner a surgeon or physician may have both hands free to apply sutures 115 along the wound or incision 17. This is believed particularly helpful when dealing with a large wound or incision.

With respect to the embodiment of the invention shown in FIG. 19 it should be noted that U shaped cuts or incisions 64 are also illustrated. Again, these cuts or incisions may be of any shape although the U, or horseshoe shape is preferred, however the embodiment disclosed in FIG. 19 could function with these U, or horseshoe shaped cuts or incisions 64.

Figure 20:
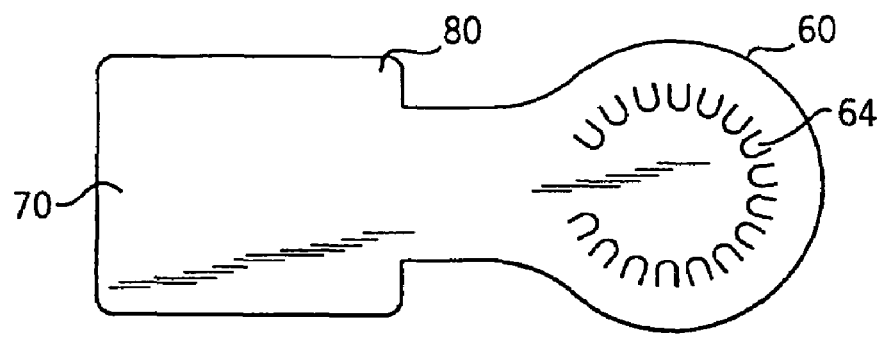
FIG. 20 is a top plan view of an alternative embodiment of the present invention showing an embodiment having application for only one side of a persons nose or for raising a predetermined portion of an epidermal layer.

Referring now to FIG. 20 an alternative embodiment of the present invention for use as a nasal dilator is shown. In this embodiment the spring sections are included as shown in FIG. 18 although they are not shown in FIG. 20. This embodiment functions in a manner similar to the embodiment FIG. 10 and is simply meant to illustrate once again that the nasal dilator of the present invention could be applied to only one side of a person's nose 19.

Figure 21:
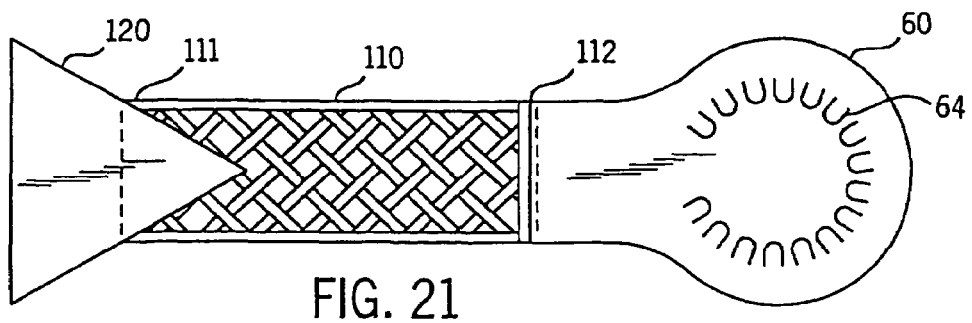
FIG. 21 is a top plan view of an alternative embodiment of the present invention showing the elastic member having a first end coupled to a pod and a second end coupled to an anchor mechanism for application to a selected area of a person or animal epidermis. For example, the anchor mechanism could be applied to a person's cheek and the pod applied to the epidermis of a persons nose to enhance opening of the nasal passage.

Referring now to FIG. 21 another alternative embodiment of the present invention is shown in a top plan view illustrating the elastic member 110 coupled at its end 112 to pod 60 and coupled at its end 111 to an anchor 120. The anchor 120 has an adhesive layer applied to it in the same manner as the adhesive layer which is applied to the pod 60. The embodiment of the invention 10 shown in FIG. 21 has application for maintaining an incision opening or wound opening for either a surgical procedure or cleansing purposes as illustrated in FIG. 23 or for use as a nasal dilator for application to only side of a person's nose as illustrated in FIG. 22.

Figure 22:
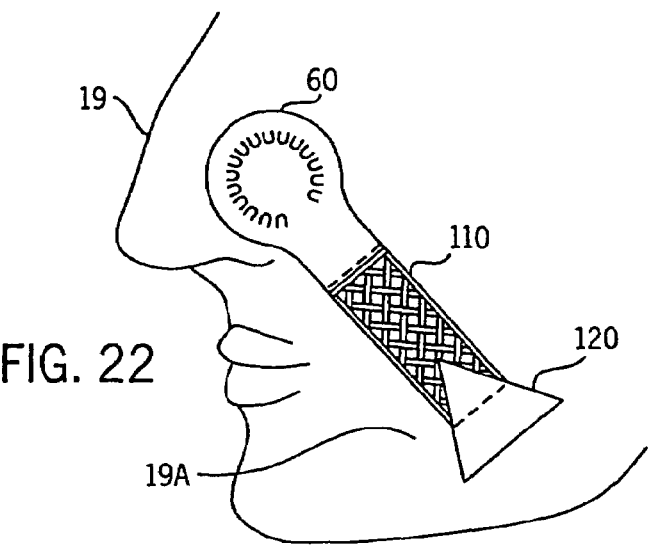
FIG. 22 is a side elevational view illustrating embodiment of FIG. 21 with the anchor mechanism applied to a person's cheek and the pod applied to a side of a persons nose.

Referring to FIG. 22 pod 60 may be seen applied to the side of a persons nose 19 and elastic member 110 is stretched so that anchor 120 may be applied to the side of persons face 19A. Thus, elastic member 110 will contract and pull pod 60 and anchor 120 toward one another but since anchor 120 is positioned on a substantially stationary epidermal area of the person's face the majority of the movement will occur at pod 60 causing the epidermal area to which it is applied to be pulled outward and thus open the nasal passage.

Figure 23:
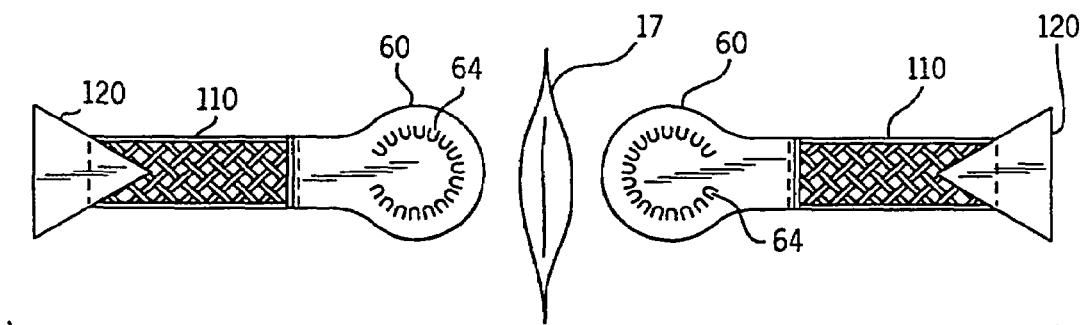
FIG. 23 top plan view which illustrates the embodiment of FIG. 21 in use to hold an incision open.

Referring to FIG. 23, the incision 17 may be seen to be held open by the action of the embodiment disclosed in FIG. 21. The anchors 120 are applied to a substantially stationary epidermal area and the elastic members 110 are stretched and the pods 60 are positioned to either side of the wound or incision to hold it open so that the wound may be cleansed or a surgical procedure may be performed through the incision thus freeing the physician's hands for this purpose.

It should be noted that the U shaped cuts 64 are disclosed in the embodiment of the present invention 10 shown in FIG. 21. While these U shaped cuts are preferred they are not considered necessary to practice the present invention.

Figure 28:
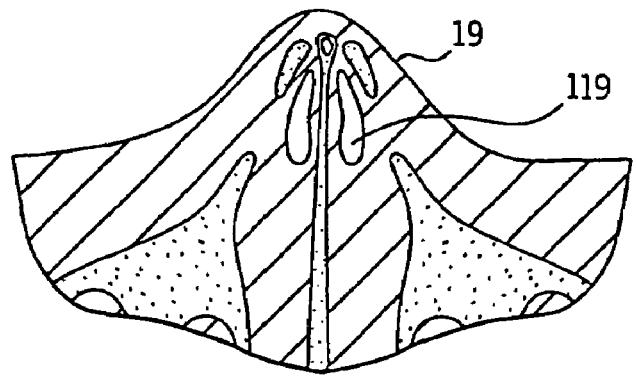
FIG. 28 is a cross sectional view of the nose in FIG. 27 with the nose shown absent any nasal dilator.
Figure 29:
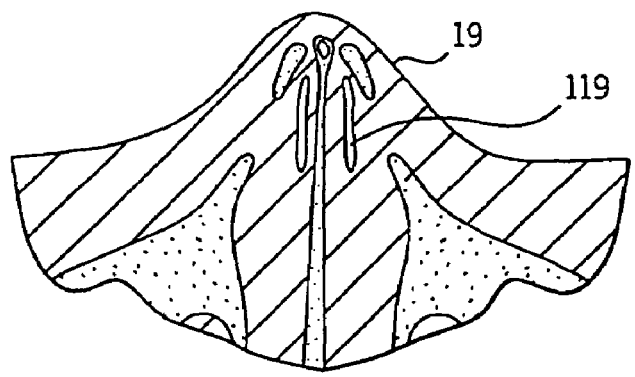
FIG. 29 is a cross sectional view of the nose in FIG. 27 with the nose shown being in a state of relatively little air flow through the nasal passages.
Figure 30:
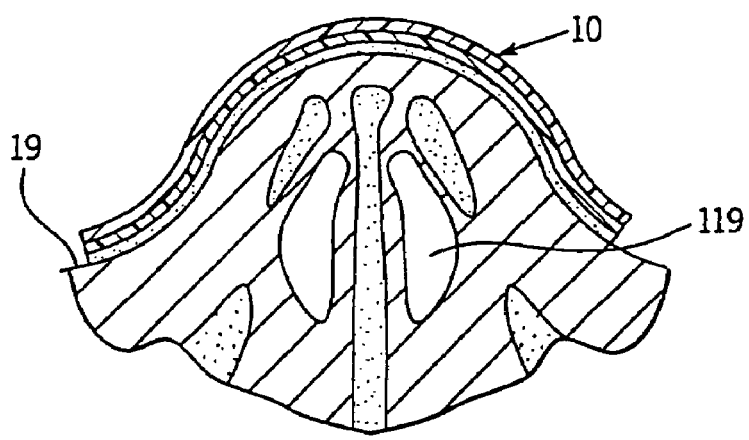
FIG. 30 is a cross sectional view of the nose in FIG. 27 with a nasal dilator of the present invention applied illustrating an appreciable air flow through the nasal passages.

Referring now to FIGS. 28, 29 and 30, FIG. 28 shows the nose 19 and the nasal passages 119 in cross sectional view. The nasal passages in FIG. 28 being shown open but absent the use of any nasal dilator. In FIG. 29 the same cross sectional view is shown but the nose 19 and in particular the nasal passages 119 are shown being in a state of relatively little airflow through the nasal passages 119. FIG. 30 illustrates a cross sectional view using a nasal dilator of the present invention 10 wherein the nasal passages 119 of the nose 19 are held substantially open for airflow through the nasal passages 119.

Clearly, the alternative embodiments shown in FIGS. 19 and 21 could also be practiced according to the methods previously disclosed. Specifically, the embodiment of FIG. 19 could be practiced as a method using the structure previously described wherein the embodiment disclosed in FIG. 19 is applied by first applying one nose pod section 60 to one side of a wound 17 and stretching the elastic member 110 over the wound 17 and then applying the nose pod section 60 to the other side or opposite side of the wound or incision 17 whereby the wound or incision 17 is held closed. Additionally, it should be noted that a medicinal material could be applied to the elastic member 110 over the portion of its surface which would be adjacent to the wound or incision 17 and thus aid in healing of the wound. Medicinal materials such as zinc chromate or calcium alginate or sodium alginate are possible such compounds.

Alternatively, the embodiment of FIG. 21 could be used in a method wherein the pod 60 is applied to an epidermal area which is desired to be pulled or raised. This epidermal area could be an area immediately adjacent an incision or wound 17 or the side epidermis of a person's nose 19. The elastic member 110 being stretched and the anchor portion 120 being applied with its adhesive side to an epidermal area which is relatively stationary and the elastic material 110 contracting and thereby raising or pulling or lifting the skin to which the pod 60 has been attached to via its adhesive side.

Alternatively, as illustrated in FIGS. 31, 32, and 33, the mechanism of the present invention could be described as epidermal lifting mechanism having anchor/lifting portions 120, connected via an elastic or stretchable material 110, and include an adhesive surface 121. The anchor/lifting portions 120 being such that each portion 120, depending upon where it is applied, may act as either an anchor portion 120 or a lifting portion 120. The anchor/lifting portions 120 having a plurality of incisions or cuts 64 of predetermined shape, (e.g., U shaped as illustrated in FIGS. 31-33) which divide each anchor/lifting portion 120 into a plurality of adhesive areas 121a and 121b. This division of the anchor/lifting portion 120 into a plurality of adhesive areas 121 allows the anchor/lifting portion adhesive areas 121 to be divided such that after a first anchor/lifting portion 123 is applied to the desired epidermal location a first predetermined portion 121c of that first anchor/lifting portion 120 may be peeled away and leave a second predetermined portion 121d, having a predetermined shape due to the plurality of cuts or incisions 64, in place on the epidermal location. Subsequently, a second anchor/lifting portion 125, connected to the first anchor/lifting portion 123 via the elastic material 110, may be applied to a second predetermined or desired epidermal location so that the elastic material 110 is stretched a desired amount. The second anchor/lifting portion 125, if it is substantially similar to the first anchor/lifting portion 123 may be applied to the epidermis so that it may be peeled away and leave a second predetermined portion 121d, having a predetermined shape due to the plurality of cuts or incisions 64, in place on the epidermal location. Accordingly, the first and second anchor/lifting portions 123 and 125 may act as a separate anchor point and lifting point or as separate anchor points or as separate lifting points and the elastic material 110 may simply be used to supply tension between the points 123 and 125 or it may be used to apply a material such as a medicine to the epidermis located between the two points or it may be used to supply tension and apply a material between the two points, etc. The purpose of this alternative embodiment to take advantage of the multiple shear points 200 created using this design to enhance the adhesion of this embodiment to the desired epidermal location so that the anchor/lifting portions 120 maintain proper adhesion at their desired locations.

Figure 35:
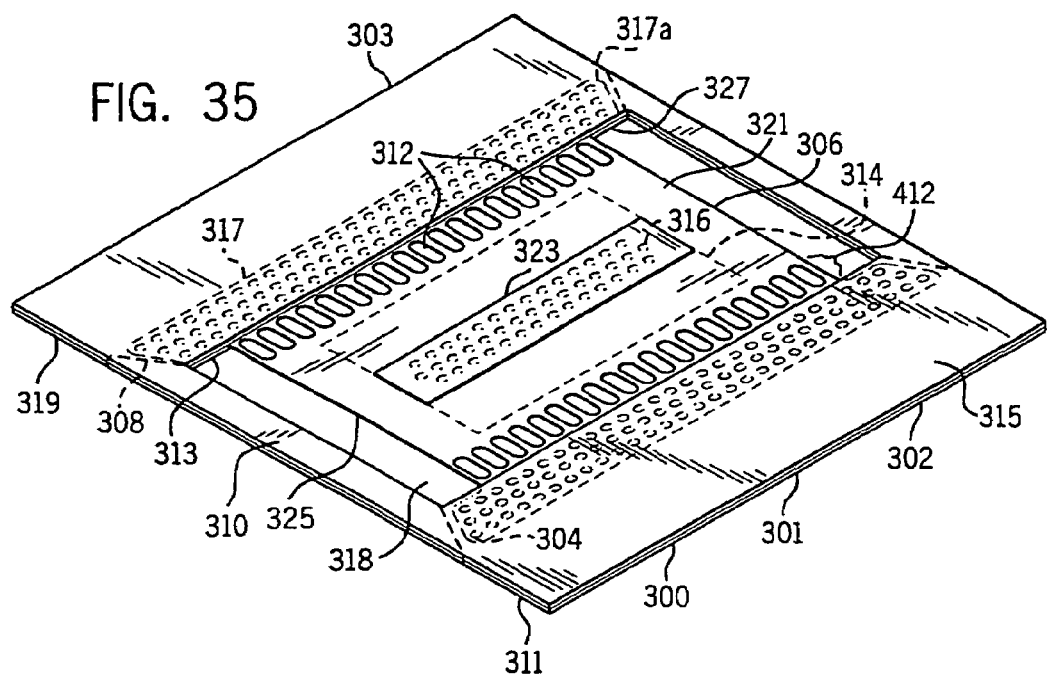
FIG. 35 is a perspective view of an another alternative structure of the present invention.
Figure 36:
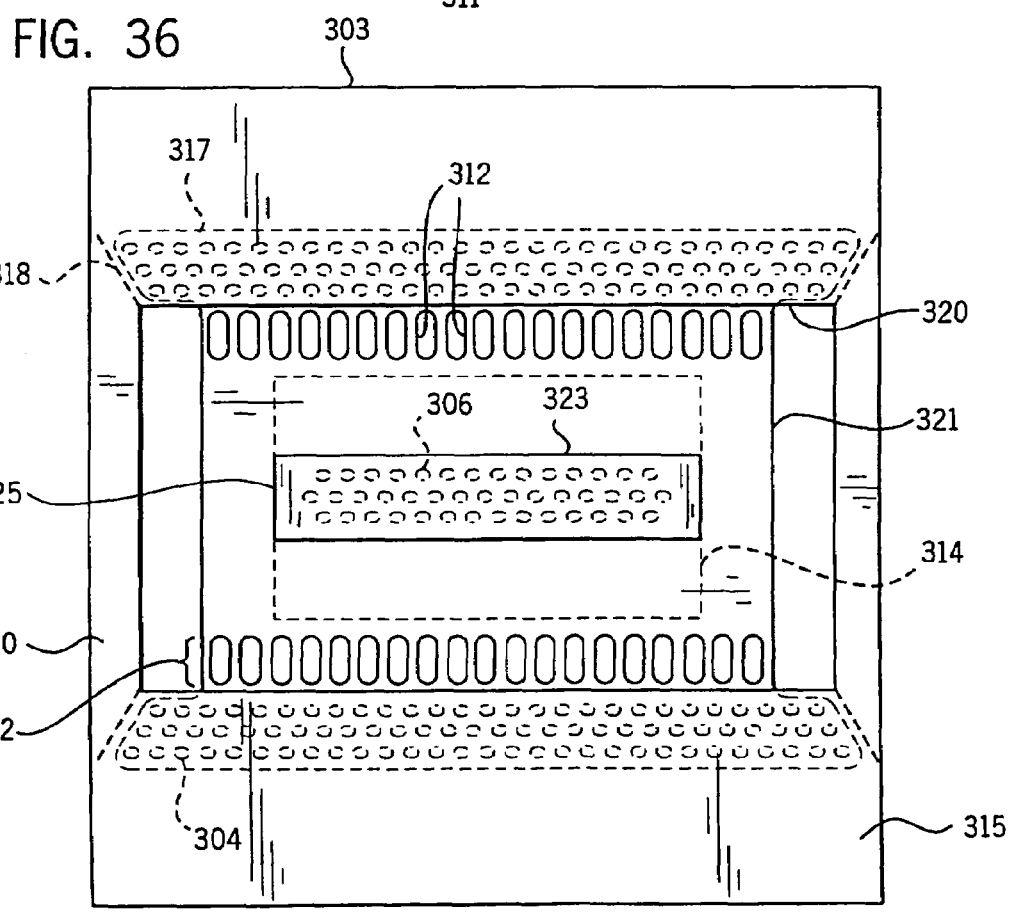
FIG. 36 is a top plan view of the embodiment disclosed in FIG. 35.

Referring now to FIGS. 35 and 36 another alternative embodiment of the present invention may be observed. The dressing structure 300 is comprised of a multiple layer or laminated material 302 at its anchor sections 301 and 303 and a latex rubber 321 at its center section 325. The laminated material includes a top surface 315 made of TYVEC brand material and a bottom surface 319 also made of the same material but coated with a hypo-allergenic acrylic adhesive 327 and covered with a silicone release liner. The anchor sections 301 and 303 have an adhesive bottom layer 311 for adhering to an epidermis 11. The laminated material 302 has a channel or slit 313 into which margins 317 of the latex rubber 321 are engaged. The margins 317 include openings 304 and the channel 313 includes the adhesive 327 which extends through the openings 304 from the bottom 319 to the top 315. This creates a series of adhesive openings 304 which act as plugs which extend through the openings 304 and couple the upper layer 315 to the lower layer 319 effectively holding the non-elastic TYVEC material together so that the latex material 321 is effectively locked into the channel 313 and cannot easily be removed by tension when stretched. Accordingly, margins 317 are secured to the anchor sections 301 and 303 at locking section 317a.

Figure 51:
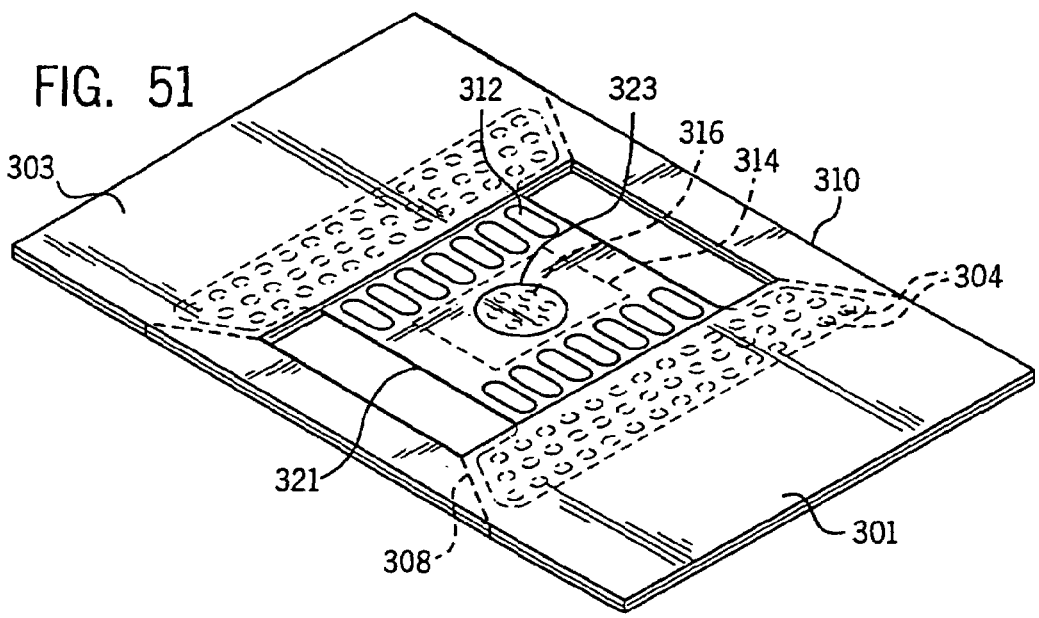
FIG. 51 is a perspective view of an another alternative structure of the present invention.
Figure 52:
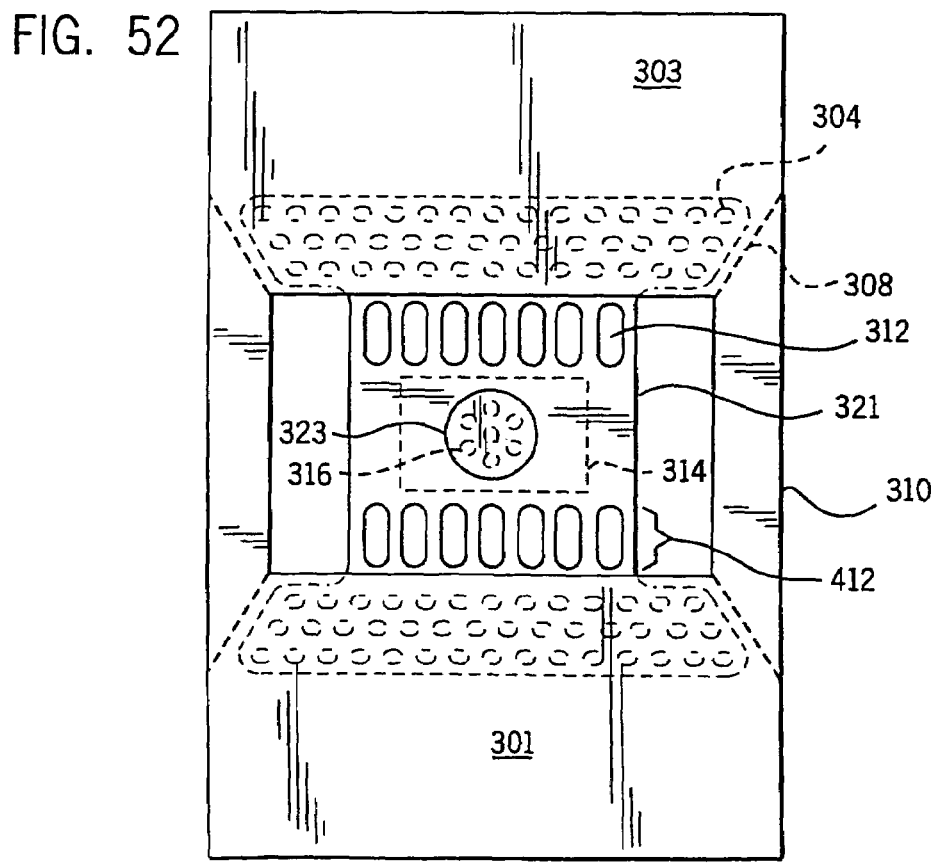
FIG. 52 is a top plan view of the structure disclosed in FIG. 51.

Still referring to FIG. 35 and FIG. 36 the center section 325 may be observed to include a TYVEC brand material stabilizing section 323 which is bonded to a gauze pad 314 via openings 316, in the latex 321 which contain adhesive 327. The adhesive 327 extending in a plug like manner from the pad 314 to the stabilizing section 323. This creates a bandage or dressing structure which is suspended by the latex 321 between the anchoring sections 301 and 303. Further, as illustrated by FIGS. 51 and 52 the shape of the TYVEC top layer 323 need not be rectangular but can be of any design, e.g., round. When this embodiment is applied over a wound or other predetermined area of the epidermis 11 the latex material 321 is stretched between the two anchoring sections 301 and 303 which causes the latex 321 to act much like a leaf spring and apply a positive pressure downward through the pad 314. Accordingly, the wound to which this device 300 is applied will have a positive pressure against it. It is well known in first aid that pressure applied to a wound will help reduce bleeding. The present invention thus provides an effective bandage which will also effectively limit bleeding from the wound. Further, the positive down pressure will effectively maintain contact of the pad 314 with the wound or other predetermined area despite movement of the surrounding epidermis 11.

Still referring to FIGS. 35 and 36 it should be noted that stability strips 310 are included to illustrate that it is presently believed that in commercial utilization of the present invention that it is believed to be desirable to provide material to keep the dressing structure 300 relatively rigid prior to use. The strips 310 are removed prior to use by tearing the material 302 along the perforations 308. The strips 310 are separated from the latex 321 by gap 318. Also, shown in FIG. 36 is curve 320 which is believed to provide strain relief when the present dressing structure 300 is applied so that even pressure is exerted across the latex 321.

Figure 37:
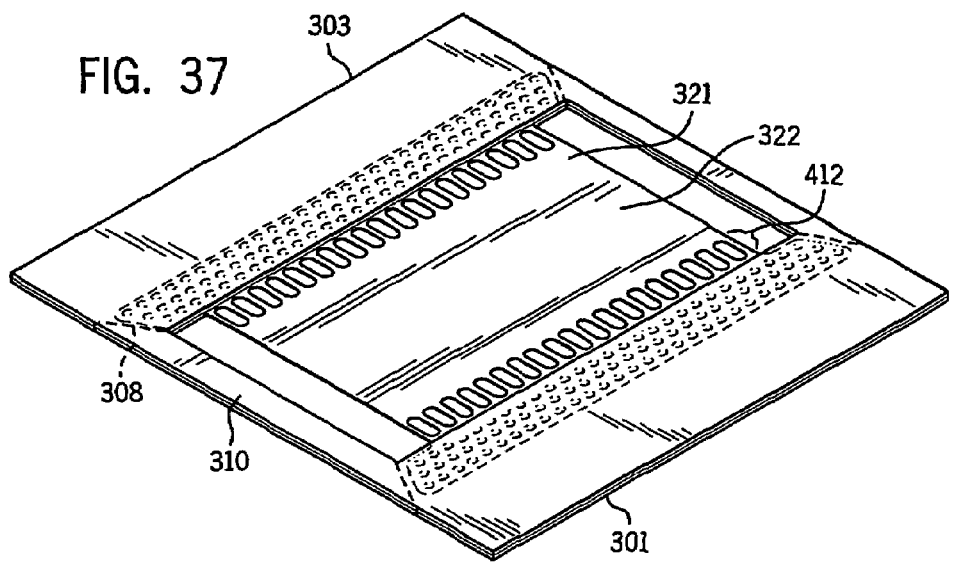
FIG. 37 is a perspective view of an another alternative structure of the present invention.
Figure 38:
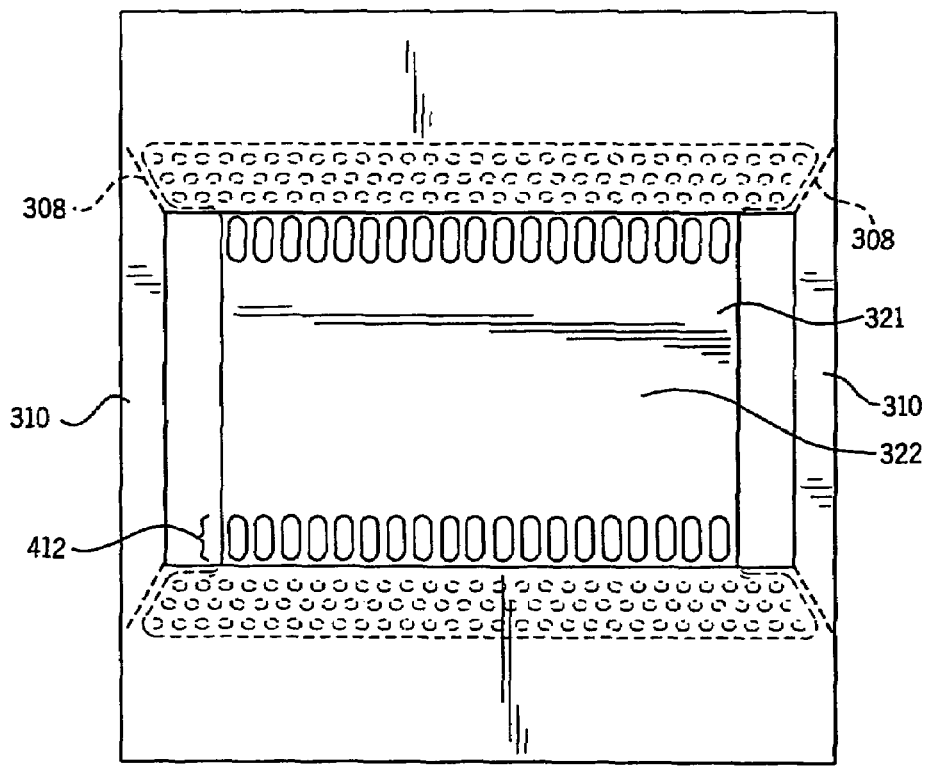
FIG. 38 is a top plan view of the embodiment disclosed in FIG. 37.

The openings 312, also shown in FIGS. 37 and 38, should also be noted. The openings 312 are located in a tension adjustment section 412 of the latex 321. Depending upon the number of openings 312 or whether they are present at all the tension applied to the latex section 321. Further, as the tension adjustment section 412 of the latex 321 is stretched to apply the dressing structure 300 the openings 312 will become distorted. The greater the stretching the greater the tension applied to the latex section 321. Consequently, a person applying the dressing structure disclosed herein may visually see the amount of tension applied to the latex section 321. This allows a person applying a dressing 300 or series of dressings 300 to apply the dressings 300 in a manner so that the pressure and exerted by the stretching of the latex 321 is kept relatively constant. Alternatively, it allows the user to apply dressings 300 which will apply a variety of pressures across the desired treatment area.

Referring to FIGS. 37 and 38 an alternative embodiment from that shown in FIGS. 35 and 36 may be seen wherein the pad 314 and inelastic material 323 are not incorporated so that only an elastic section 322 remains.

Figure 40:
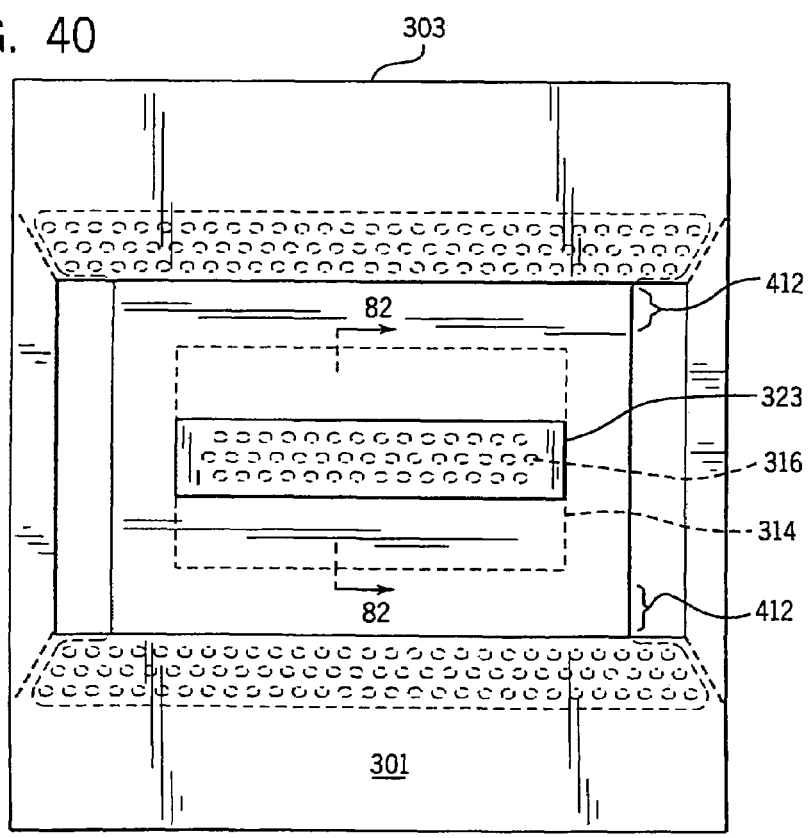
FIG. 40 is a top plan view of the embodiment disclosed in FIG. 39.
Figure 41:
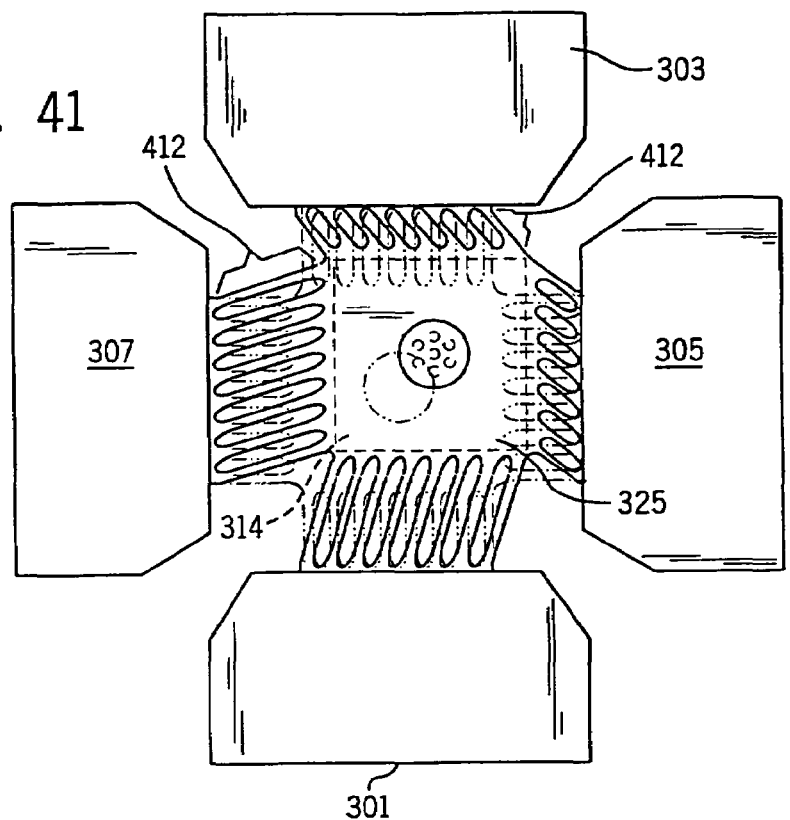
FIG. 41 is a top plan view another embodiment of the present invention illustrating an embodiment of the present invention by supper-imposing two views of the embodiment; the phantom lines showing the embodiment at rest without the latex sections being stretched and the solid lines illustrating the latex sections being stretched while the center or second section maintains position over the treatment area despite the uneven tension applied to the various anchor sections.
Figure 42:
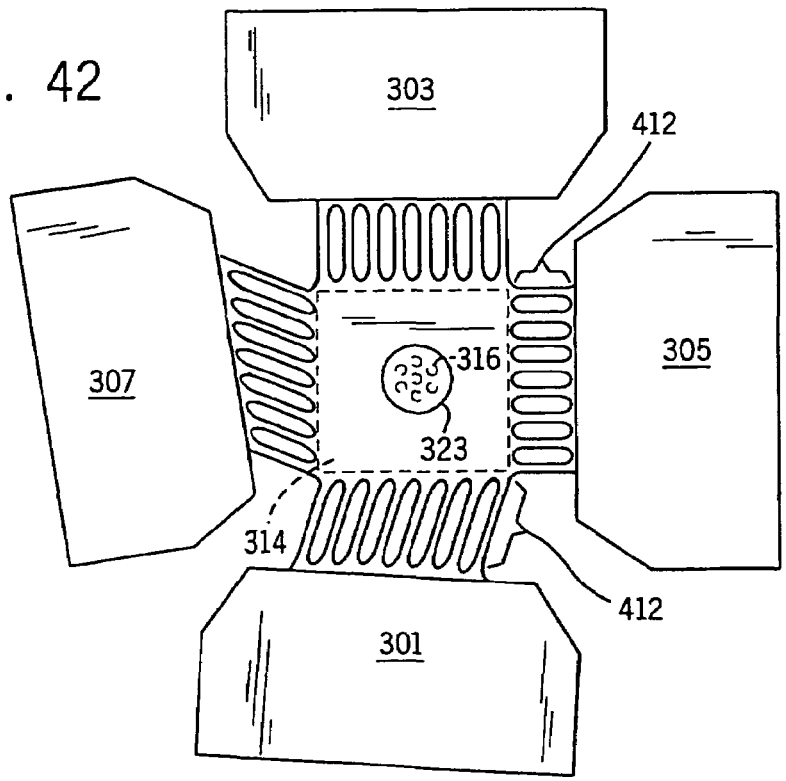
FIG. 42 is a top plan view of the embodiment shown in FIG. 41 illustrating how the second center section may be positioned and various anchoring sections positioned to adjust the stress or pressure applied at the center section.

Referring to FIGS. 41 and 42, and FIGS. 45 and 46, another alternative embodiment to the present invention is illustrated. This embodiment is substantially the same structurally as the embodiments disclosed in FIGS. 35 and 36 with the exception that two additional anchors sections 305 and 307 have been added. Also, the stabilizing section 323 is round rather than rectangular in shape. The pad 314 is coupled to the stabilizing section as previously described. FIGS. 40 and 41 illustrate that tension adjustment sections 412 need not all apply the same level of tension or be stretched equally. Further, the anchor sections 301, 303, 305, and 307 may be moved relative to each other while the center section 325 is maintained in position over the desired treatment area. Accordingly, when the present invention is applied over an area of the body that is subject to movement such as an elbow, knee, or hand the center section 325 will maintain its position over the wound or area to which it is desired to apply treatment.

Figure 39:
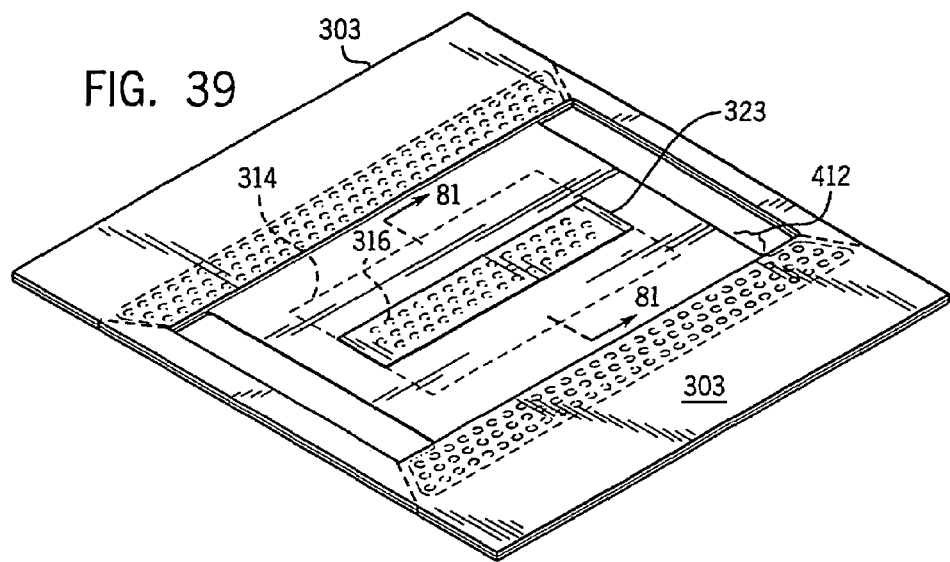
FIG. 39 is a perspective view of an another alternative structure of the present invention.

Referring to FIGS. 39 and 40 another alternative embodiment may be observed. In this alternative the openings 312 have been eliminated to illustrate that they are optional and not necessary structures to practice the present invention.

Additionally, the stabilizing section disclosed in FIG. 40 may be seen in FIG. 82 to be composed of a top layer 323 of TYVEC brand material, a layer of adhesive 327, a layer of latex 321 having openings 304, and a pad 314 to which an ointment 390 has been applied. The pad 314 being coupled to the material 323 via the adhesive 327 which extends through the openings 304 in the latex 321.

The stabilizing section disclosed in FIG. 39 may be seen in FIG. 81 to be composed of a top layer 323 of TYVEC brand material, a layer of adhesive 327, a layer of latex 321 having openings 304, and a pad 314. The pad 314 being coupled to the material 323 via the adhesive 327 which extends through the openings 304 in the latex 321.

Figure 43:
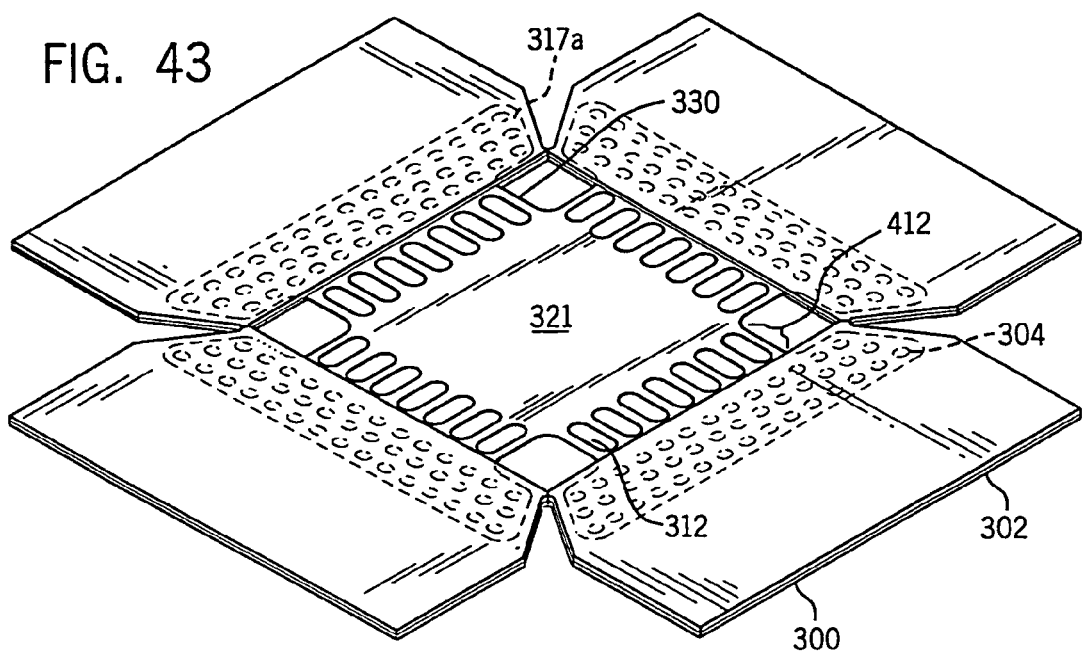
FIG. 43 is a perspective view of another embodiment of the present invention.
Figure 44:
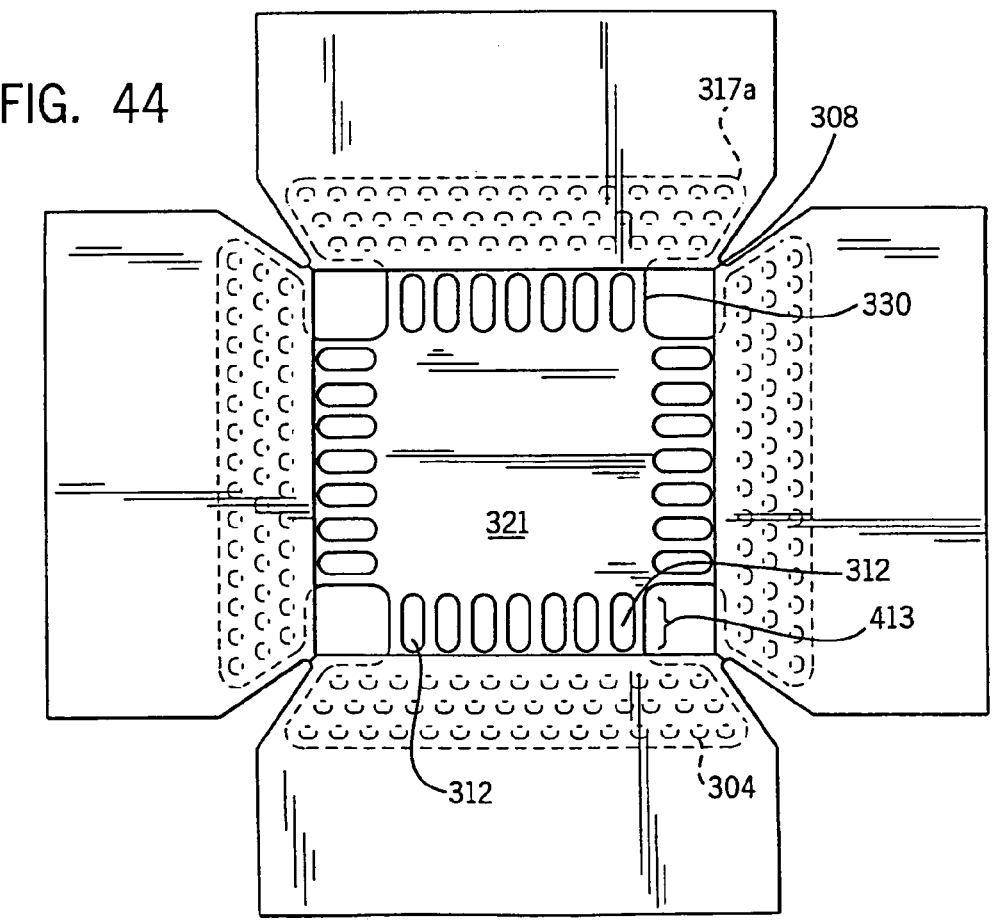
FIG. 44 is a top plan view of the embodiment disclosed in FIG. 43.
Figure 45:
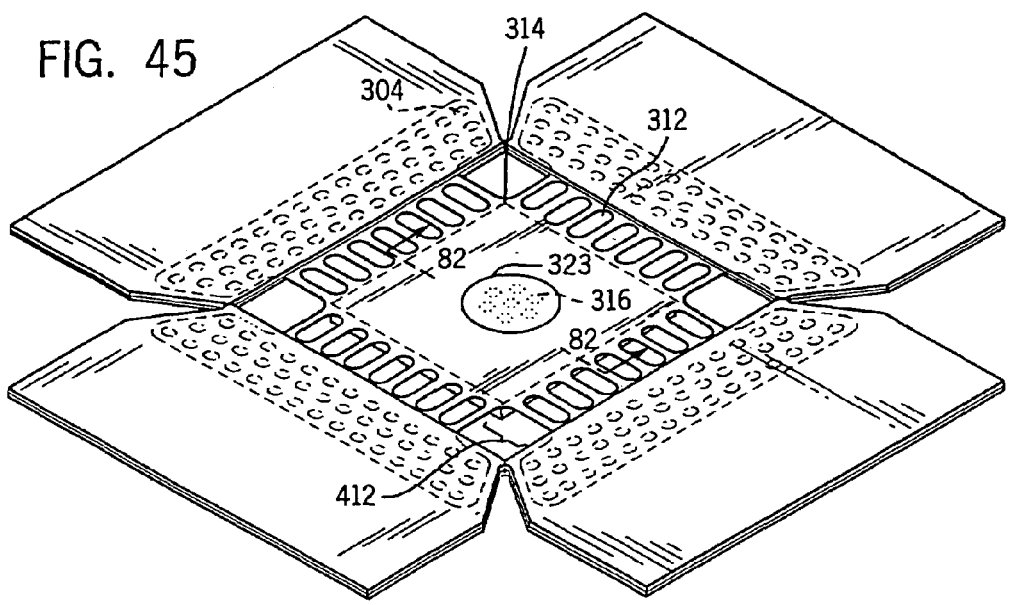
FIG. 45 is a perspective view of an another alternative structure of the present invention.
Figure 46:
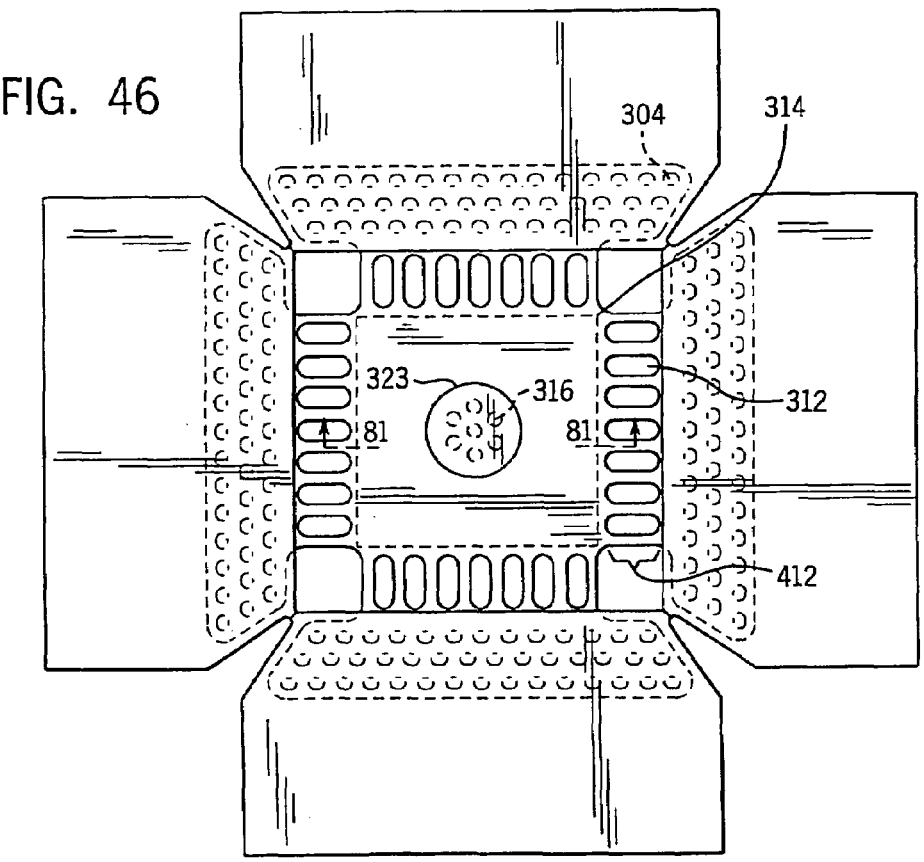
FIG. 46 is a top plan view of the embodiment disclosed in FIG. 45.

Referring to FIGS. 43 and 44 another alternative embodiment of the present invention may be seen. In this embodiment four anchor sections are again shown coupled via respective locking sections 317a. In this embodiment just a latex material 321 extends between the anchor sections 301, 303, 305, and 307. A curvature 330 is provided in the latex material 321 to allow for uniform stretching of the material. Also, a perforation 308 is provided to connect the anchor sections 303, 305, 307 and 301 to each other prior to use of the dressing 300. The perforations are broken when it is desired to use this embodiment of the dressing 300.

Figure 47:
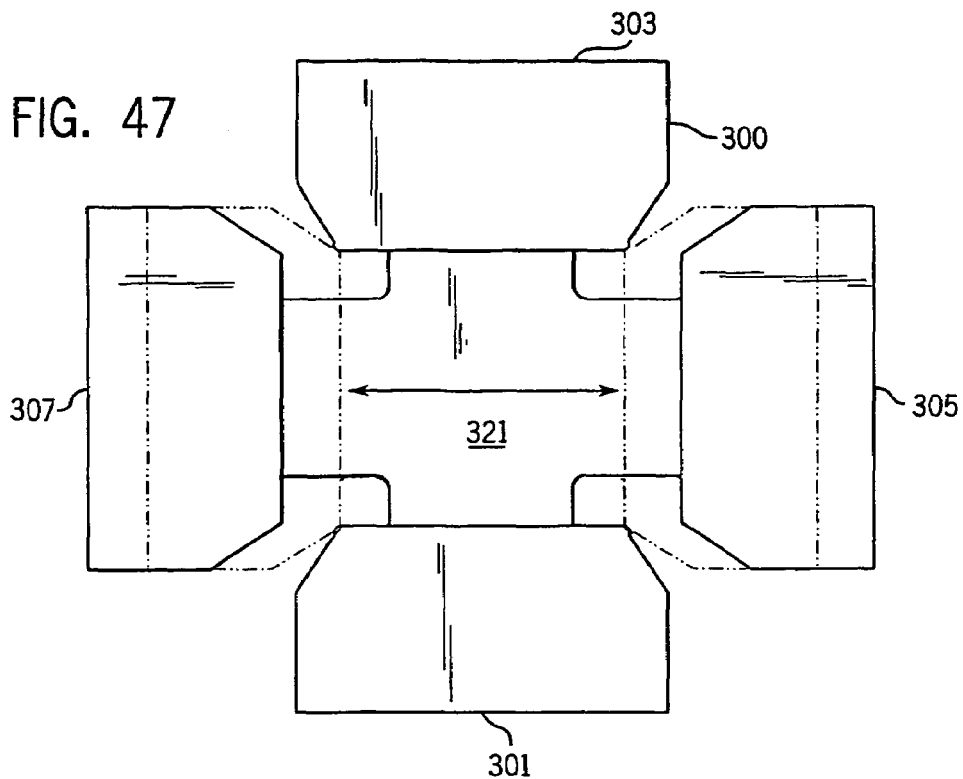
FIG. 47 is a top plan view illustrating how force may be distributed in two directions in a particular embodiment of the present invention.
Figure 48:
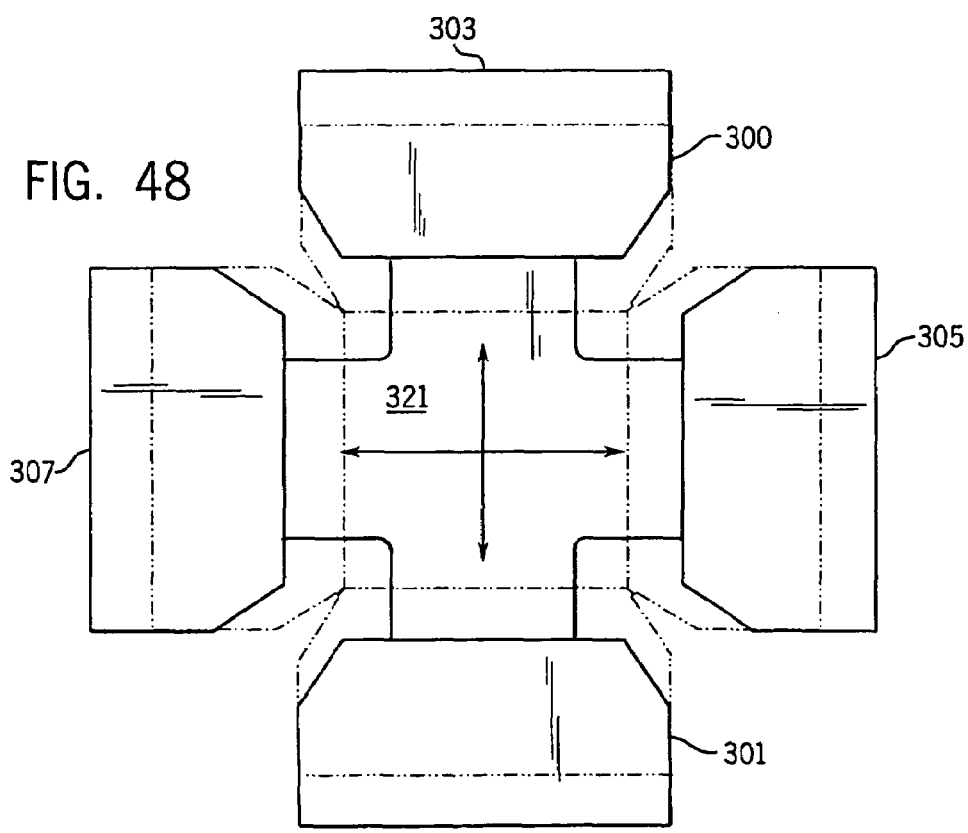
FIG. 48 is a top plan view illustrating how force may be distributed in four directions in a particular embodiment of the present invention.

Referring to FIGS. 47 and 48 it is again illustrated that the latex section 321 of the dressing 300 may be stretched or extended in a plurality of directions. This allows for versatility of use on a variety of surfaces.

Figure 49:
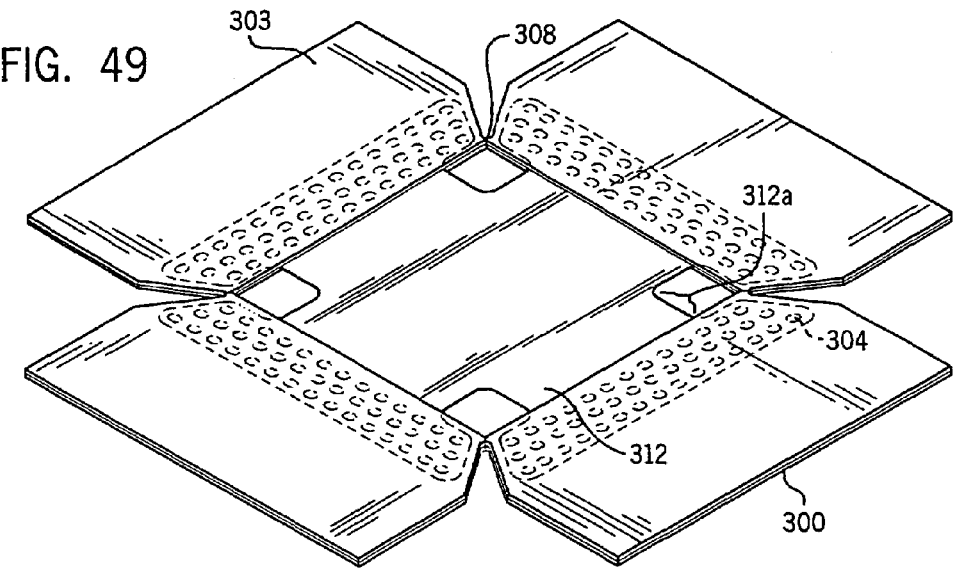
FIG. 49 is a perspective view of an another alternative structure of the present invention.
Figure 50:
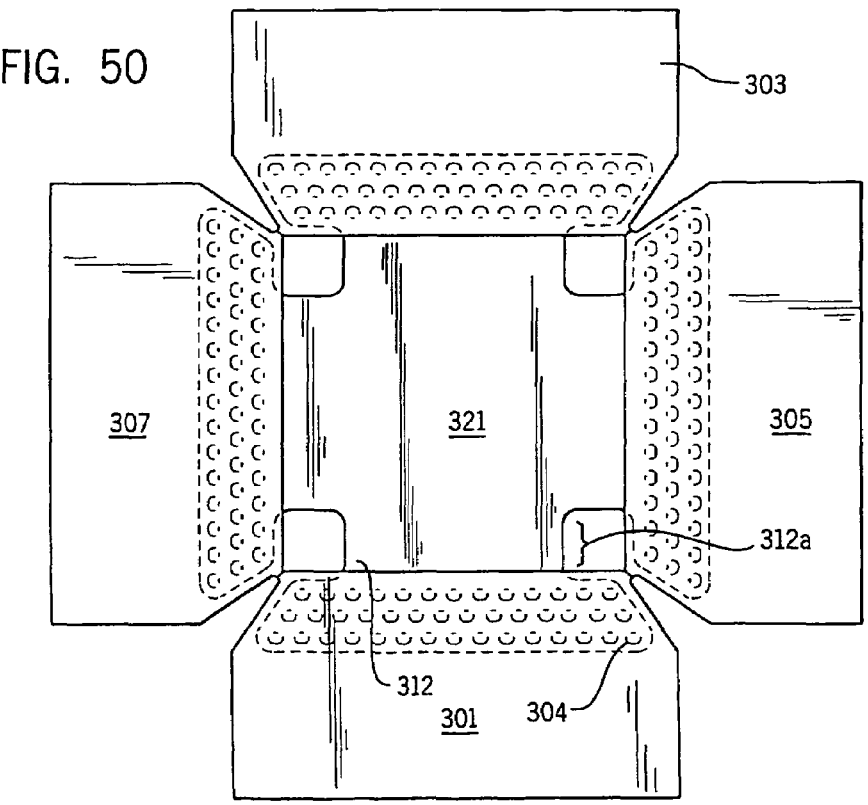
FIG. 50 is a top plan view of the structure disclosed in FIG. 49.

Referring to FIGS. 49 and 50 another alternative embodiment of the present invention is disclosed showing that the openings 312 may be deleted from the tensioning section 312a if desired without detracting from the principles of the invention disclosed herein.

Figure 53:
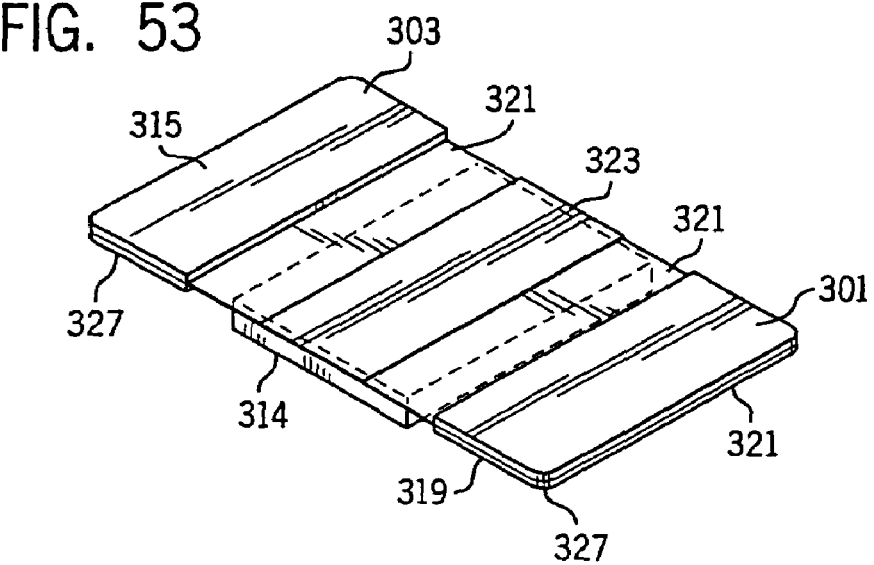
FIG. 53 is a perspective view of an another alternative structure of the present invention.

Referring to FIG. 53 a very simple version of the present invention is illustrated. In this embodiment the dressing 300 is composed of a piece of latex 321 having two ends to which anchors 301 and 303 are respectively attached using an adhesive. The ends of the latex 321 are simply sandwiched between the layers 315 and 319. A piece of stiffening material 323 is glued across the mid-section of the latex 321 and pad 314 is glued to the underside of the latex 321 as illustrated. The bottom side of each respective anchor section 301 and 303 having an adhesive 327 applied thereto.

Figure 54:
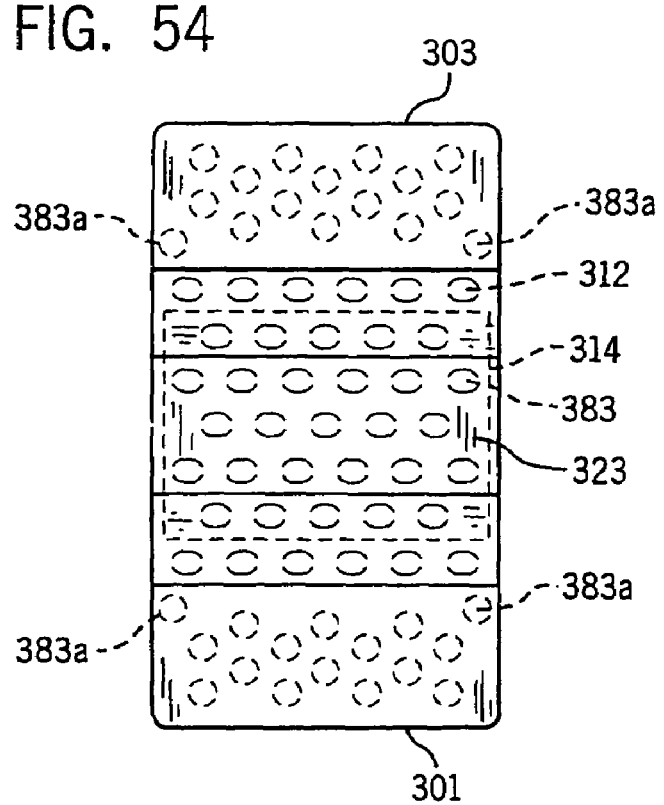
FIG. 54 is a top plan view of the an alternative embodiment to the structure disclosed in FIG. 53.

Referring to FIG. 54 illustrates the embodiment of FIG. 53 with the addition of a series of openings 383 being applied to the entire dressing 300. Depending upon the material through which the opening 383 is made the function of the opening will vary. Openings 312 in the latex 321 will act to vary the elasticity of the latex. Openings 383a will create stress points and help maintain the dressing 300 in a straight alignment between its anchors 301 and 303. Openings 383b will allow air access to the treatment area.

Figure 55:
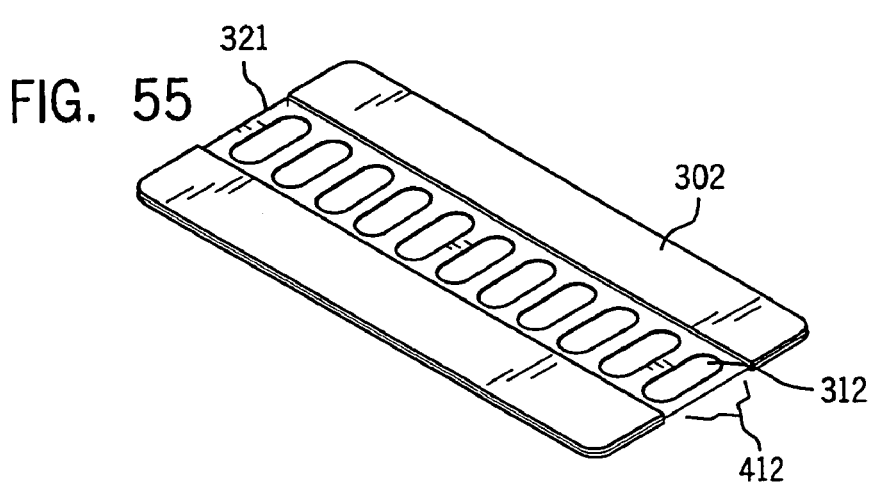
FIG. 55 is a perspective view of an another alternative structure of the present invention.
Figure 56:
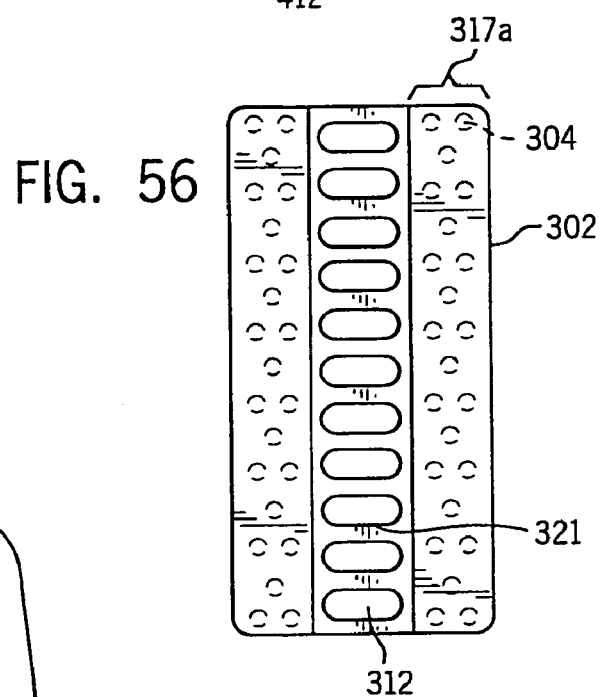
FIG. 56 is a top plan view of an alternative embodiment of the alternative structure shown in FIG. 55.
Figure 57:
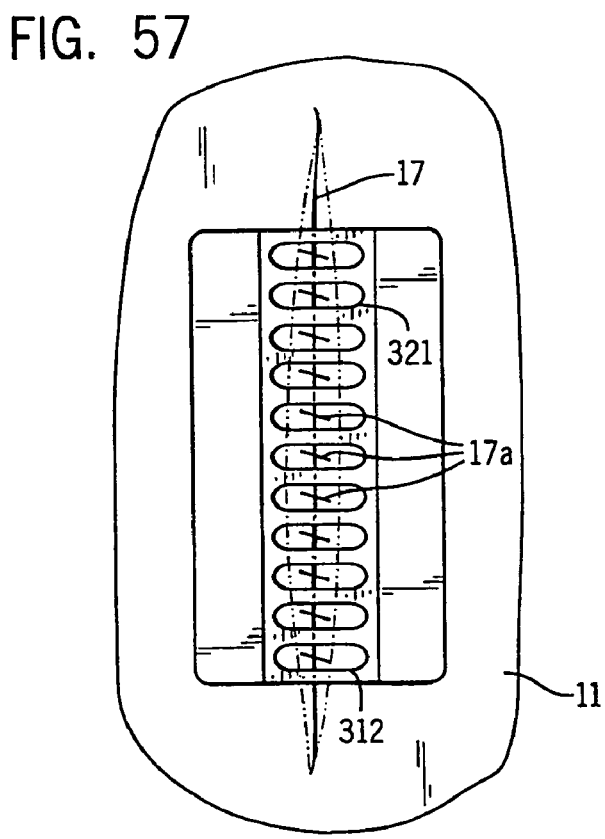
FIG. 57 is a top plan view showing the structure disclosed in FIG. 55 applied over the incision of a wound and acting as a guide for suturing the wound.
Figure 58:
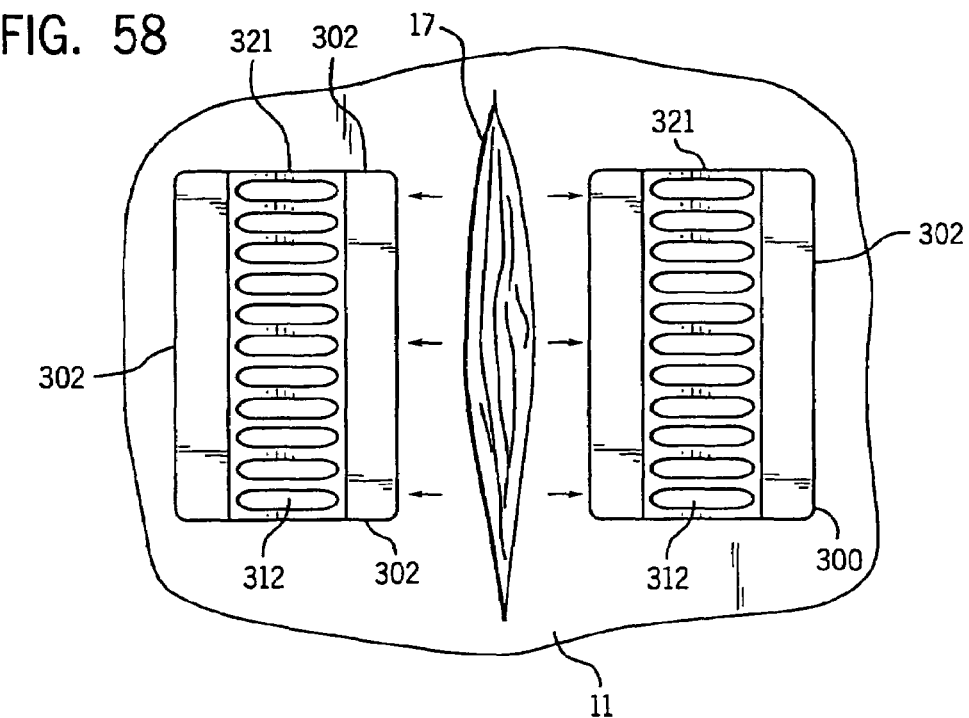
FIG. 58 is a top plan view showing the two of the structures disclosed in FIG. 55 being used to hold a wound open.
Figure 59:
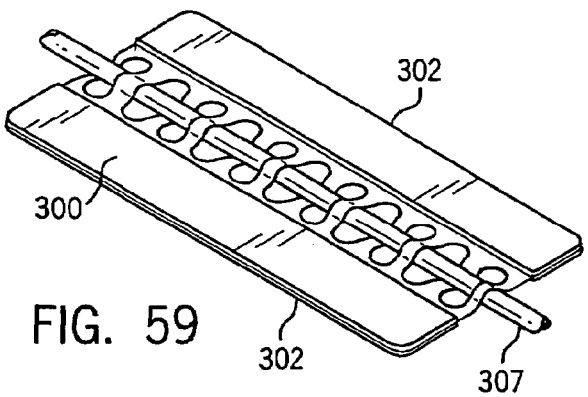
FIG. 59 is a perspective view showing the structure disclosed in FIG. 55 being used for guiding an intravenous tube and holding the tube in a predetermined position.
Figure 60:
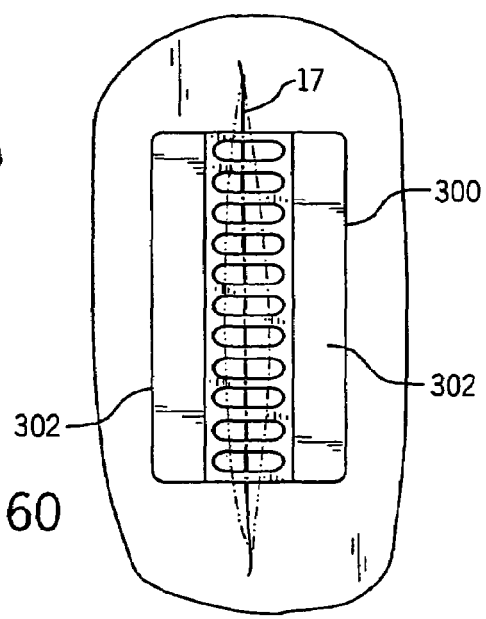
FIG. 60 is a top plan view showing the structure disclosed in FIG. 55 holding the edges of a wound or incision together.
Figure 61:
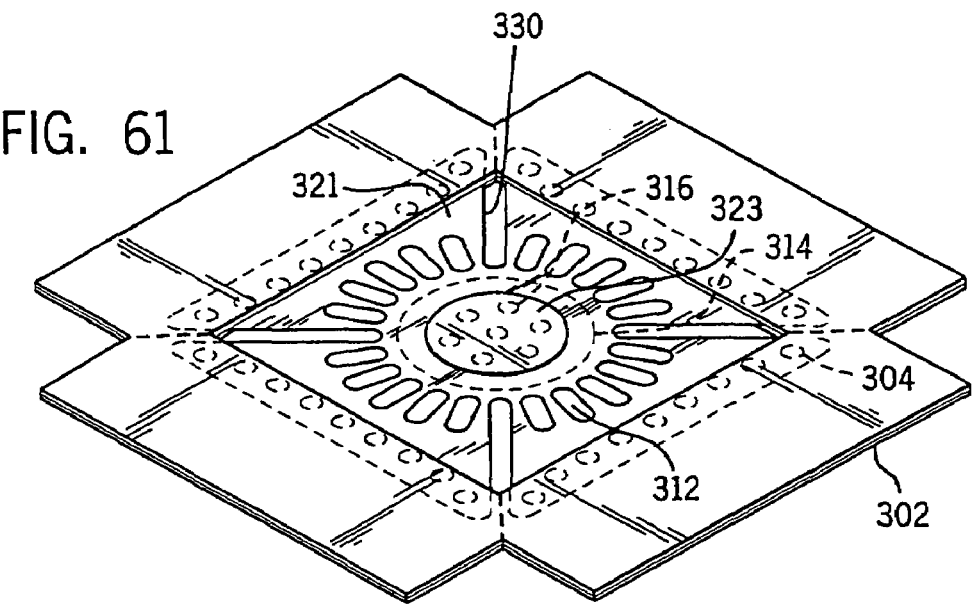
FIG. 61 is a perspective view of an another alternative structure of the present invention.
Figure 62:
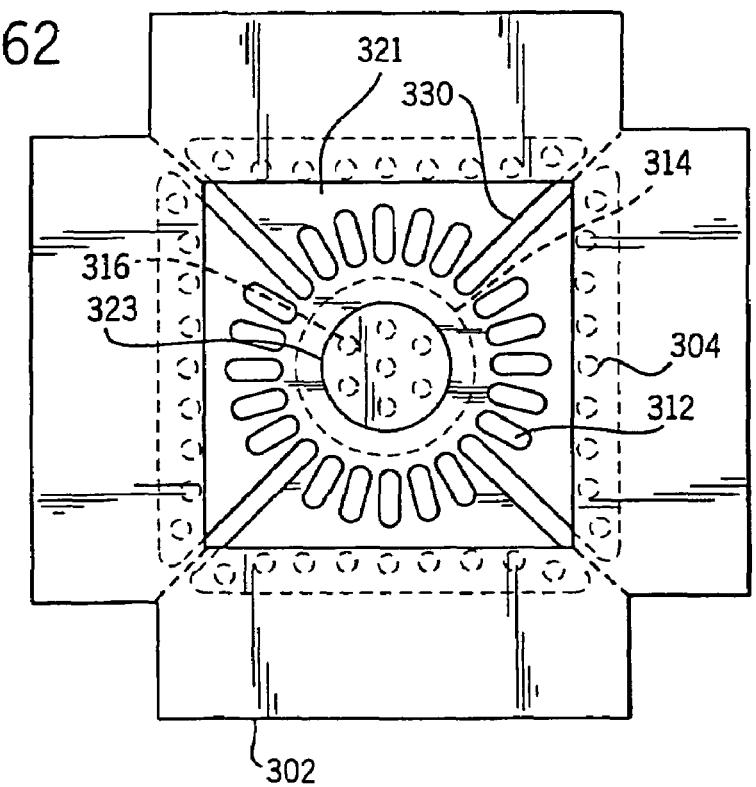
FIG. 62 is a top plan view of the structure disclosed in FIG. 61.
Figure 63:
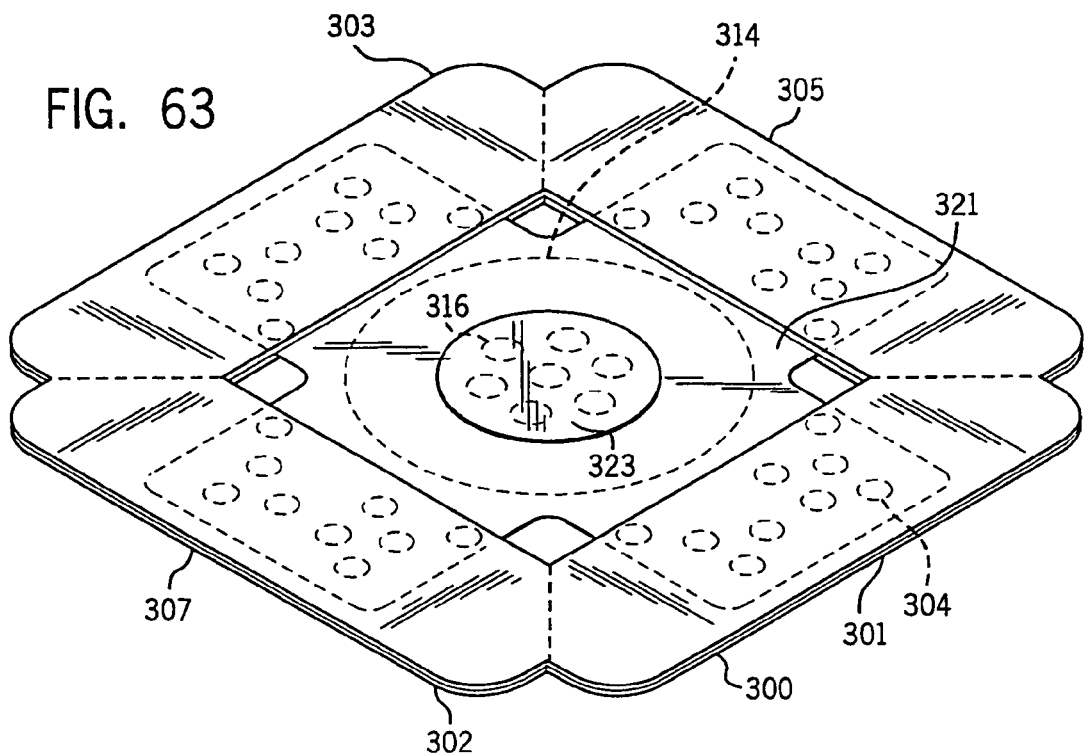
FIG. 63 is a perspective view of an another alternative structure of the present invention.
Figure 64:
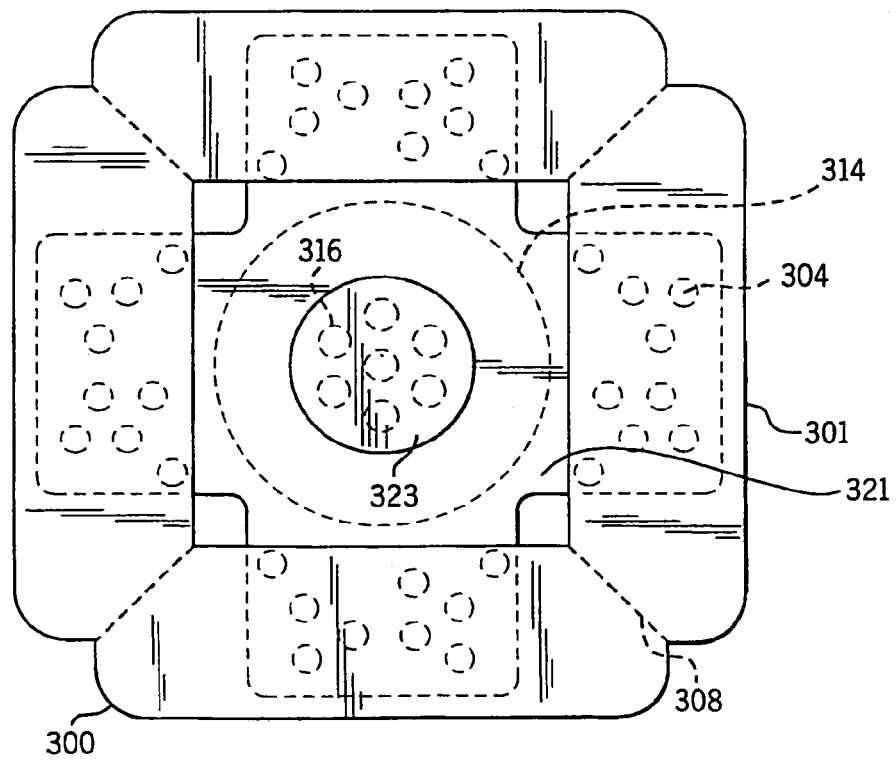
FIG. 64 is a top plan view of the structure disclosed in FIG. 63.
Figure 65:
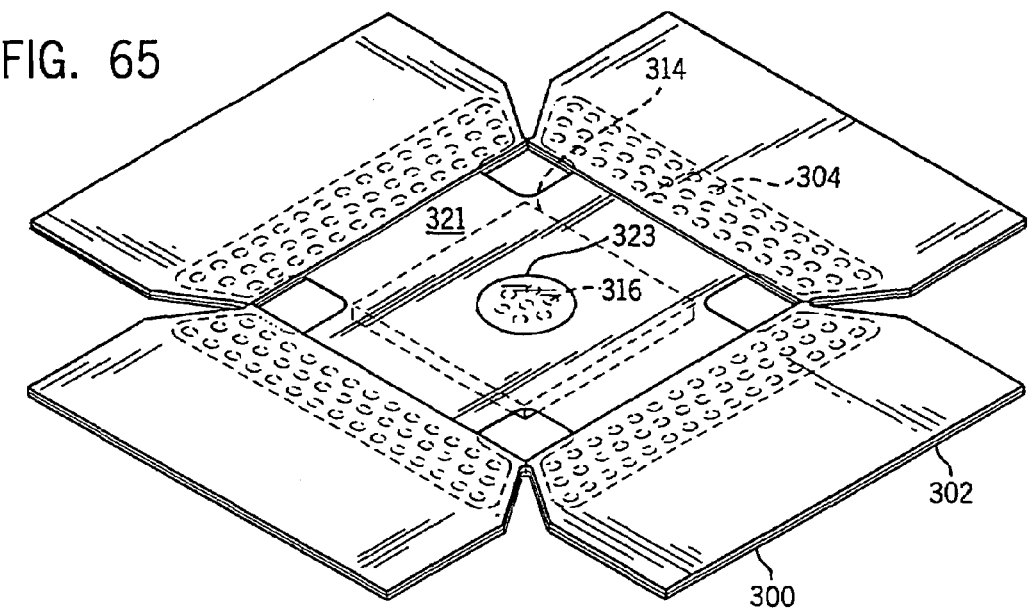
FIG. 65 is a perspective view of an another alternative structure of the present invention.
Figure 66:
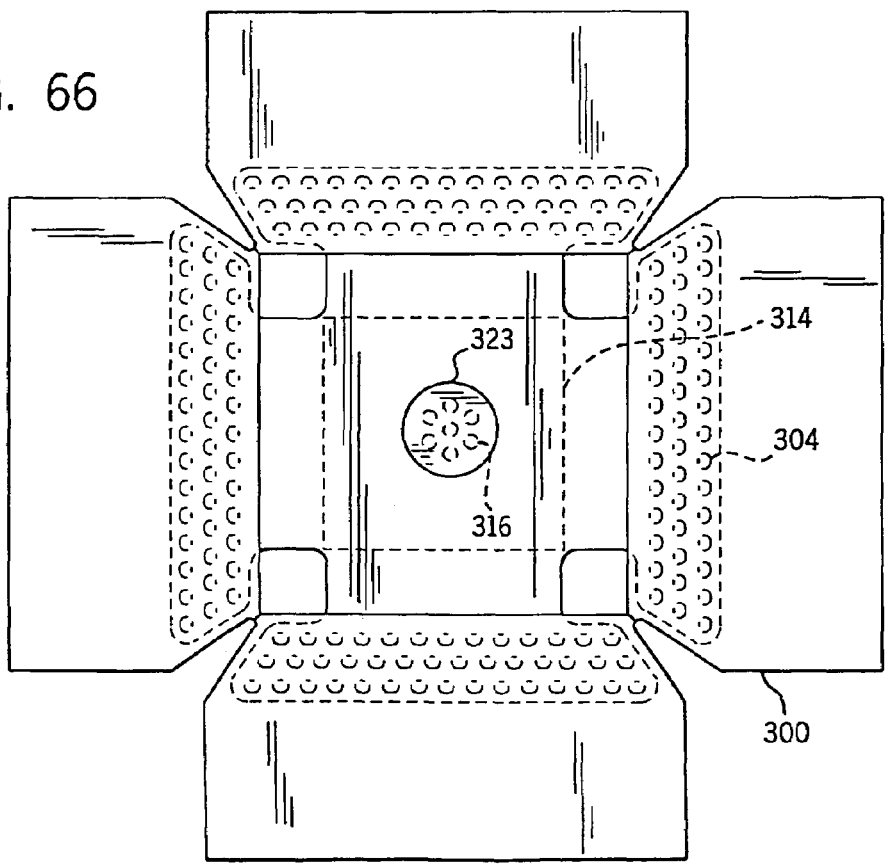
FIG. 66 is a top plan view of the structure disclosed in FIG. 65.

Referring now to FIGS. 55, 56, 57, 58, 59, and 60 another embodiment of the dressing 300, similar to the embodiment disclosed in FIGS. 37 and 38 is disclosed. In this embodiment the entire latex section 321 is essentially comprised of tensioning section 412 having openings 312. The anchors 301 and 303 function as previously described. The latex 321 in FIG. 55 is held in place as described in FIG. 53 while the latex 321 in FIG. 56 is held in place as described in reference to FIGS. 35 and 36 by adhesive 327 extending through openings 304. FIGS. 57-60 illustrate that this embodiment may be placed over an incision 17 to act as a guided for applying stitches 17a, see FIG. 57, or embodiments may be placed to either side of an incision 17 to hold the incision open, see FIG. 58, or the openings 312 may be used to hold an intravenous tube 307 in place, see FIG. 59, or the dressing 300 simply be used to hold an incision 17 closed without resorting to the application of stitches 17a, see FIG. 60.

Referring to FIGS. 61 through 66 and FIGS. 70 through 76 a variety of alternative designs of the dressing 300 may be seen. All the dressings 300 disclosed operate on the same principles previously disclosed but they are shown to illustrate that shape of the latex 321 and the openings 312 may varied without departing from the invention described herein. Also, illustrated is the fact that the pad 314 and the material 323 may vary in size and shape. Further, the radius or arcuate section 330 may be varied in shape to provide for uniform distribution of tension across the latex 321.

Figure 67:
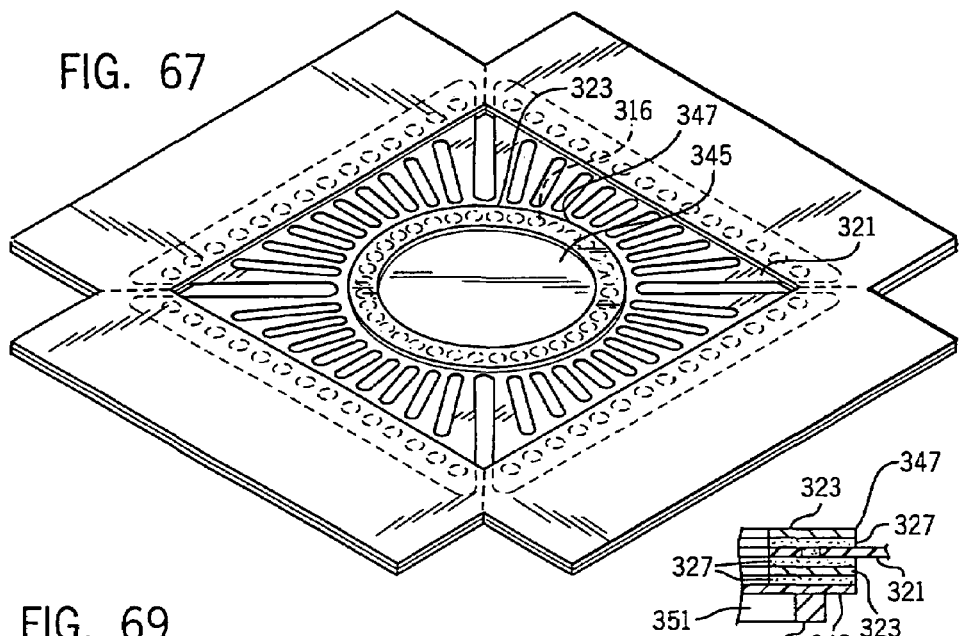
FIG. 67 is a perspective view of an another alternative structure of the present invention.
Figure 68:
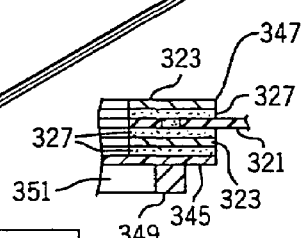
FIG. 68 is a view from line 68-68 of FIG. 69.
Figure 69:
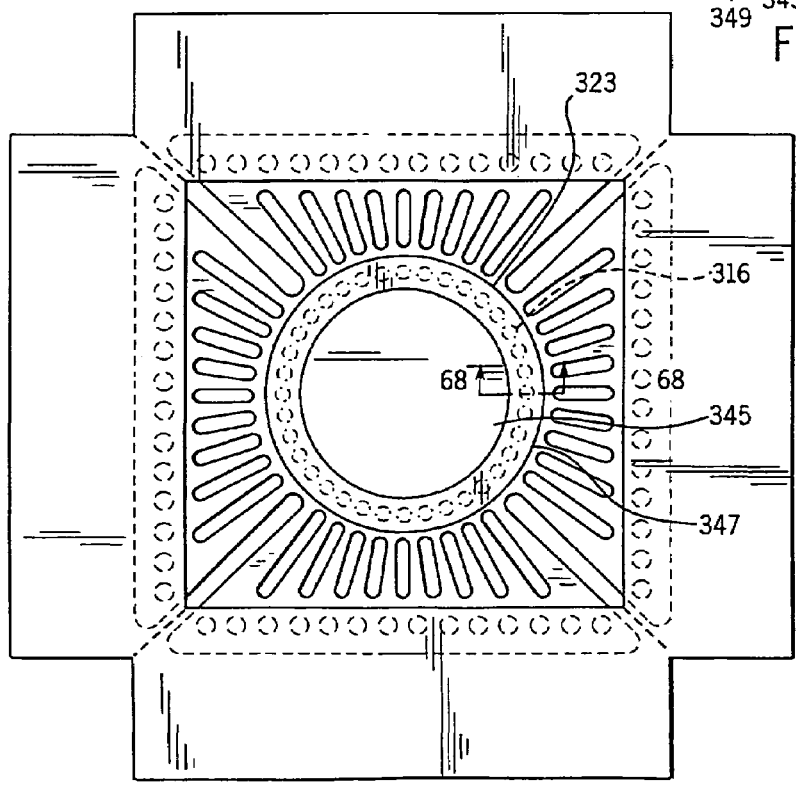
FIG. 69 is a top plan view of the structure disclosed in FIG. 67.
Figure 70:
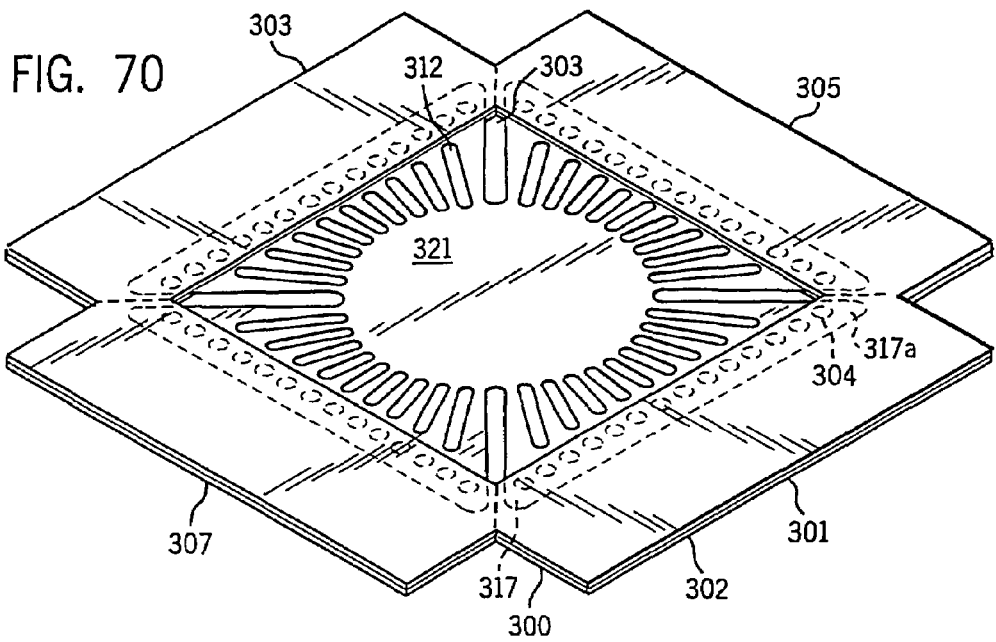
FIG. 70 is a perspective view of an another alternative structure of the present invention.
Figure 71:
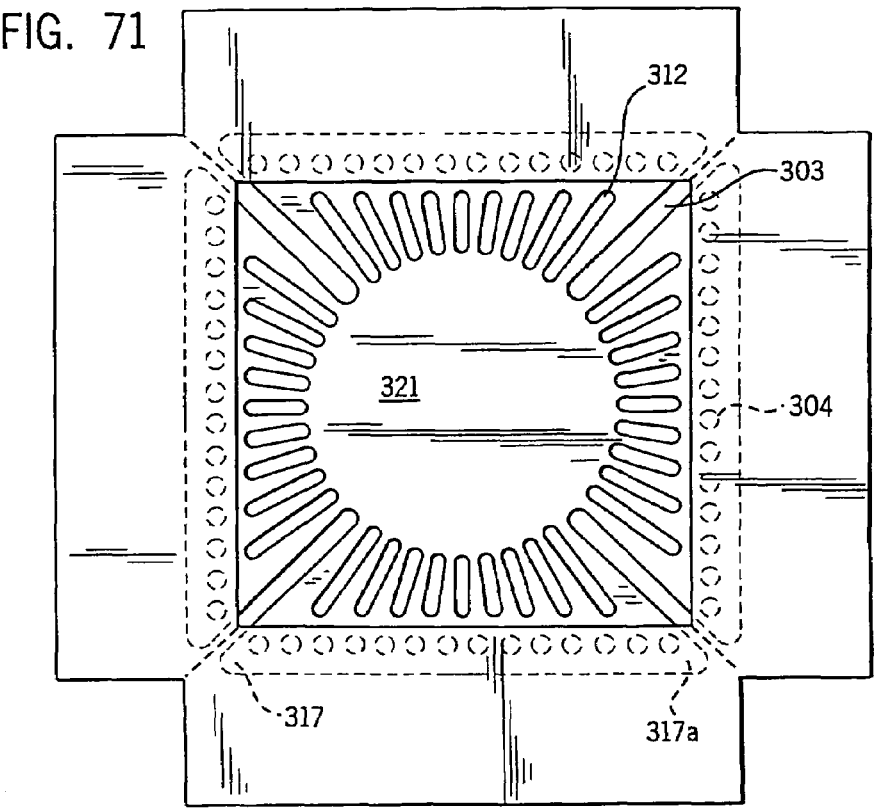
FIG. 71 is a top plan view of the structure disclosed in FIG. 70.
Figure 72:
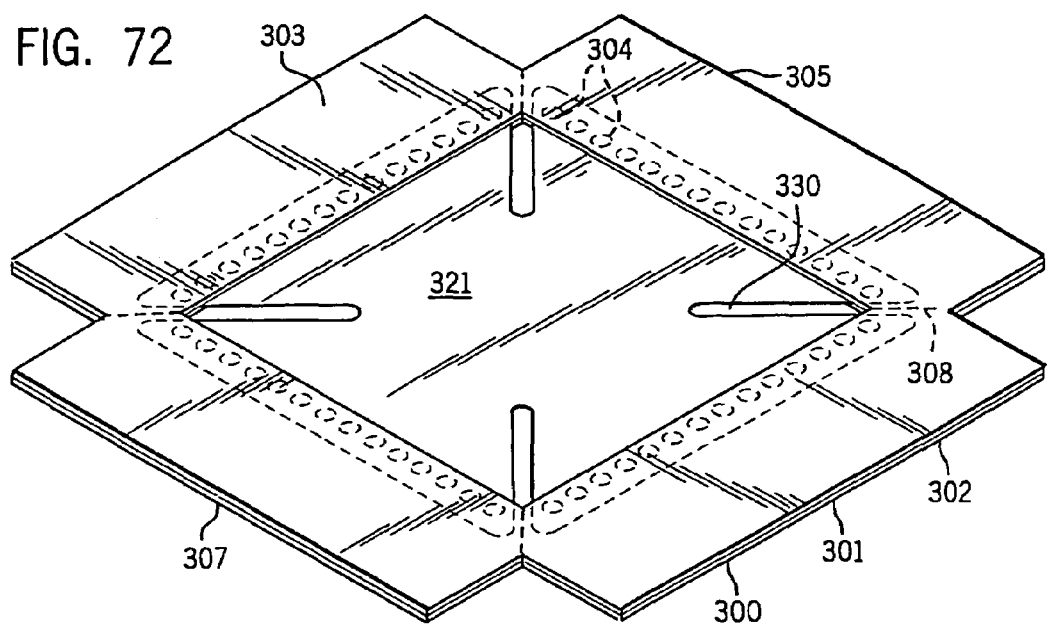
FIG. 72 is a perspective view of an another alternative structure of the present invention.
Figure 73:
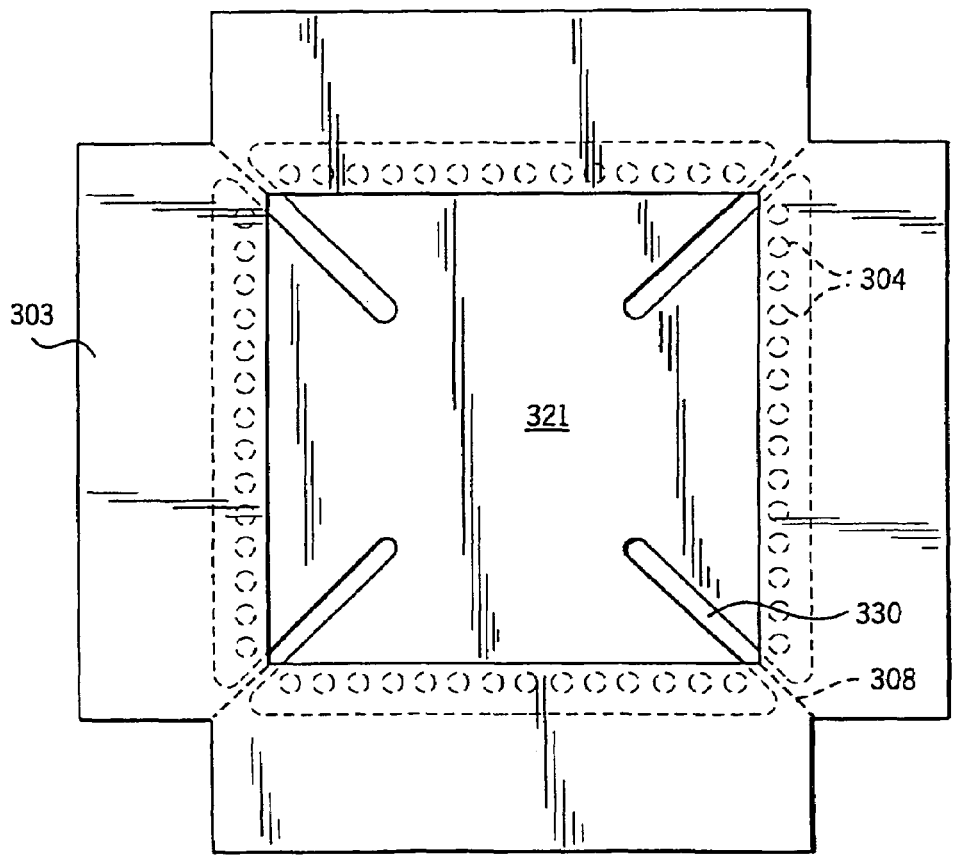
FIG. 73 is a top plan view of the structure disclosed in FIG. 74.
Figure 74:
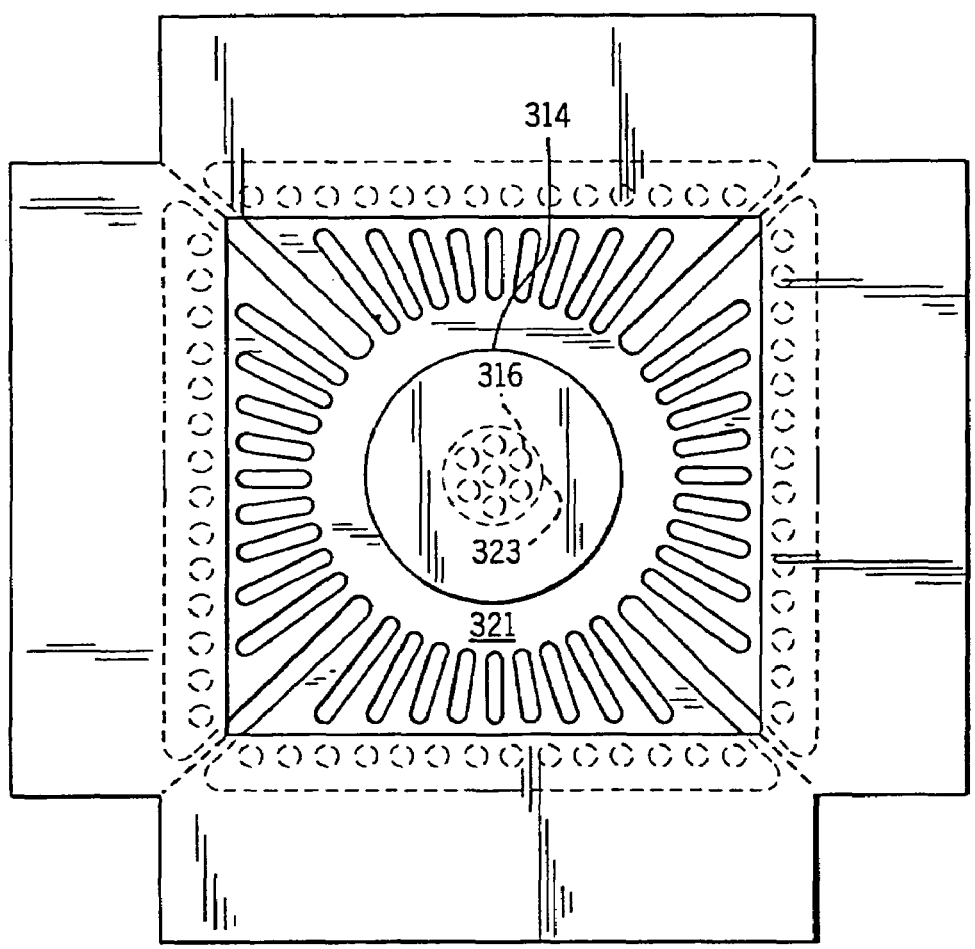
FIG. 74 is a top plan view of another alternative embodiment of the present invention.
Figure 75:
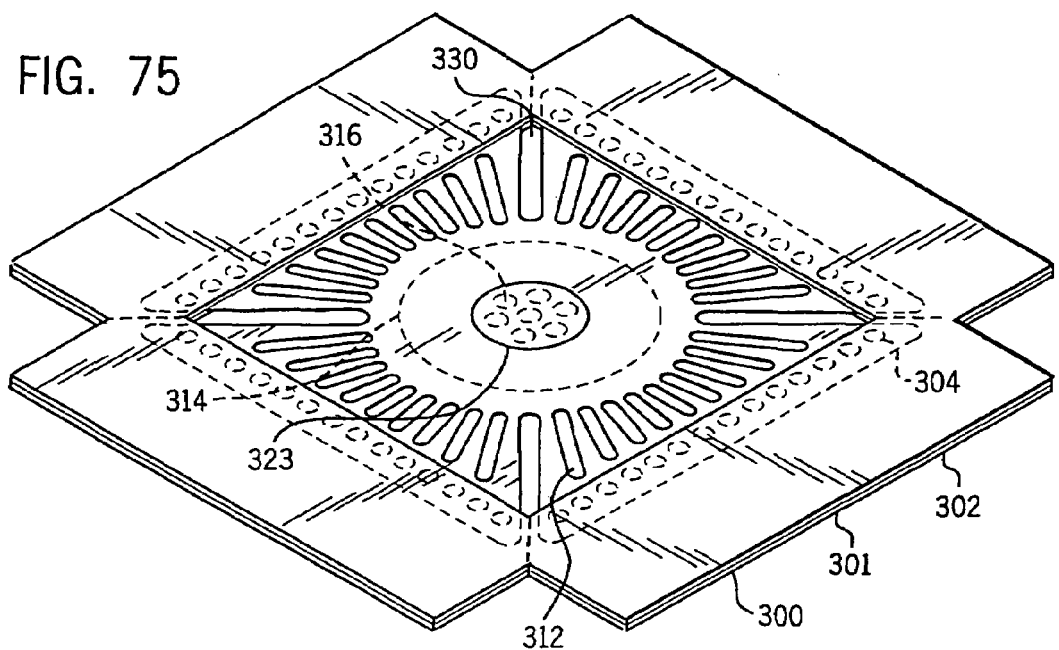
FIG. 75 is a perspective view of an another alternative structure of the present invention.
Figure 76:
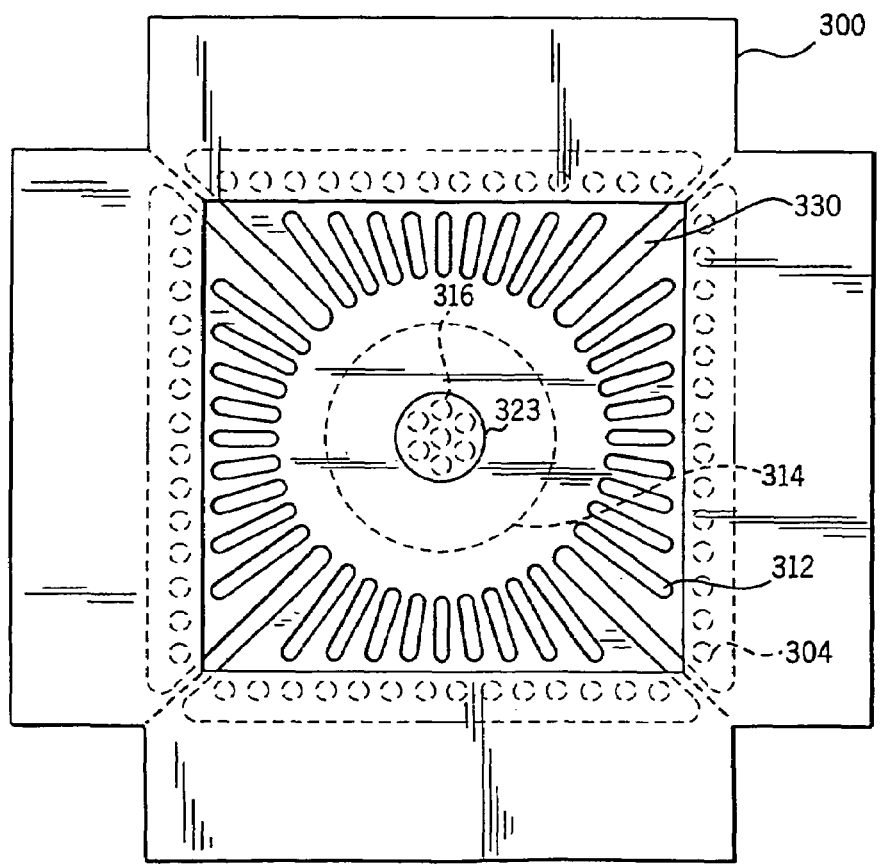
FIG. 76 is a top plan view of the structure disclosed in FIG. 75.

Referring to FIGS. 67 through 69 another embodiment of the present invention may be seen wherein the latex 321 includes a ring section 347 of material 323. Coupled to the ring section 347 is the latex 321 and a clear urethane material 345 of the type commonly suitable for medical applications; alternative materials may be used such as any suitable breathable material depending upon the application desired. As illustrated by FIG. 68 the ring section 347 is comprised of a layer of TYVEC brand material 323, a layer of adhesive 327, a layer of latex 321 having openings 316 which function in the same manner as openings 304, another layer of adhesive 327, another layer of TYVEC brand material 323, the clear material 345, and a colloid adhesive 349. This structure creates a stable space 351 over the desired area and the colloid 349 isolates the area and prevents stretching of the epidermis 11 under the space 351 so that the wound or other desired area is kept in an isolated environment which may be observed through the material 345. The colloid 349 and the material 345 isolating the wound from external sources of infection.

Figure 85:
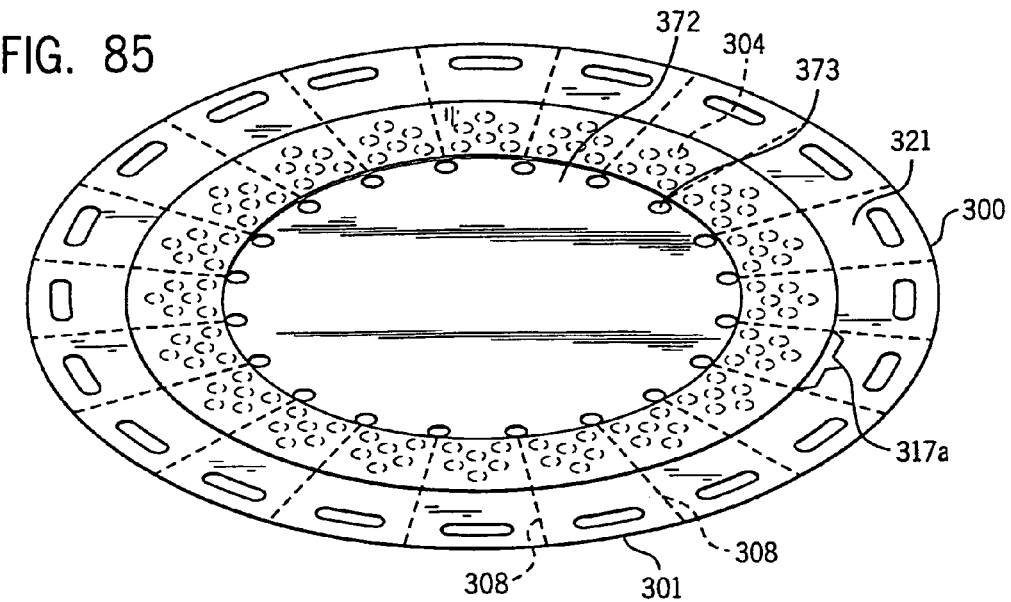
FIG. 85 is a top plan view of another alternative embodiment of the present invention.
Figure 86:
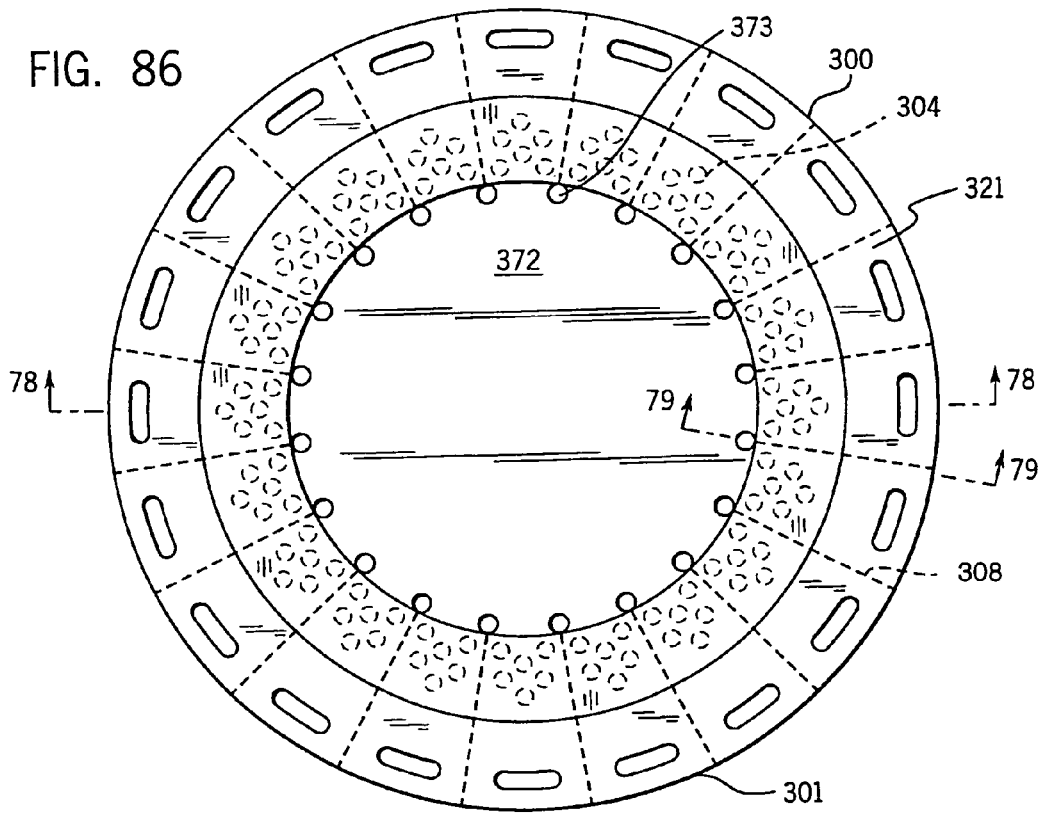
FIG. 86 is a perspective view of the alternative structure of the present invention disclosed in FIG. 85.

Referring to FIGS. 85 and 86 another alternative design of the present invention may be observed. In this embodiment the center section is a breathable membrane 372 of a type commonly used for dressing applications. Perforations 308 allow the dressing to be broken apart to form a plurality of anchor sections 301. Openings 373 are provided in the member 372 to prevent tearing of the membrane 372. A locking section 317a, previously described, is provided. Referring to FIGS. 78 and 79 the cross-sectional construction may be seen to include at top layer of material 323, a layer of adhesive 327, latex 321 including openings 304, adhesive 327, material 323, adhesive 327, the breathable membrane 372, and a colloid adhesive 349. The dressing 300 capable of covering a desired area of an epidermis 11 and substantially isolating that area from external contamination.

Figure 83:
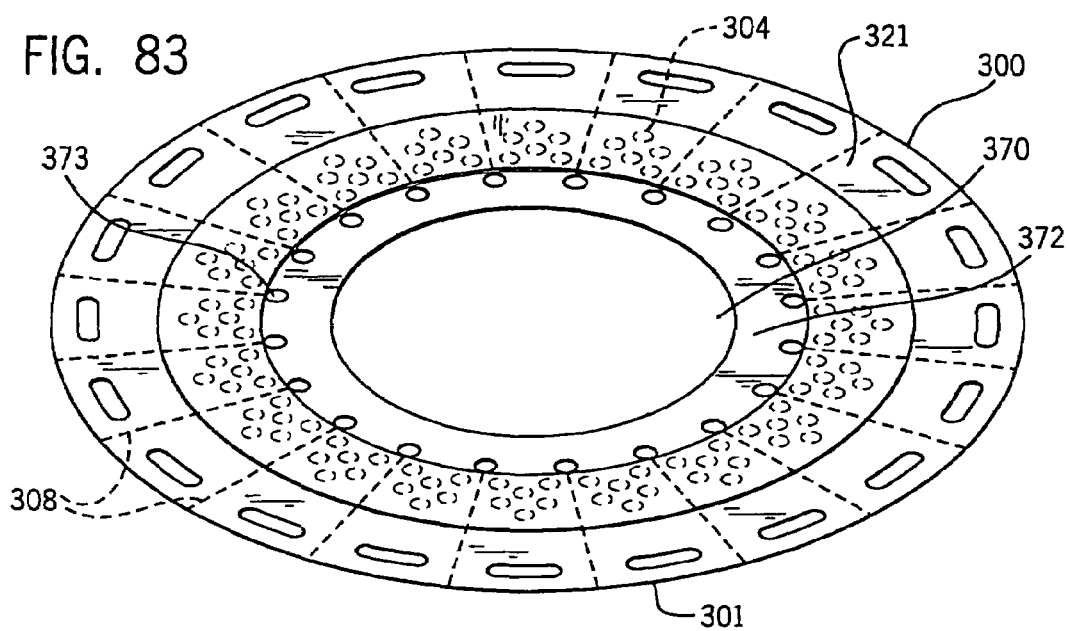
FIG. 83 is a top plan view of another alternative embodiment of the present invention.
Figure 84:
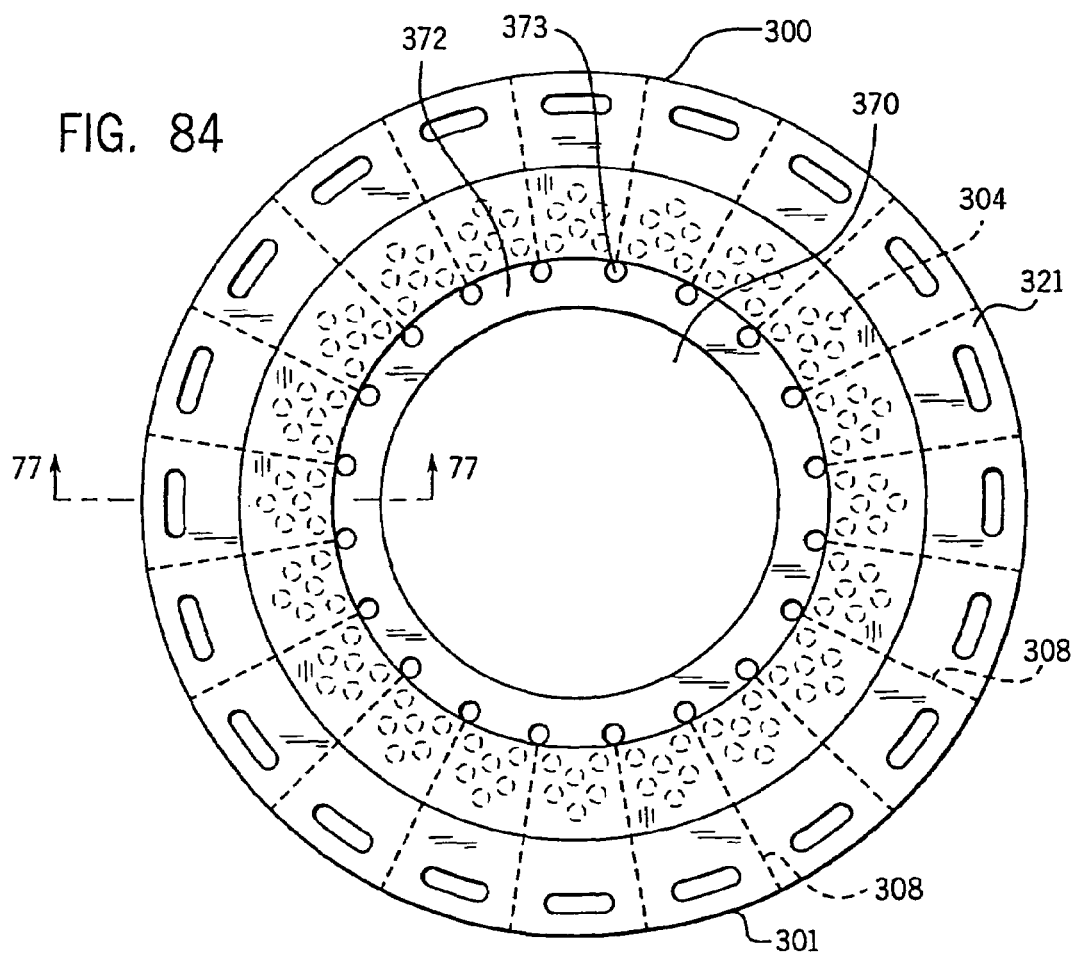
FIG. 84 is a perspective view of the alternative structure of the present invention disclosed in FIG. 83.

Referring now to FIGS. 83, 84, and 77 the same structures as shown in FIGS. 85 and 86, 78 and 79 are shown with the exception that the breathable membrane 372 has been eliminated so that there is only an opening 370. This dressing 300 is believed to have application where it is desired that the wounded or burnt area of the epidermis be exposed to air. Since the spring action of the latex 321 will press down on the epidermal area surround the wound or burn within the opening 370 this is believed to cause the wound or burn to well up and thus receive maximum exposure.

Referring now to FIG. 80 another alternative embodiment similar to the structure disclosed in FIG. 78 with the exception that the breathable membrane 372 has been replaced with an sealed membrane 399 such as a urethane commonly used to hold IV type fluids. Extending through this membrane 399 is an input port and an output port. This dressing 300 could be used to seal a wound from external contamination but allow the wound to be irrigated or medicine applied or tissue samples taken.

Figure 87:
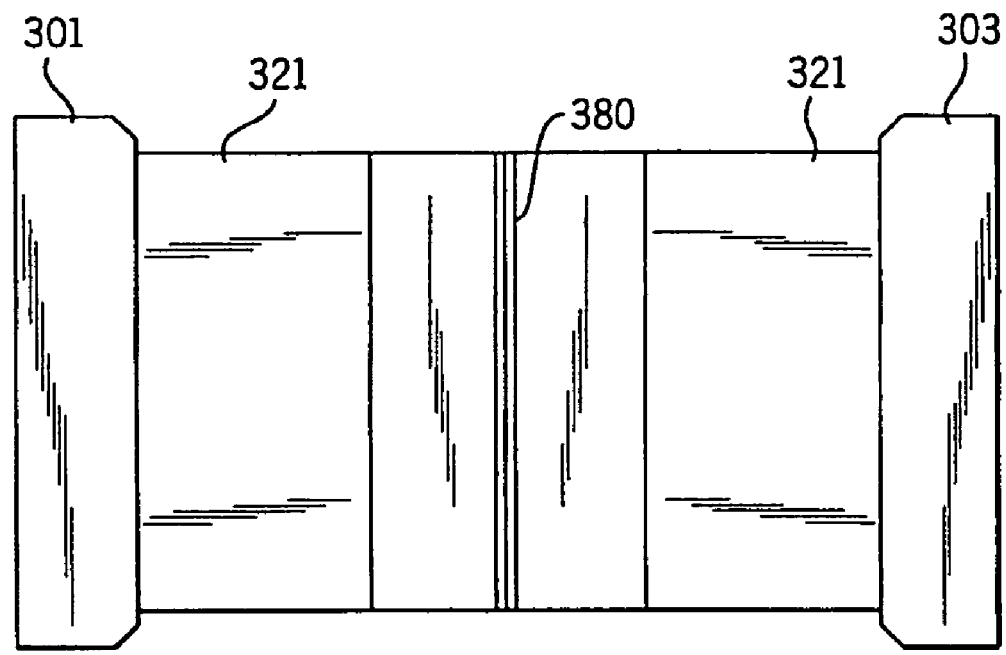
FIG. 87 is a top plan view of another alternative embodiment of the present invention.
Figure 88:
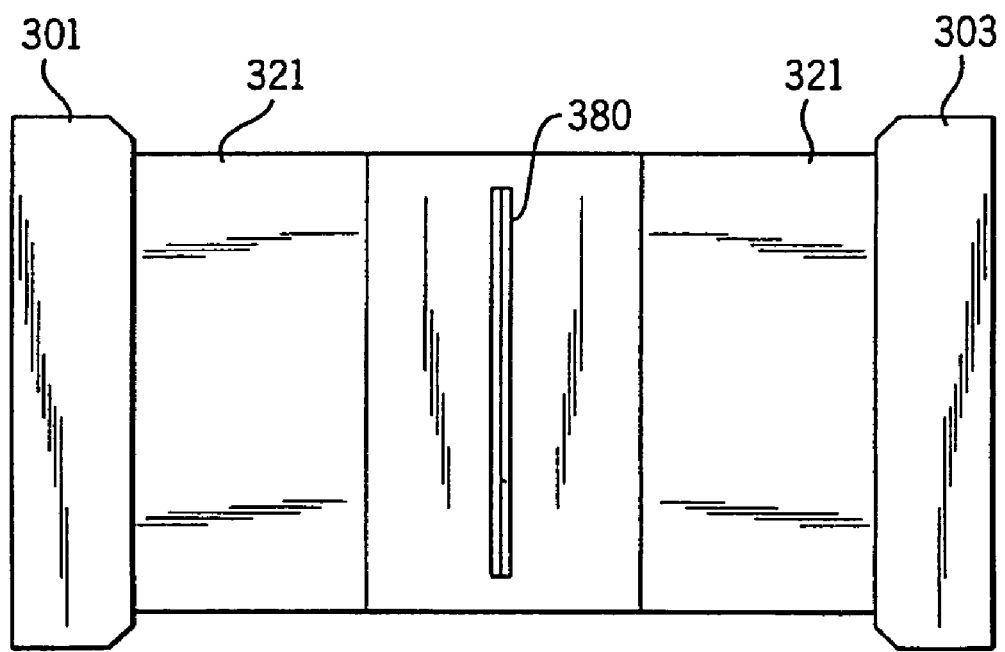
FIG. 88 is a top plan view of another alternative embodiment of the present invention.
Figure 89:
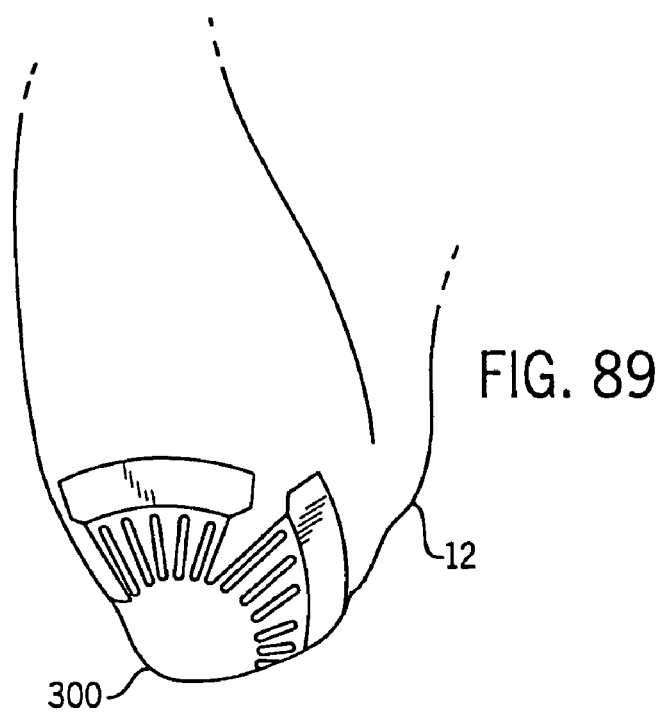
FIG. 89 is an illustration showing how the embodiment disclosed in FIG. 70 may be used on an area of the human body that is subject to a high degree of movement.
Figure 90:
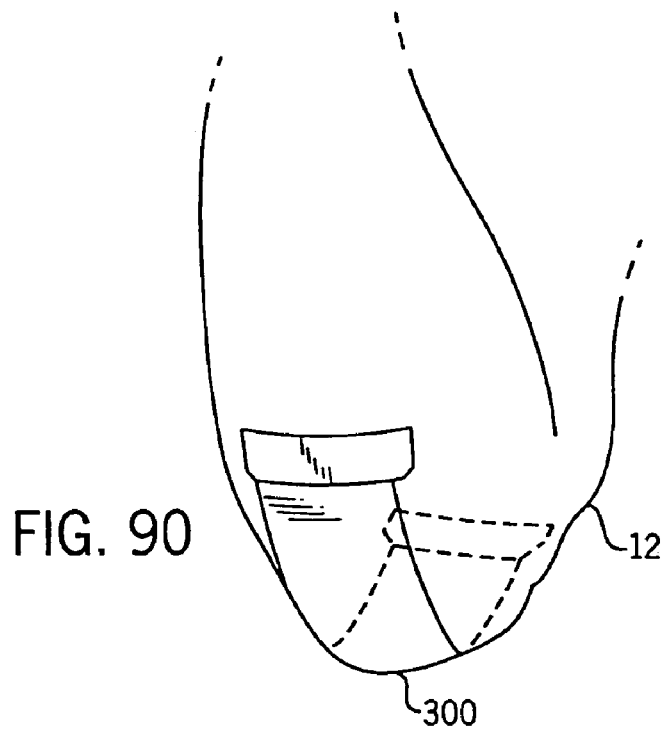
FIG. 90 is an illustration showing how another alternative embodiment of the present invention may be used on an area of the human body that is subject to a high degree of movement.
Figure 91:
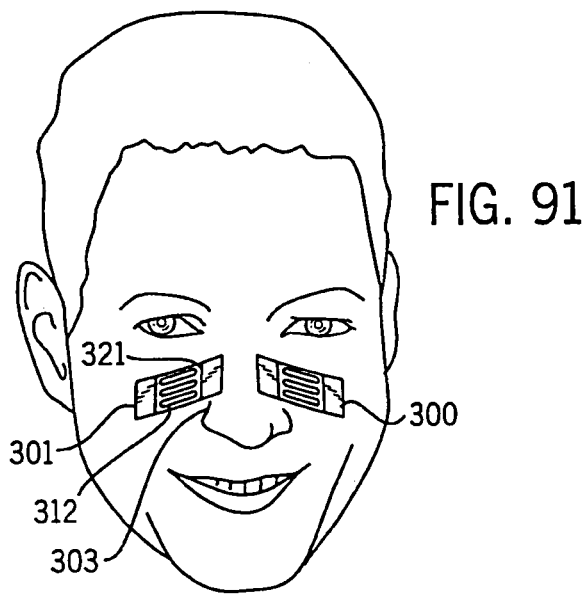
FIG. 91 illustrates how another alternative embodiment of the present invention may be used as a nasal dilator.
Figure 92:
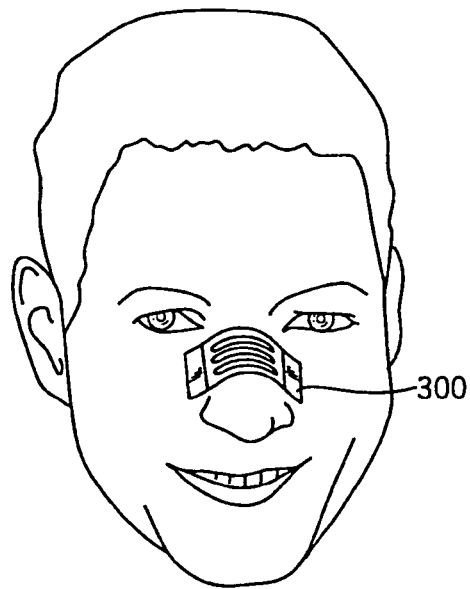
FIG. 92 illustrates another method by which the alternative embodiment of the present invention shown in FIG. 91 may be used as a nasal dilator.
Figure 93:
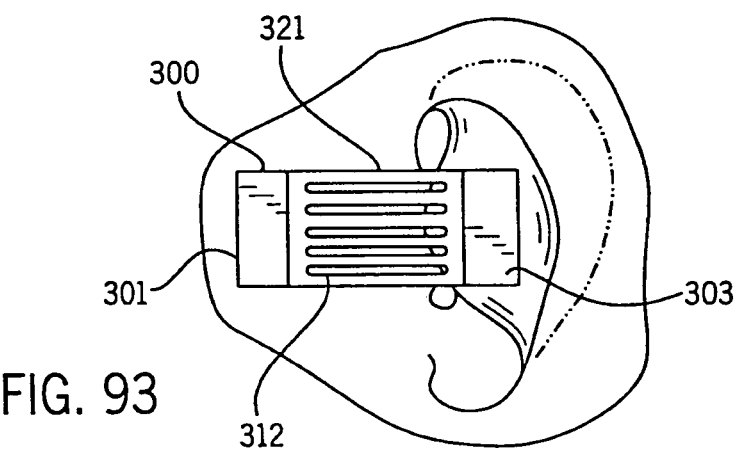
FIG. 93 illustrates how the embodiment shown in FIG. 91 may be used to hold a flap of skin, in this case a human ear flap, in a predetermined position. This is useful where its is desired to have easy access to an area that might otherwise be blocked by a fold or flap of skin thus making work on that area difficult or cumbersome.

Referring now to FIGS. 87 and 88 another embodiment is illustrated showing a resealable closure 380. The closure or zipper 380 may bisect the dressing or extend only partially across the dressing 300. The closure 380 is provided to allow access to the wound or burn or other area without having to remove and reapply the bandage.

Referring now to FIGS. 89-93 various applications of the dressings 300 described herein may be seen to be illustrated in use on a human being.

Figure 94:
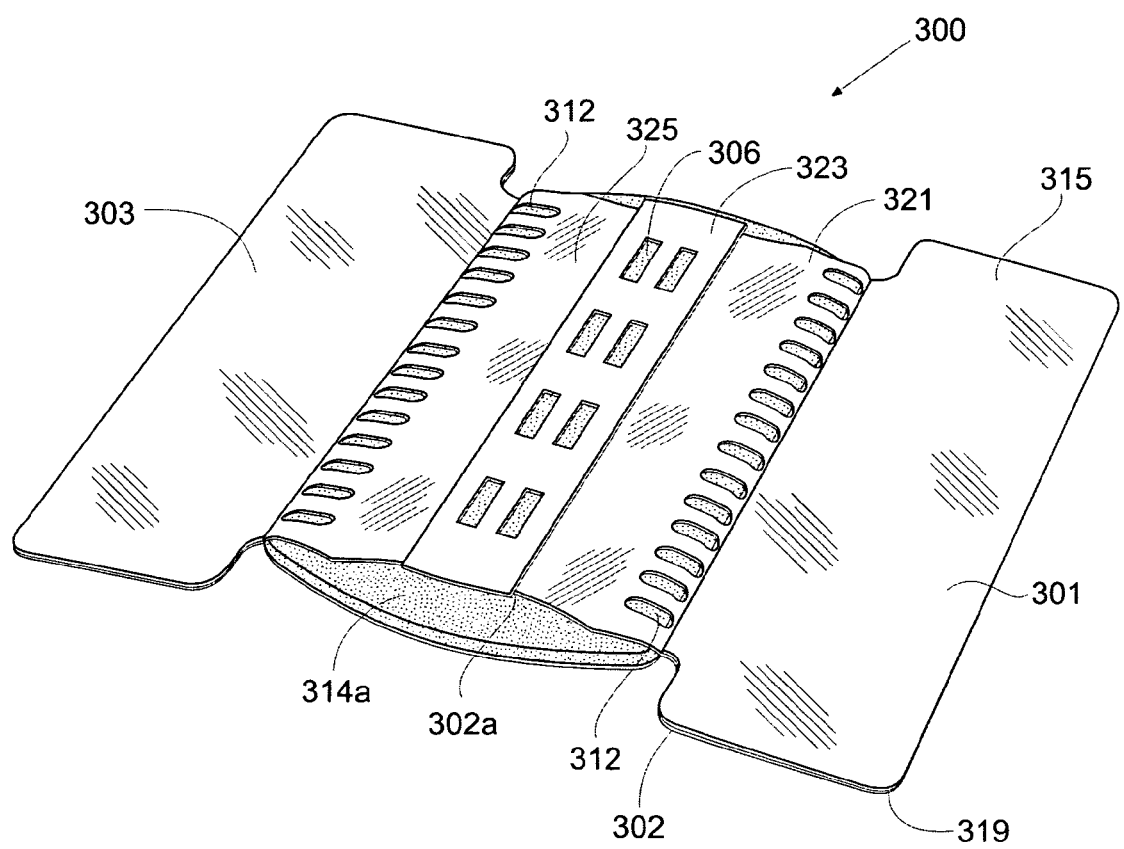
FIG. 94 is a perspective view of one embodiment of the present invention, and illustrating a hydrophilic pad material.
Figure 95:
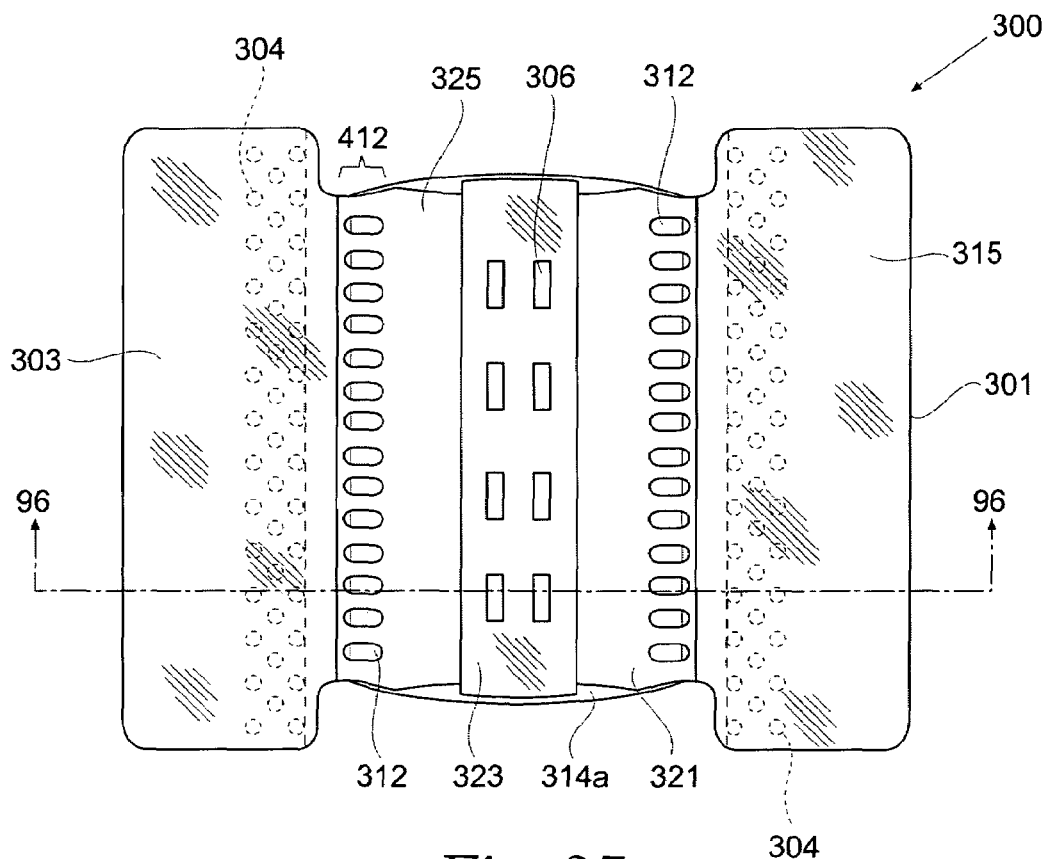
FIG. 95 is a top plan view of the device illustrated in FIG. 94.
Figure 96:
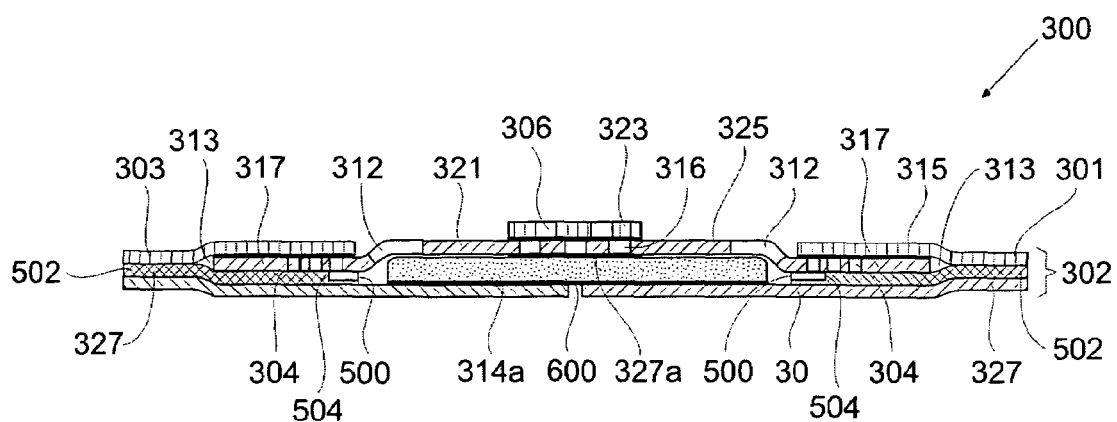
FIG. 96 is a cross sectional view of the device shown in FIGS. 94 and 95 and taken along line 96-96 of FIG. 95.
Figure 97:
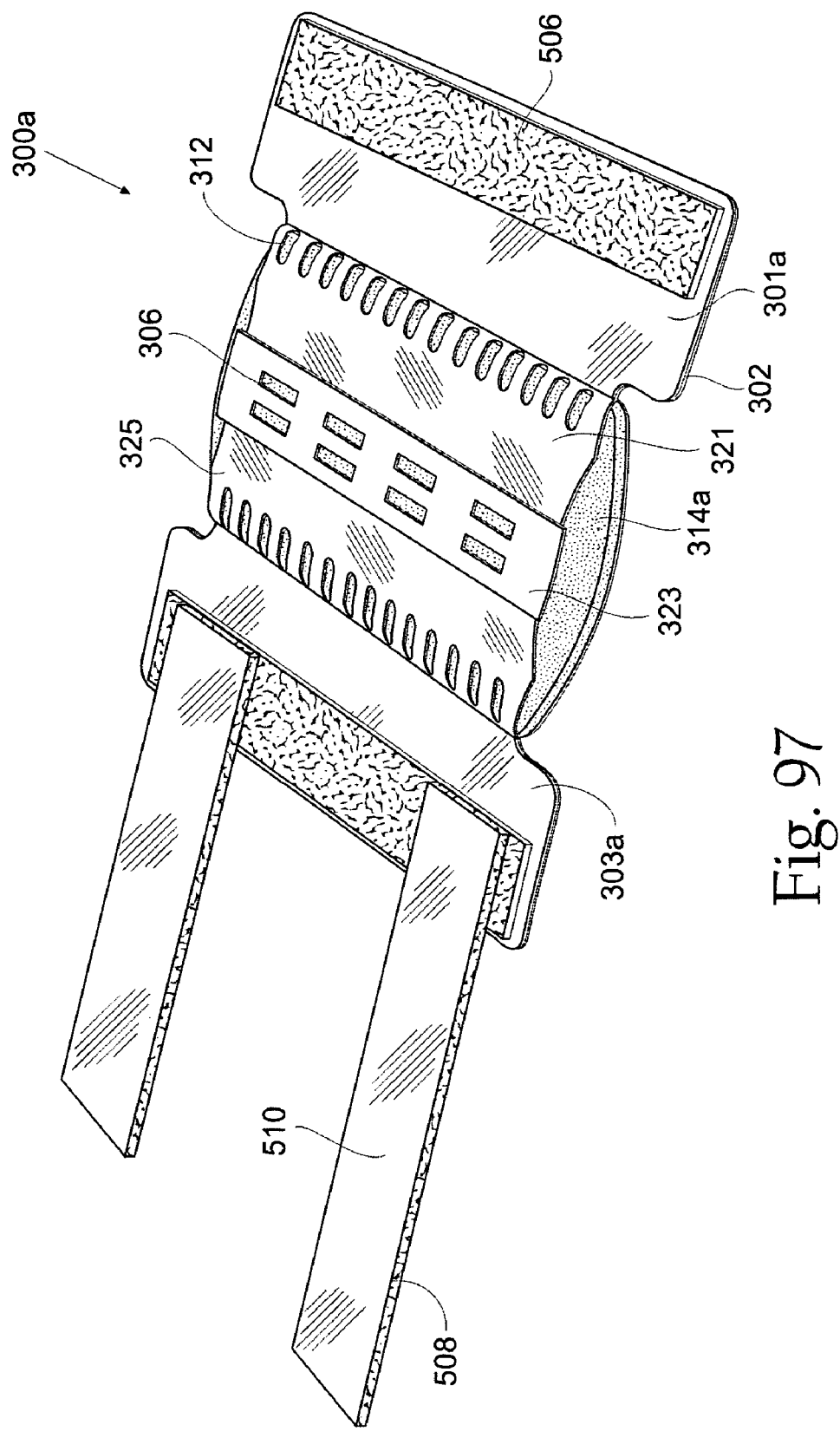
FIG. 97 is a perspective view of a device similar to that of FIGS. 94-96, but showing a hook and loop type fastener in combination with adhesive fastening means.
Figure 98:
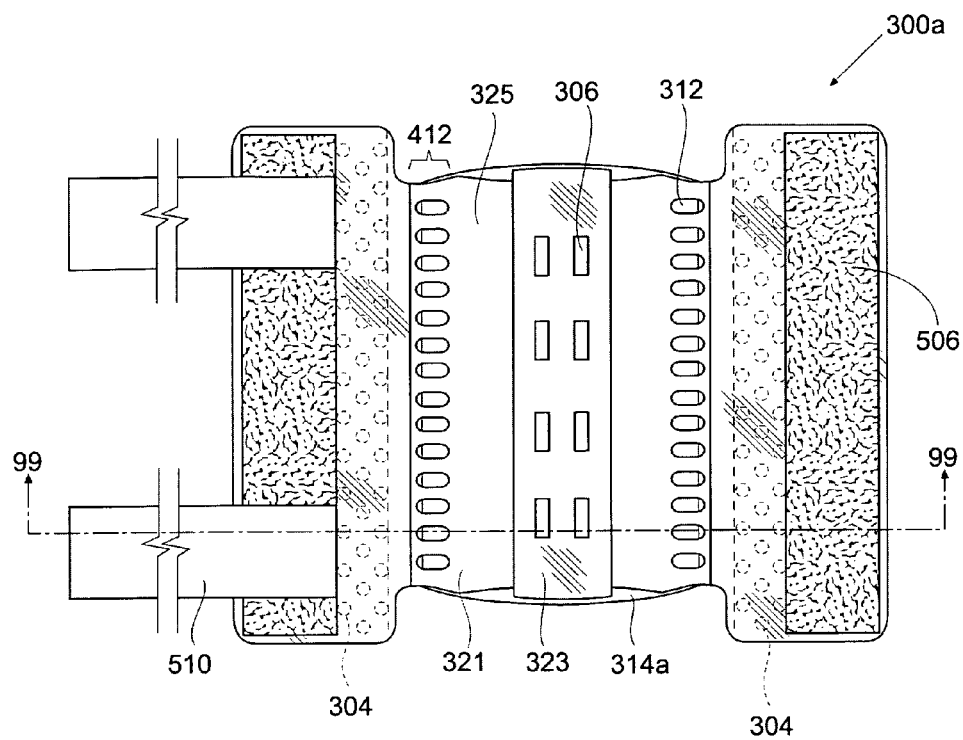
FIG. 98 is a top plan view of the device illustrated in FIG. 97.
Figure 99:
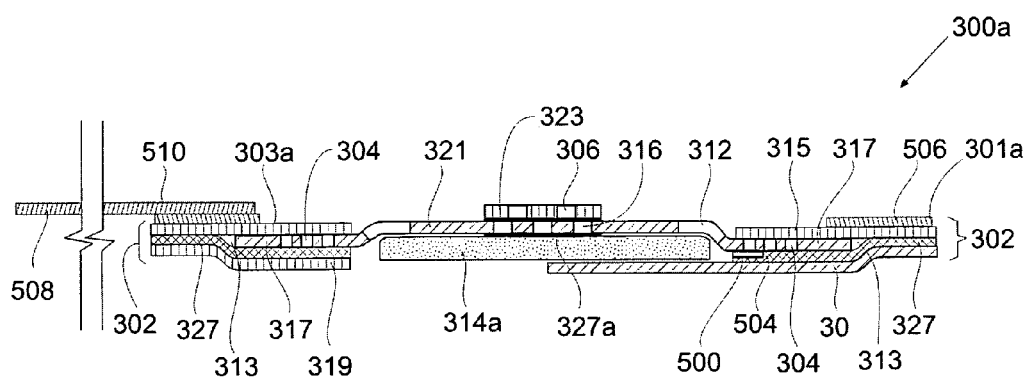
FIG. 99 is a cross sectional view of the device shown in FIGS. 97-98, and taken along line 99-99 of FIG. 98.

Referring now to FIGS. 94-96 another embodiment, similar to the structure disclosed in FIGS. 35-52, and 61-76 is shown. As seen, the dressing structure 300 is comprised of a multiple layer or laminated material 302 at anchor sections 301 and 303, and a multiple layer or laminated material 302a at its center section 325. As may be seen particularly in FIG. 96, the laminated material 302 includes a top surface or layer 315 made of TYVEC brand material or spun silk, and a bottom surface or layer 319 comprised of a hypo-allergenic adhesive layer 327, covered with a silicone release liner 30. The laminated material 302 preferably further includes a channel 313 into which margins 317 of an elastic member 321 are engaged, thereby locating the margins 317 between the top surface layer 315 and the adhesive layer 327. The elastic member 321 may be formed of latex rubber or other suitably elastic material. The margins 317 preferably includes openings 304 which allow the adhesive layer 327 to extend through the openings 304 to communicate with the top surface layer 315, thereby coupling the top surface layer 315 to the margins 317. This action effectively locks the elastic material 321 into position so that it may not be easily removed by tension when stretched.

Still referring to FIGS. 94-96, the center section 325 may be observed to include a stabilizing section 323. The stabilizing section 323 may be fabricated of TYVC brand material, spun silk, or any other suitable material. The stabilizing section 323, is preferably bonded to the pad member 314a and elastic member 321 via openings 316, in elastic member 321 which allow an adhesive layer 327a to communicate through the openings 316 with section 323. This action couples the stabilizing section 323, elastic member 321 and pad member 314a at the stabilizing section 323 whereby the pad member 314a is suspended by the elastic member 321 between the anchor sections 301, 303.

The stabilizing section 323 may be further provided with openings 306 which allow easy dispersal of medicaments or other substances (not shown) through the pad member 314a to an epidermis (not shown in these views). It is further to be noted that the pad member 314a may be formed of a hydrophilic material (as shown), gauze, or any other suitable material. Furthermore, it may be noted that a silicone surface material 600 may be applied to any pad member surface, to aid in shear reduction on the epidermal surface to which the device is affixed. Alternatively, the pad member may be entirely replaced by a silicone surface material (not shown).

Additionally, previously described embodiments may also include a hydrophilic material as part of the pad or center section construction.

The dressing structure 300 seen in FIGS. 94-96 may be further observed to include a barrier layer 500. The barrier layer 500 preferably overlays at least a portion of the adhesive layer 327, between the adhesive layer 327 and the elastic member 321. As is seen particularly in FIG. 96, the adhesive layer 327 may preferably include a distal end 502 and a proximal end 504. The barrier layer 500 preferably overlays a portion at the proximal end 504 of adhesive layer 327. The barrier layer 500 reduces the lifting or peel force on the adhesive layer 327 thereby increasing the stability of the bond between the adhesive layer 327 and an epidermis (not shown) when the dressing structure 300 is applied and the elastic member 321 is stretched between the anchor sections 301, 303. As illustrated in previous embodiments, when this embodiment is applied over a wound or other predetermined area, the elastic member 321 acts much as a leaf spring and applies a positive pressure downward through the pad member 314a. The additional use of a hydrophilic pad material as shown in the embodiment of FIGS. 94-96 works in combination with the positive pressure downward pressure to effectively maintain contact of the pad member 314a with the predetermined area.

As seen in FIGS. 94-96, openings 312 may be located in a tension adjustment section 412 of the elastic member 321. As mentioned previously with regard to other embodiments, as the tension adjustment section 412 of the elastic member 321 is stretched to apply the dressing structure 300, the openings 312 will become distorted. The greater the stretching, the greater the tension applied to the elastic member 321. In this way the amount of tension applied to the elastic member 321 may be seen, allowing a person applying the dressing to keep the pressure relatively constant.

Figure 100:
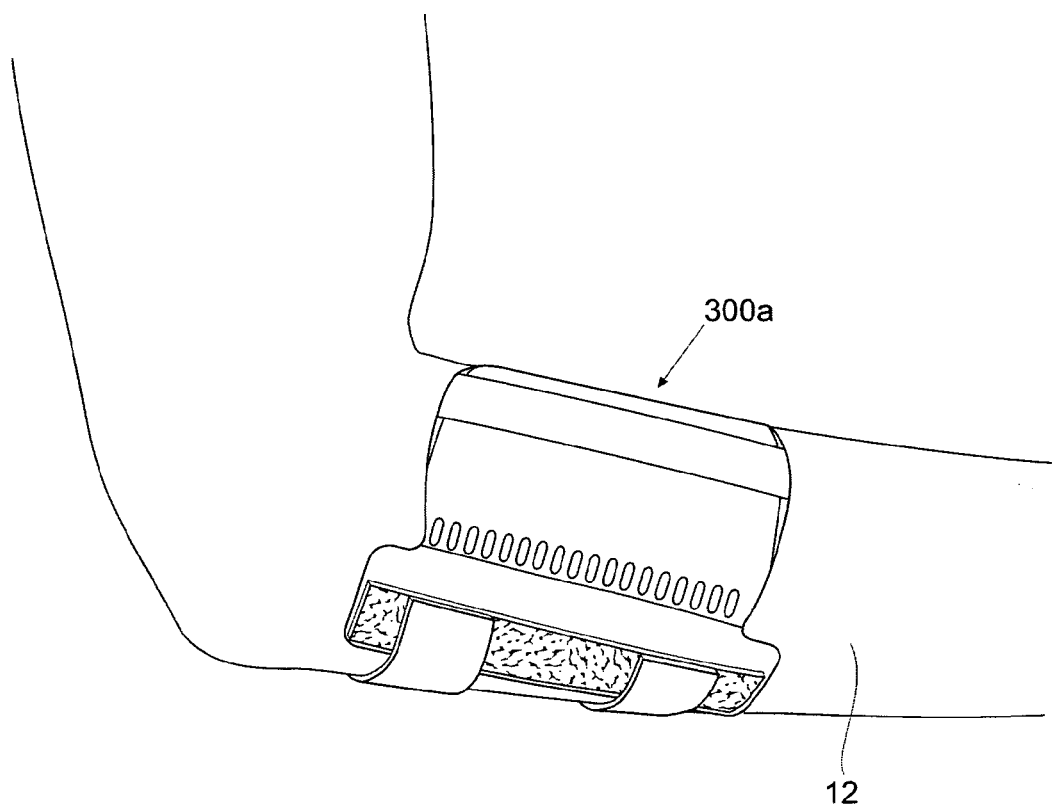
FIG. 100 illustrates the device shown in FIGS. 97-99 in use around a human limb.
Figure 101:
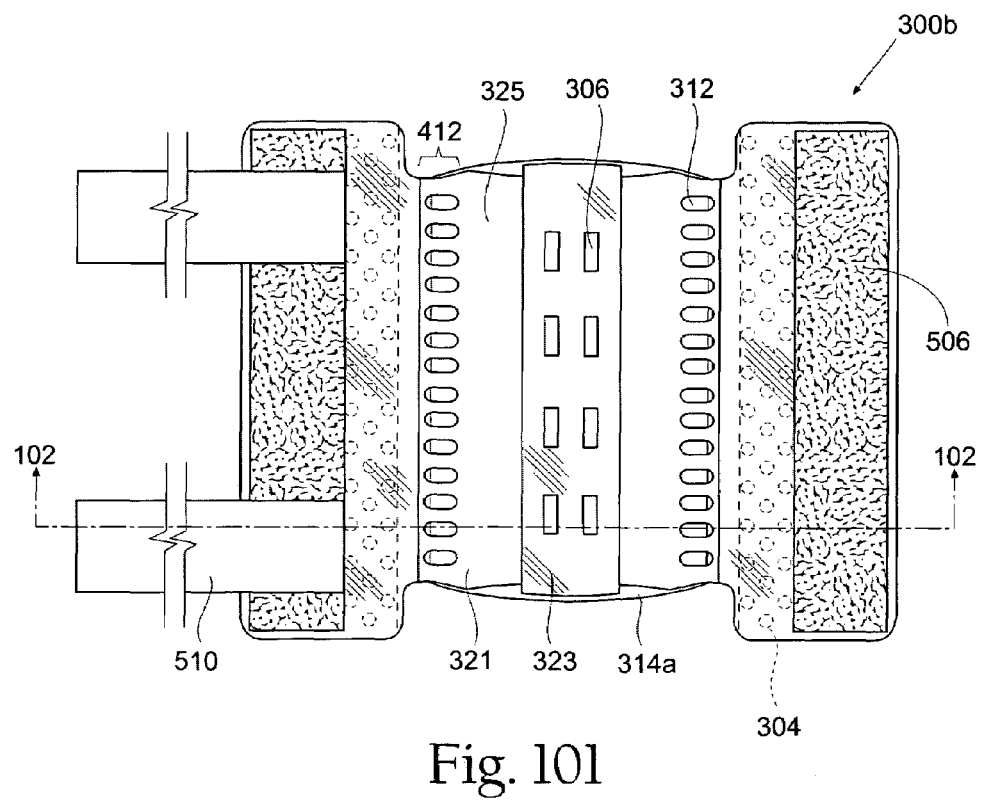
FIG. 101 is a top plan view of a device similar to that shown in FIGS. 97-100, but showing use of a hook and loop type fastener absent the additional adhesive attachment means illustrated in previous views.
Figure 102:
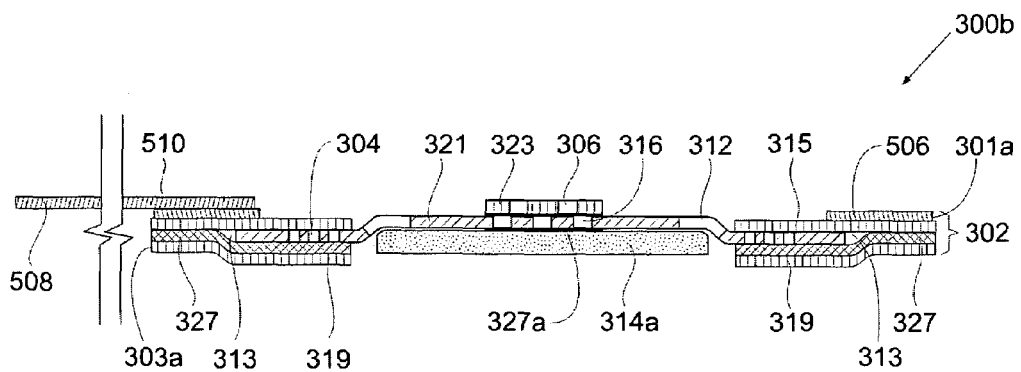
FIG. 102 is a cross sectional view of the device shown in FIG. 101 and taken along line 102-102 thereof.

Referring now to FIGS. 97-100 another embodiment of the present invention may be seen. Similarly to the embodiment seen in FIGS. 94-96, the dressing structure 300a seen in these views is composed of a multiple layer or laminated material 302 at anchor sections 301a and 303a, and a multiple layer or laminated material 302a at its center section 325. However, as seen particularly in FIG. 99, anchor section 301a includes a plurality of loop members 506. Anchor section 303a preferably includes at least one laterally extending portion 510 having hook members 508 arranged to be fastened to the loop members 506 on anchor section 301a. This arrangement allows the dressing structure 300a to be easily affixed to a limb 12, as seen in FIG. 100, and allows a user to inspect or clean the wound without removing the adhesive layer from the skin surface. As may be seen particularly in FIG. 99, the laminated material 302 at anchor section 301a includes a top surface or layer 315 made of TYVEC brand material, spun silk, or similar material. The top surface 315 includes a plurality of loop members 506, as mentioned. The bottom surface or layer 319 is comprised of a hypo-allergenic adhesive layer 327, covered with a silicone release liner 30. The laminated material 302 at anchor section 303a includes a top surface layer similar to that of anchor structure 301a, but including a laterally extending portion 510 having hook members 508 arranged to be fastened to the loop members 506 on anchor structure 301a. The laterally extending portion may be attached to top surface 315 by conventional means such as stitching, adhesive, or by way of corresponding loop members on anchor structure 301a, as shown. Further, the laminated material 302 at anchor section 303a preferably includes a bottom surface 319 of a TYVC brand material, spun silk, or any other suitable material, attached by way of an adhesive layer 327, rather than the adhesive layer covered with a release liner as shown at anchor section 301a. The laminated material at anchor structures 301a and 303a preferably includes a channel 313 into which margins of elastic member 321 are engaged as discussed in connection to the embodiment of FIGS. 94-96.

Similarly to the embodiment of FIGS. 94-96, the device illustrated in FIGS. 97-100 may further include a barrier layer 500. The barrier layer 500 preferably overlays a portion of the proximal end 504 of the adhesive layer 327 at anchor section 301a.

Illustrated in FIGS. 101-104 is another alternative embodiment dressing structure 300b may be seen. As in the embodiment shown in FIGS. 97-100, the device of FIGS. 101-104 is provided with a plurality of loop members 506 and hook members 508. However, as seen the laminated material 302 at anchor sections 301a, 303a is provided with a bottom surface 319 of TYVC brand material, spun silk, or any other suitable material, rather than an adhesive layer as previously illustrated. This arrangement allows the dressing structure 300b to be secured to an epidermis (not shown) without the use of adhesive which, over prolonged use, may become an irritant to sensitive application sites.

Figure 103:
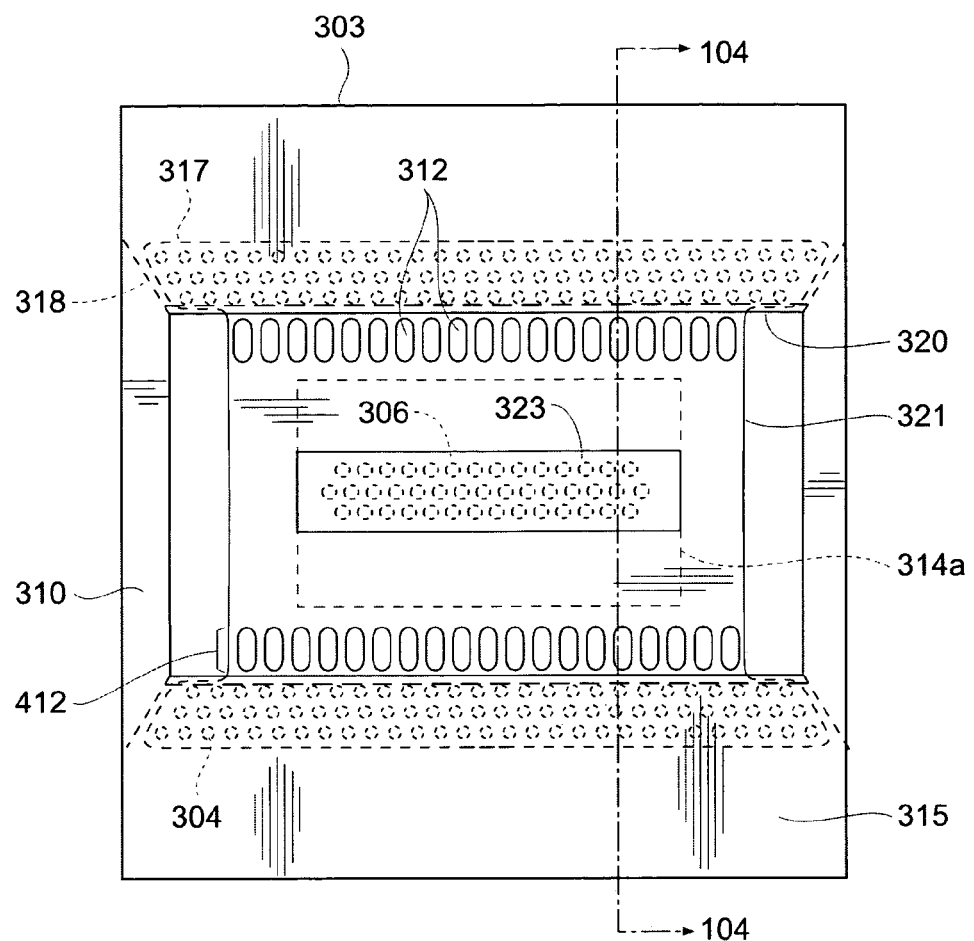
FIG. 103 is a top plan view of an embodiment showing a barrier layer.
Figure 104:
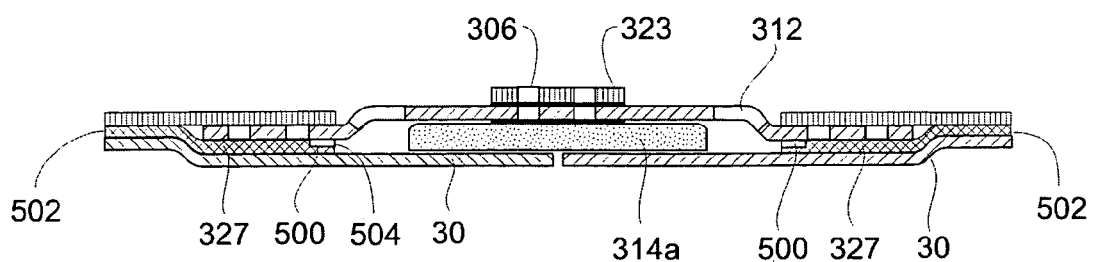
FIG. 104 is a cross sectional view of the device shown in FIG. 103 and taken along line 104-104 thereof.

Referring now to FIGS. 103 and 104 another alternative embodiment of the dressing structure 300a may be seen. As illustrated, the device previously disclosed with reference to FIG. 35 is illustrated but including a non-adhesive barrier layer 500 coextensive with and overlaying a portion of the adhesive layer 327. The device further includes a pad member 314a composed of a hydrophilic material. While not illustrated as such, it is to be understood that the device may be fabricated with a barrier layer 500 while including a pad member 314 of any conventional material, such as gauze.

Figure 105:
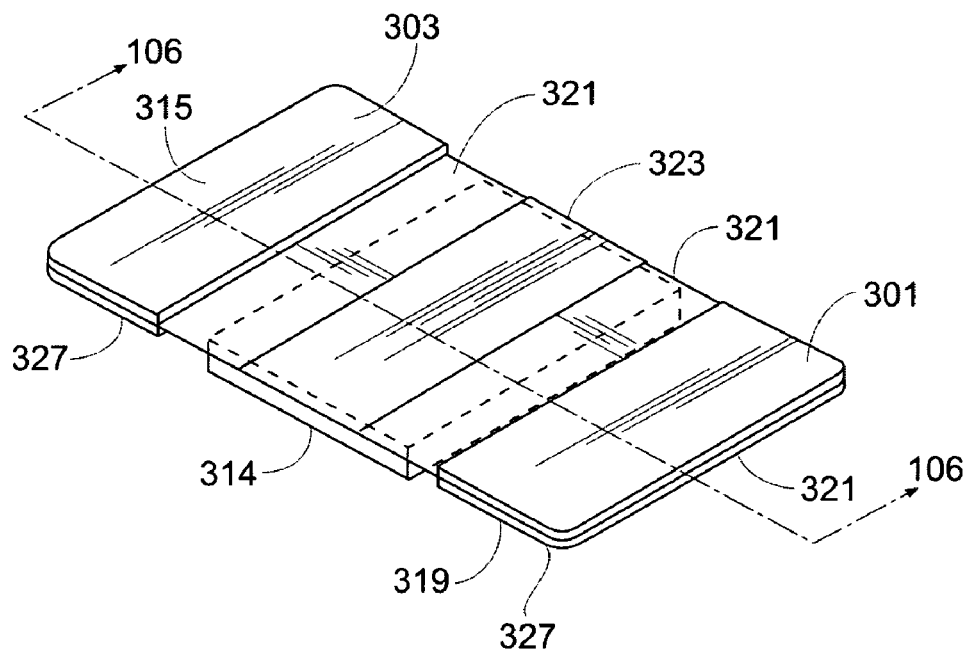
FIG. 105 is a perspective view of another embodiment including a barrier layer.
Figure 106:
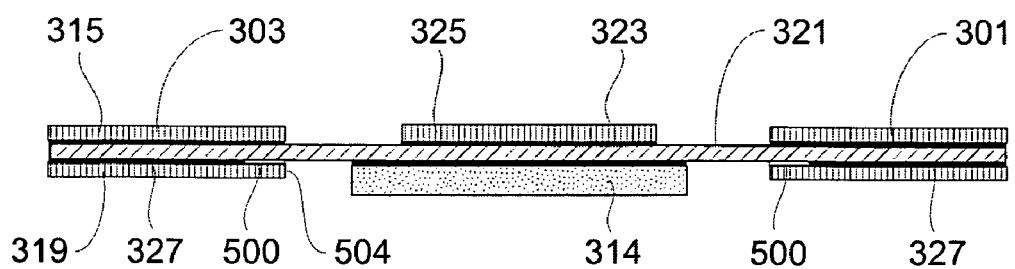
FIG. 106 is a cross sectional view of the device seen in FIG. 105 and taken along line 106-106 thereof.

Illustrated in FIGS. 105 and 106 is another alternative embodiment, seen as the device previously disclosed with regard to FIG. 53. In this embodiment, the dressing 300a is composed of a piece of elastic member 321, such as latex, having two ends to which anchors 310a and 303b are respectively attached. The ends of the elastic member 321 are simply sandwiched between the top surface member 315 and the bottom surface layer 319. A stabilizing section member 323 is adhered across the center section 325 of the elastic member 321, and a pad member 314a is adhered to the underside of the elastic member 321. As illustrated, the device may be further provided with a barrier layer 500 as discussed with regard to previous embodiments. The barrier layer is preferably located between adhesive layer 327 and elastic member 321 at a proximal end portion 504 of adhesive layer 327. The pad member 314a may be fabricated of a hydrophilic material as shown or any other suitable material.

Figure 107:
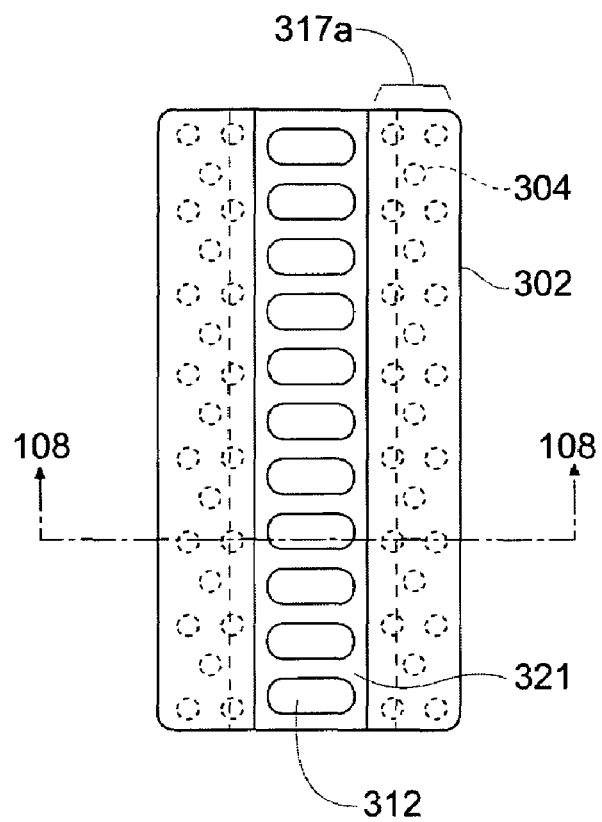
FIG. 107 is a top plan view of another embodiment including a barrier layer.
Figure 108:
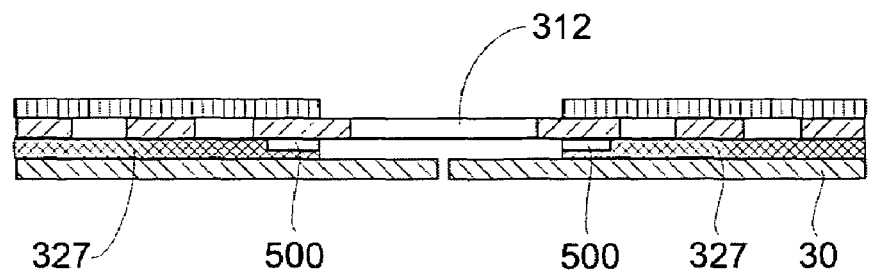
FIG. 108 is a cross sectional view of the device seen in FIG. 107 and taken along line 108-108 thereof.
Figure 109:
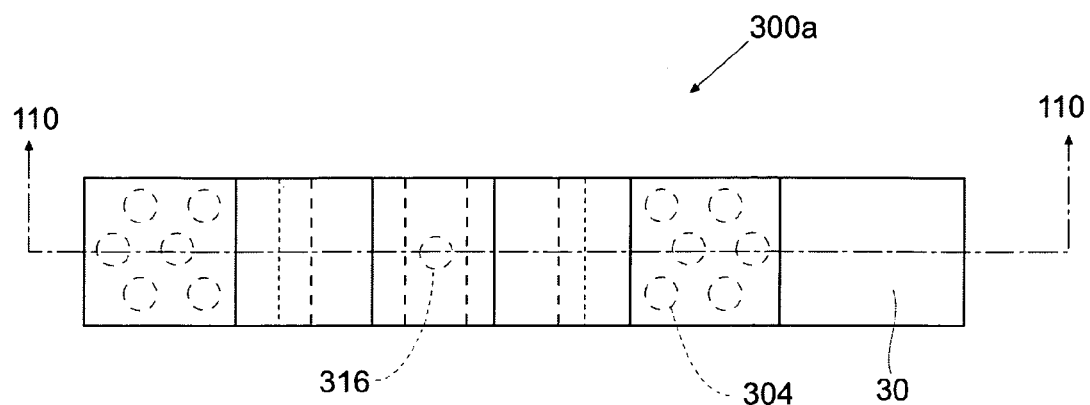
FIG. 109 is a top plan view of another embodiment including a barrier layer.
Figure 110:
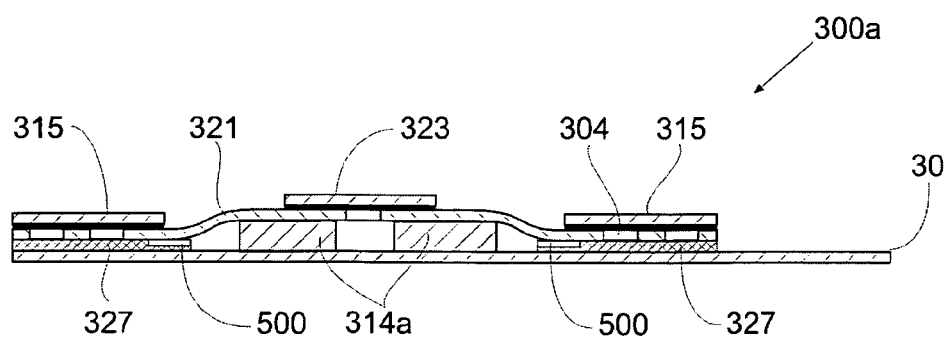
FIG. 110 is a cross sectional view of the device seen in FIG. 109 and taken along line 110-110 thereof.
Figure 111:
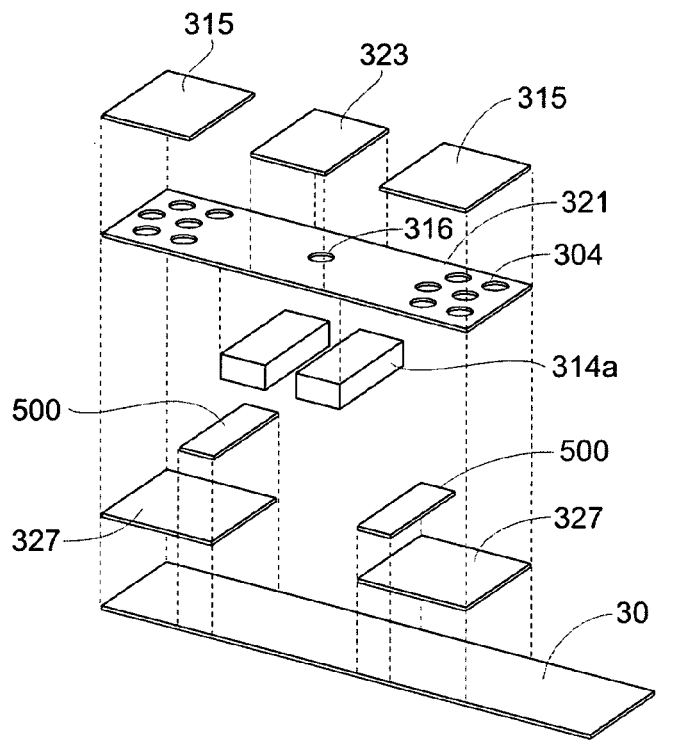
FIG. 111 is an exploded view of one embodiment of the present invention and showing a plurality of barrier layers.
Figure 112:
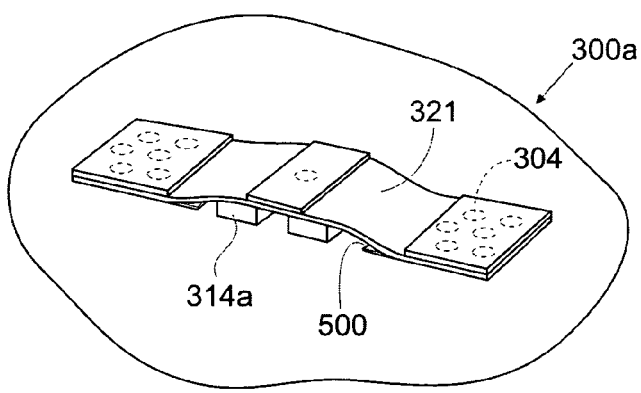
FIG. 112 is a perspective view of the embodiment seen in FIG. 111 in place on an epidermis.
Figure 113:
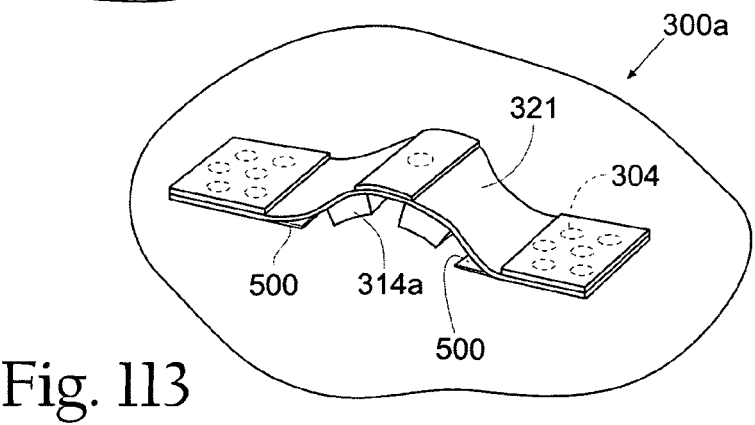
FIG. 113 is a view similar to that of FIG. 112, but showing the device in an arched position to more clearly show the barrier strip.

Seen in FIGS. 107 and 108 is another embodiment of the dressing mechanism 300a, but similar to the embodiment disclosed in FIGS. 55-60. In this embodiment the entire elastic member 321 is essentially comprised of tensioning section 412 having openings 312. The various components function as previously described, however the device includes the feature of a non-adhesive barrier layer 500. As described with regard to FIGS. 95-106, the barrier layer 500 is preferably located between adhesive layer 327 and elastic member 321 at the proximal end portion 504 of adhesive layer 327.

FIGS. 109-113 illustrate an alternative embodiment including multiple pad members 314a and the use of a barrier layer 500 between the adhesive layer 327 and elastic member 321 as described previously.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. An assembly for positioning the epidermis comprising:
a first end piece adapted to be anchored to the epidermis;
at least one elastic material coupled to the first end piece;
a second end piece adapted to be anchored to the epidermis, said at least one elastic material being further coupled to said second end piece;
the first end piece and the second end piece each having a first side;
the first end piece and the second end piece each having an adhesive layer, said adhesive layer having a first adhesive side and a second adhesive side, said first adhesive side being coupled to a respective first side of said first end piece and said second end piece, and wherein at least a portion of each adhesive layer includes a coextensive, overlaying layer, said coextensive overlaying layer having a first side and a second side, said overlaying layer being located between said first adhesive side and the respective first sides of said first end piece and said second end piece, wherein said first side of said overlaying layer is adhered to said adhesive layer and wherein at least a portion of said second side of said overlaying layer is in non-adhering contact with said respective first sides of said first end piece and said second end piece.

2. The assembly of claim 1 wherein at least one first side further includes a plurality of slits having a predetermined shape.

3. The assembly of claim 2 wherein the predetermined shape of the slits is a U shape.

4. The assembly of claim 1 wherein at least one of said first end piece and said second end piece is an anchoring mechanism.

5. The assembly of claim 1 wherein the second end piece is a lifting end piece.

6. The assembly of claim 1 wherein said at least one elastic material includes at least one side having a medicinal material thereon.

7. The epidermal positioning mechanism of claim 1 wherein said overlaying layer comprises a non-adhesive material.

* * * * *